United States Patent
Inoue et al.

(10) Patent No.: US 8,598,785 B2
(45) Date of Patent: Dec. 3, 2013

(54) ORGANOMETALLIC COMPLEX, AND LIGHT-EMITTING ELEMENT, LIGHT-EMITTING DEVICE, ELECTRONIC DEVICE, AND LIGHTING DEVICE USING THE ORGANOMETALLIC COMPLEX

(75) Inventors: Hideko Inoue, Kanagawa (JP); Satoshi Seo, Kanagawa (JP); Nobuharu Ohsawa, Kanagawa (JP)

(73) Assignee: Semiconductor Energy Laboratory Co., Ltd (JP)

( * ) Notice: Subject to any disclaimer, the term of this patent is extended or adjusted under 35 U.S.C. 154(b) by 0 days.

(21) Appl. No.: 13/550,720

(22) Filed: Jul. 17, 2012

(65) Prior Publication Data

US 2012/0280220 A1    Nov. 8, 2012

Related U.S. Application Data

(63) Continuation of application No. 12/688,075, filed on Jan. 15, 2010, now Pat. No. 8,227,975.

(30) Foreign Application Priority Data

Jan. 21, 2009    (JP) .................................. 2009-010744

(51) Int. Cl.
*H05B 33/00* (2006.01)

(52) U.S. Cl.
USPC ........................... 313/504; 313/506; 428/690

(58) Field of Classification Search
USPC ............ 313/504, 506; 428/690, 917; 544/225
See application file for complete search history.

(56) References Cited

U.S. PATENT DOCUMENTS

| | | |
|---|---|---|
| 7,589,203 B2 | 9/2009 | Stossel et al. |
| 2005/0221123 A1 | 10/2005 | Inoue et al. |
| 2006/0127696 A1 | 6/2006 | Stossel et al. |
| 2006/0263636 A1 | 11/2006 | Ohsawa et al. |
| 2007/0244320 A1 | 10/2007 | Inoue et al. |
| 2008/0286604 A1 | 11/2008 | Inoue et al. |
| 2009/0015143 A1 | 1/2009 | Inoue et al. |
| 2009/0033209 A1 | 2/2009 | Seo et al. |

FOREIGN PATENT DOCUMENTS

JP    2006-120762    5/2006

OTHER PUBLICATIONS

Zhang, G-L et al, "Synthesis and Phosphorescence of a New Iridium(III) Pyrazine Complex," Wuli Huaxue Xuebao, Acta Physico-Chimica Sinica, vol. 19, No. 10, Oct. 19, 2003, pp. 889-891 (with full English translation).

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with full English translation).

O'Brien, D.F. et al, "Improved Energy Transfer in Electrophosphorescent Devices," Applied Physics Letters, vol. 74, No. 3, Jan. 18, 1999, pp. 442-444.

Inoue, H. et al, "A Reaction of Singlet Oxyen with an Unsaturated Organic Molecule, 6.1.4, Quencher and Photosensitizer," *Basic Chemistry Course Photochemistry I*, Maruzen Co., Ltd., Sep. 30, 1999, pp. 106-110 (with English abstract).

Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L1502-L1504.

Baldo, M.A. et al, "High-Efficiency Fluorescent Organic Light-Emitting Devices Using a Phosphorescent Sensitizer," Nature, vol. 403, Feb. 17, 2000, pp. 750-753.

Thompson, M.E. et al, "Phosphorescent Materials and Devices," Proceedings of the 10th International Workshop on Inorganic and Organic Electroluminescence, EL '00, Dec. 4, 2000, pp. 35-38.

Duan, J.-P. et al, "New Iridium Complexes as Highly Efficient Orange-Red Emitters in Organic Light-Emitting Diodes," Advanced Materials, vol. 15, No. 3, Feb. 5, 2003, pp. 224-228.

Zhang, G-L et al, "Synthesis and Phosphorescence of a New Iridium(III) Pyrazine Complex," Wuli Huaxue Xuebao, Acta Physico-Chimica Sinica, vol. 19, No. 10, Oct. 19, 2003, pp. 889-891 (with English abstract).

Slater, J.W. et al, "Cyclometallated Nitrogen Heterocycles," Journal of Organo Metallic Chemistry, vol. 688, Aug. 29, 2003, pp. 112-120.

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).

*Primary Examiner* — Joseph L Williams
(74) *Attorney, Agent, or Firm* — Husch Blackwell LLP

(57) ABSTRACT

To provide a novel organometallic complex capable of emitting phosphorescence by using an organic compound with which a variety of derivatives can be easily synthesized as a ligand. In addition, to provide an organometallic complex which exhibits red emission. To provide an organometallic complex formed by ortho-metalation of an m-alkoxyphenyl pyrazine derivative represented by General Formula (G0) below with respect to an ion of a metal belonging to Group 9 or Group 10. In addition, to provide an organometallic complex which exhibits red emission formed by ortho-metalation of an m-alkoxyphenyl pyrazine derivative represented by General Formula (G0) below with respect to an ion of a metal belonging to Group 9 or Group 10.

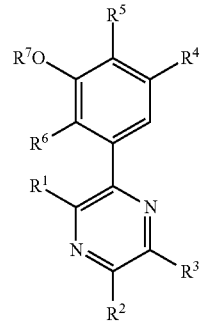

(G0)

11 Claims, 29 Drawing Sheets

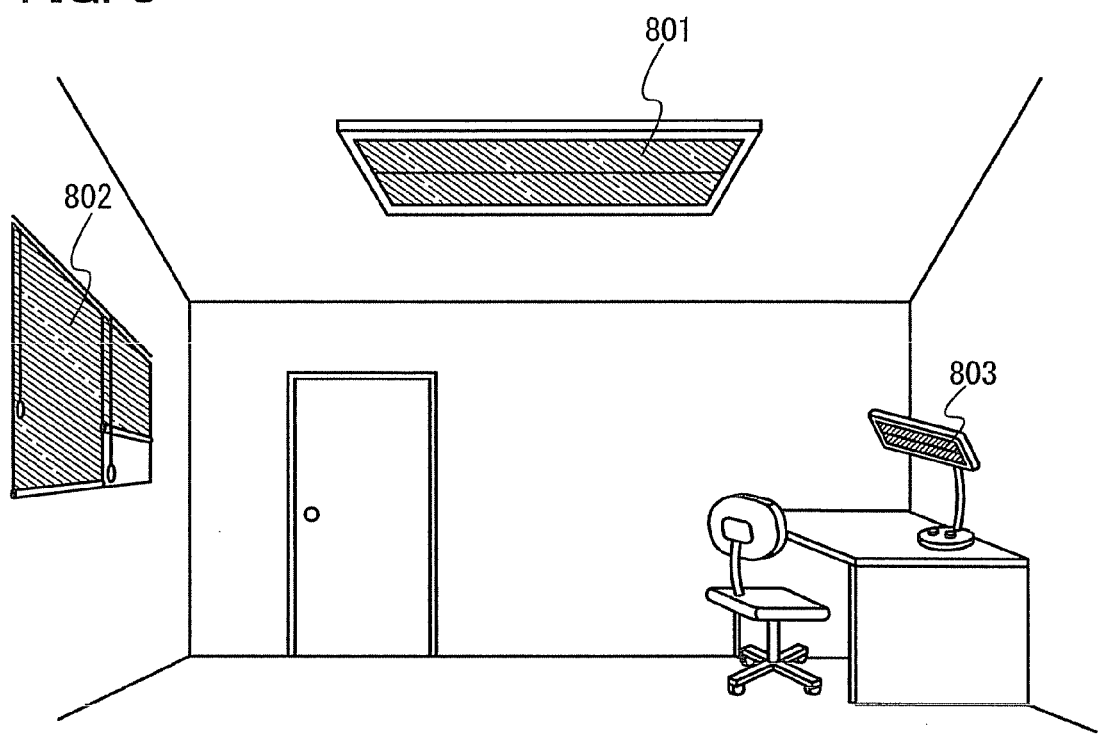

US 8,598,785 B2

ORGANOMETALLIC COMPLEX, AND LIGHT-EMITTING ELEMENT, LIGHT-EMITTING DEVICE, ELECTRONIC DEVICE, AND LIGHTING DEVICE USING THE ORGANOMETALLIC COMPLEX

This application is a continuation of application Ser. No. 12/688,075 filed on Jan. 15, 2010 now U.S. Pat. No. 8,227,975.

BACKGROUND OF THE INVENTION

1. Field of the Invention

The present invention relates to an organometallic complex. In particular, the present invention relates to an organometallic complex that is capable of converting a triplet excited state into luminescence.

2. Description of the Related Art

Organic compounds are brought into an excited state by the absorption of light. Through this excited state, various reactions (photochemical reactions) are caused in some cases, or luminescence is generated in some cases. Therefore, the organic compounds have a wide range of applications.

As one example of the photochemical reactions, a reaction of singlet oxygen with an unsaturated organic molecule (oxygen addition) is known (refer to Non-Patent Document 1). Since the ground state of an oxygen molecule is a triplet state, oxygen in a singlet state (singlet oxygen) is not generated by direct photoexcitation. However, in the presence of another triplet excited molecule, singlet oxygen is generated to cause an oxygen addition reaction. In this case, a compound capable of forming the triplet excited molecule is referred to as a photosensitizer.

As described above, for generation of singlet oxygen, a photosensitizer capable of forming a triplet excited molecule by photoexcitation is needed. However, the ground state of an ordinary organic compound is a singlet state; therefore, photoexcitation to a triplet excited state is forbidden transition and generation of a triplet excited molecule is difficult. A compound that can easily cause intersystem crossing from the singlet excited state to the triplet excited state (or a compound that allows the forbidden transition of photoexcitation directly to the triplet excited state) is thus required as such a photosensitizer. In other words, such a compound can be used as the photosensitizer and is useful.

The above compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Application fields of a compound capable of exhibiting phosphorescence, that is, a compound capable of converting the triplet excited state into luminescence (hereinafter, referred to as a phosphorescent compound), include a light-emitting element including an organic compound as a light-emitting substance.

This light-emitting element has a simple structure in which a light-emitting layer including an organic compound that is a light-emitting substance is provided between electrodes. This light-emitting element attracts attention as a next-generation flat panel display element in terms of characteristics such as being thin and light in weight, high speed response, and direct current low voltage driving. Further, a display device including this light-emitting element is superior in contrast, image quality, and wide viewing angle.

The light-emitting element including an organic compound as a light-emitting substance has a light emission mechanism that is of a carrier injection type: voltage is applied between electrodes where a light-emitting layer is interposed, electrons and holes injected from the electrodes are recombined to make the light-emitting substance excited, and then light is emitted in returning from the excited state to the ground state. As in the case of photoexcitation described above, types of the excited state include a singlet excited state (S*) and a triplet excited state (T*). The statistical generation ratio thereof in the light-emitting element is considered to be S*:T*=1:3.

At a room temperature, a compound capable of converting a singlet excited state to luminescence (hereinafter, referred to as a fluorescent compound) exhibits only luminescence from the singlet excited state (fluorescence), not luminescence from the triplet excited state (phosphorescence). Accordingly, the internal quantum efficiency (the ratio of the number of generated photons to the number of injected carriers) of a light-emitting element including the fluorescent compound is assumed to have a theoretical limit of 25%, on the basis of S*:T*=1:3.

On the other hand, in a case of a light-emitting element including the phosphorescent compound described above, the internal quantum efficiency thereof can be improved to 75% to 100% in theory; namely, the emission efficiency thereof can be 3 to 4 times as much as that of the light-emitting element including a fluorescent compound. Therefore, the light-emitting element including a phosphorescent compound has been actively developed in recent years in order to achieve a highly-efficient light-emitting element (refer to Non-Patent Document 2). An organometallic complex that contains iridium or the like as a central metal is particularly attracting attention as a phosphorescent compound because of its high phosphorescence quantum yield.

REFERENCE

Non-Patent Document

[Non-Patent Document 1] Inoue, Haruo et al., *Basic Chemistry Course PHOTOCHEMISTRY I*, pp. 106-110, Maruzen Co., Ltd.

[Non-Patent Document 2] Zhang, Guo-Lin et al. (2004) *Gaodeng Xuexiao Huaxue Xuebao*, vol. 25, No. 3, pp. 397-400.

It is an object of one embodiment of the present invention to provide a novel organometallic complex capable of emitting phosphorescence by using an organic compound with which a variety of derivatives can be easily synthesized as a ligand. In addition, it is an object of one embodiment of the present invention to provide an organometallic complex which exhibits red emission.

SUMMARY OF THE INVENTION

One embodiment of the present invention is an organometallic complex formed by ortho-metalation of an m-alkoxyphenyl pyrazine derivative represented by General Formula (G0) below with respect to an ion of a metal belonging to Group 9 or Group 10. In addition, one embodiment of the present invention is an organometallic complex exhibiting red phosphorescent emission, which is formed by ortho-metalation of an m-alkoxyphenyl pyrazine derivative represented by General Formula (G0) below with respect to an ion of a metal belonging to Group 9 or Group 10.

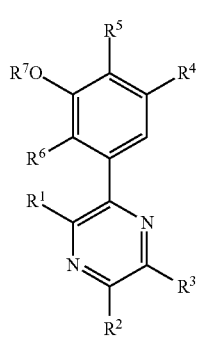

(G0)

Therefore, one embodiment of the present invention is an organometallic complex having a structure represented by General Formula (G1) below.

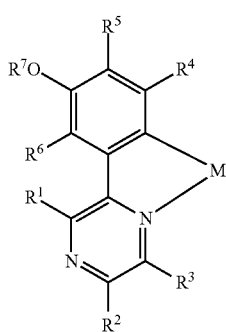

(G1)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ and $R^3$ each independently represent either hydrogen or an alkyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; and M is a central metal and represents either an element belonging to Group 9 or an element belonging to Group 10.

In addition, in General Formula (G1) above, $R^3$ or both $R^3$ and $R^6$ preferably represent hydrogen in terms of synthesis yield, in which case steric hindrance of a pyrazine derivative is reduced. Thus, a more preferred embodiment is an organometallic complex having a structure represented by General Formula (G2) or (G3) below.

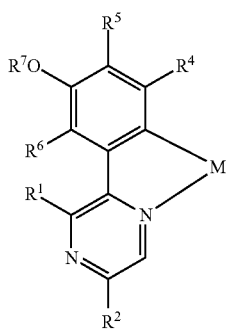

(G2)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an alkyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain allyl group having 1 to 4 carbon atoms; the alkyl group may be substituted with a phenyl group; and M is a central metal and represents either an element belonging to Group 9 or an element belonging to Group 10.

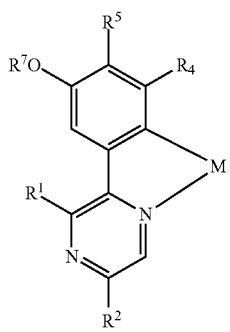

(G3)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an alkyl group having 1 to 4 carbon atoms; $R^4$ and $R^5$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; and M is a central metal and represents either an element belonging to Group 9 or an element belonging to Group 10.

Here, specifically, the organometallic complex having the structure represented by General Formula (G1) above is preferably an organometallic complex represented by General Formula (G4) below, in which case it can be easily synthesized.

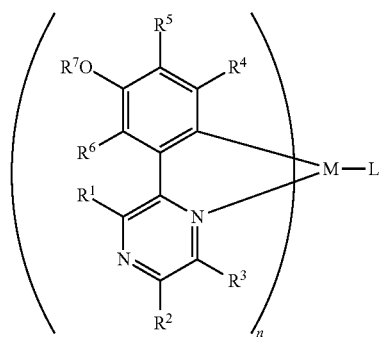

(G4)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ and $R^3$ each independently represent either hydrogen or an alkyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; L represents a monoanionic ligand; and n is 2 when the central metal is an element belonging to Group 9, and n is 1 when the central metal is an element belonging to Group 10.

Here, specifically, the organometallic complex having the structure represented by General Formula (G2) above is preferably an organometallic complex represented by General Formula (G5) below, in which case it can be easily synthesized.

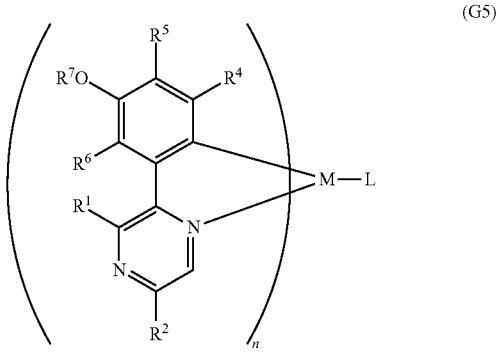

(G5)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an allyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; L represents a monoanionic ligand; and n is 2 when the central metal is an element belonging to Group 9, and n is 1 when the central metal is an element belonging to Group 10.

Here, specifically, the organometallic complex having the structure represented by General Formula (G3) above is preferably an organometallic complex represented by General Formula (G6) below, in which case it can be easily synthesized.

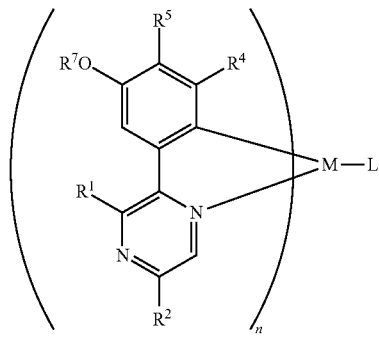

(G6)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an alkyl group having 1 to 4 carbon atoms; $R^4$ and $R^5$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; L represents a monoanionic ligand; and n is 2 when the central metal is an element belonging to Group 9, and n is 1 when the central metal is an element belonging to Group 10.

The above-described monoanionic ligand L is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. More preferably, the monoanionic ligand L is a monoanionic ligand represented by Structural Formulae (L1) to (L8) below. Since these ligands have high coordinative ability and can be obtained at low price, they are useful.

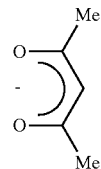

(L1)

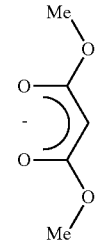

(L2)

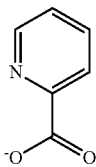
(L3)

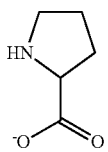
(L4)

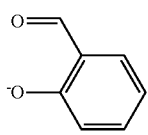
(L5)

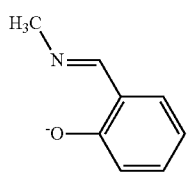
(L6)

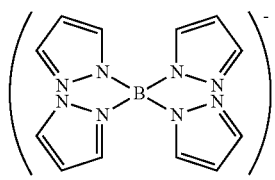
(L7)

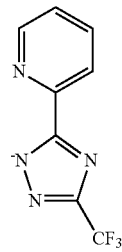
(L8)

For more efficient emission of phosphorescence, a heavy metal is preferable as a central metal in terms of a heavy atom effect. Therefore, one embodiment of the present invention is the above-described organometallic complexes in each of which the central metal M is iridium or platinum.

Here, specifically, the organometallic complex having the structure represented by General Formula (G1) above is preferably an organometallic complex represented by General Formula (G7) below, in which case it can be easily synthesized.

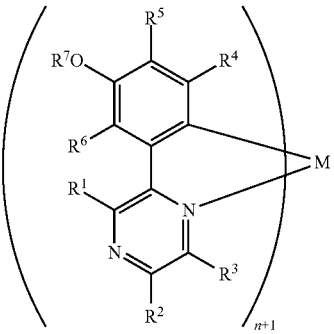
(G7)

In the formula, $R^1$ represents any of an allyl group having 1 to 4 carbon atoms, an alkoxy group having 1 to 4 carbon atoms, or an alkoxycarbonyl group having 1 to 5 carbon atoms; $R^2$ and $R^3$ each independently represent either hydrogen or an alkyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; and n is 2 when the central metal is an element belonging to Group 9, and n is 1 when the central metal is an element belonging to Group 10.

Here, specifically, the organometallic complex having the structure represented by General Formula (G2) above is preferably an organometallic complex represented by General Formula (G8) below, in which case it can be easily synthesized.

$$\left( \begin{array}{c} R^5 \\ R^7O \quad R^4 \\ R^6 \\ R^1 \quad N \\ N \\ R^2 \end{array} \right)_{n+1} M \tag{G8}$$

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an alkyl group having 1 to 4 carbon atoms; $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; and n is 2 when the central metal is an element belonging to Group 9, and n is 1 when the central metal is an element belonging to Group 10.

Here, specifically, the organometallic complex having the structure represented by General Formula (G3) above is preferably an organometallic complex represented by General Formula (G9) below, in which case it can be easily synthesized.

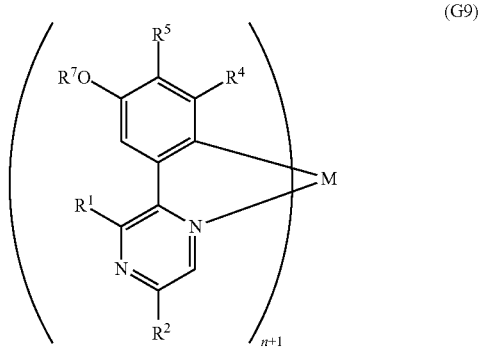

(G9)

In the formula, $R^1$ represents any of an alkyl group having 1 to 4 carbon atoms, an alkoxy group having 1 to 4 carbon atoms, or an alkoxycarbonyl group having 1 to 5 carbon atoms; $R^2$ represents either hydrogen or an allyl group having 1 to 4 carbon atoms; $R^4$ and $R^5$ each independently represents any of hydrogen, an alkyl group having 1 to 4 carbon atoms, an alkoxy group having 1 to 4 carbon atoms, a halogen group, a trifluoromethyl group, or an aryl group having 6 to 12 carbon atoms; $R^7$ represents either a straight-chain alkyl group having 1 to 4 carbon atoms or a branched-chain alkyl group having 1 to 4 carbon atoms; the alkyl group may be substituted with a phenyl group; M is a central metal and represents either an element belonging to Group 9 or an element belonging to Group 10; and n is 2 when the central metal is an element belonging to Group 9, and n is 1 when the central metal is an element belonging to Group 10.

In the organometallic complex having the structure represented by any of General Formulae (G1) to (G3) above (that is, the organometallic complexes represented by General Formulae (G4) to (G9) above are also included), m-alkoxyphenyl pyrazine represented by General Formula (G0) is ortho-metalated with a metal ion. Such a coordinate structure greatly contributes to red phosphorescent emission. Thus, another embodiment of the present invention is a light-emitting material containing an organometallic complex described above.

Further, the organometallic complex of one embodiment of the present invention is very effective for the following reason: the organometallic complex can emit red phosphorescence, that is, it can convert triplet excitation energy into emission and can exhibit red emission, and therefore higher efficiency is possible when the organometallic complex is applied to a light-emitting element. Thus, the present invention also includes, in its scope, a light-emitting element in which the organometallic complex of one embodiment of the present invention is used.

At this time, the organometallic complex of one embodiment of the present invention is effective in use for a light-emitting substance in terms of emission efficiency. Thus, a light-emitting element in which the organometallic complex of one embodiment of the present invention is used for a light-emitting substance is also one embodiment of the present invention.

Further, the present invention includes, in its category, an electronic device and a lighting device in each of which a light-emitting element is included as well as a light-emitting device in which a light-emitting element is included. The light-emitting device in this specification refers to an image display device, a light-emitting device, and a light source (e.g., a lighting device). In addition, the light-emitting device includes, in its category, all of a module in which a light-emitting device is connected to a connector such as a flexible printed circuit (FPC), a tape automated bonding (TAB) tape or a tape carrier package (TCP), a module in which a printed wiring board is provided on the tip of a TAB tape or a TCP, and a module in which an integrated circuit (IC) is directly mounted on a light-emitting element by a chip on glass (COG) method.

According to one embodiment of the present invention, a novel organometallic complex which can emit phosphorescence can be provided by using an organic compound with which a variety of derivatives can be easily synthesized as a ligand. In addition, according to one embodiment of the present invention, an organometallic complex which exhibits red emission can be provided. Moreover, according to one embodiment of the present invention, a light-emitting element, a light-emitting device, an electronic device, and a lighting device in each of which an organometallic complex which exhibits red emission is included can be provided.

BRIEF DESCRIPTION OF THE DRAWINGS

In the accompanying drawings:

FIG. 8 is a view illustrating lighting devices;

DETAILED DESCRIPTION OF THE INVENTION

Figure 1:
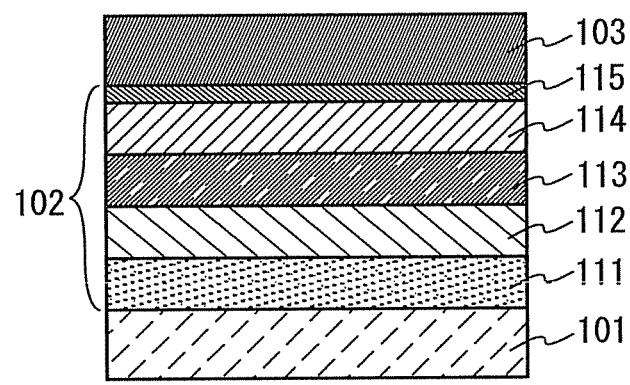
FIG. 1 is a view illustrating a light-emitting element which is one embodiment of the present invention.

Hereinafter, embodiments and examples of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments and examples.

Embodiment 1

In this embodiment, organometallic complexes each of which is one embodiment of the present invention will be described.

<<Synthesis Method of m-alkoxyphenyl Pyrazine Derivative Represented by General Formula (G0)>>

The m-alkoxyphenyl pyrazine derivative represented by General Formula (G0) below can be synthesized by a simple synthesis scheme described below. The m-alkoxyphenyl pyrazine derivative can be obtained, for example, by a reaction between a lithium compound of m-alkoxyaryl or a Grignard reagent of m-alkoxyaryl (A1) and a pyrazine compound (A2) as shown in Scheme (a) below. Alternatively, the m-alkoxyphenyl pyrazine derivative can be obtained by coupling of m-alkoxyphenyl boronic acid (A1') and a halogenated pyrazine compound (A2') as shown in Scheme (a') below. Further alternatively, the m-alkoxyphenyl pyrazine derivative can be obtained by a reaction between diketone of m-alkoxyaryl (A1") and diamine (A2") as shown in Scheme (a") below. Note that, in the formula, X represents a halogen element.

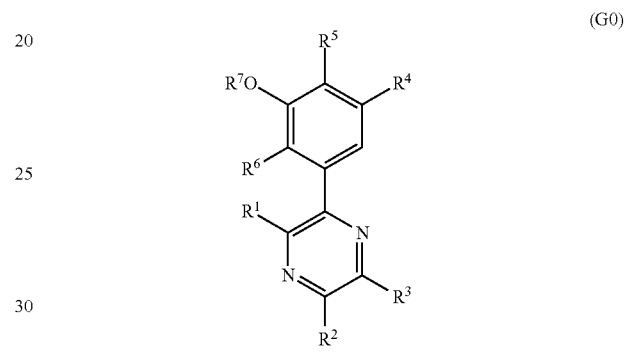

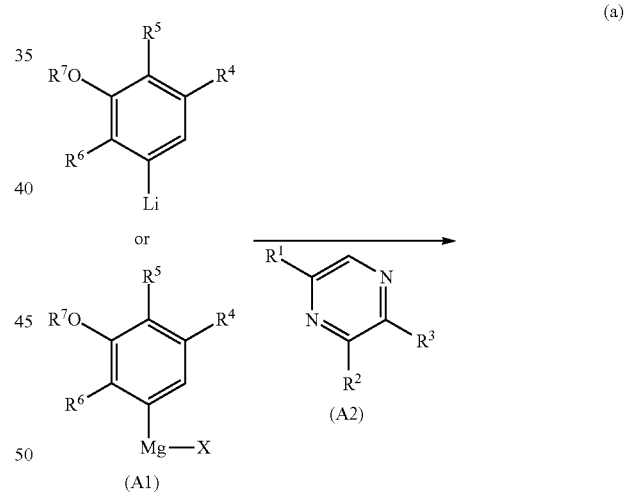

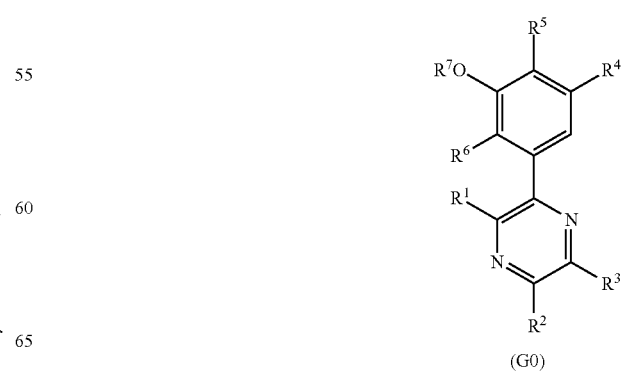

-continued

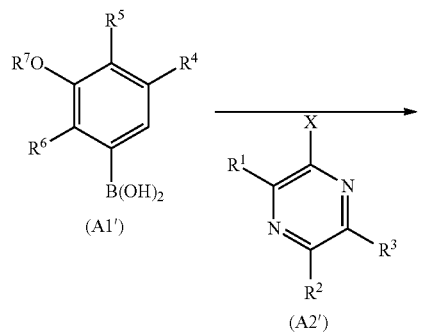

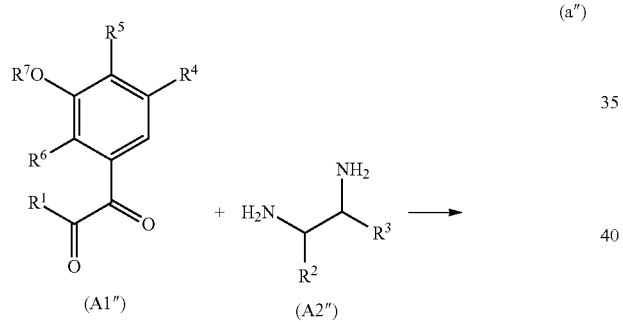

Since a variety of kinds of the above compounds (A1), (A2), (A1'), (A2'), (A1"), and (A2") are commercially available or can be synthesized, many kinds of meta-alkoxyphenyl pyrazine derivatives represented by General Formula (G0) can be synthesized. Therefore, there are wide variations of ligands for the organometallic complex which is one embodiment of the present invention.

<<Synthesis Method of Organometallic Complexes, Each of which is One Embodiment of the Present Invention, Represented by General Formula (G4) and General Formula (G7)>>

Next, an organometallic complex represented by General Formula (G4) below and an organometallic complex represented by General Formula (G7) below will be described which are specific preferable examples of an organometallic complex of one embodiment of the present invention which is formed by ortho-metallation of the m-alkoxyphenyl pyrazine derivative represented by General Formula (G0), that is, an organometallic complex having a structure represented by General Formula (G1) below.

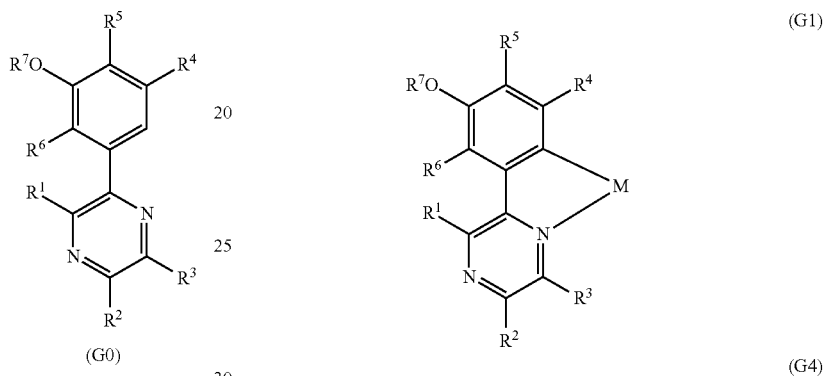

First, as shown in Synthesis Scheme (b) below, the m-alkoxyphenyl pyrazine derivative represented by General Formula (G0) and a compound of a metal belonging to Group 9 or Group 10 which contains halogen (a metal halide or a metal complex) are heated with an alcohol solvent (e.g., glycerol, ethyleneglycol, 2-methoxyethanol, or 2-ethoxyethanol) alone or a mixed solvent of water and one or more kinds of the above alcohol solvents, whereby a binuclear complex (B), which is a kind of organometallic complexes having the structure represented by General Formula (G1), can be obtained.

As the compound of a metal belonging to Group 9 or Group 10, which contains halogen, rhodium chloride hydrate, palladium chloride, iridium chloride hydrate, iridium chloride hydrochloride hydrate, potassium tetrachloroplatinate(II), and the like are given; however, the present invention is not limited to these examples. Note that in Synthesis Scheme (b) below, M represents an element belonging to Group 9 or Group 10, and X represents a halogen element. In addition, n is 2 when M is an element belonging to Group 9, and n is 1 when M is an element belonging to Group 10.

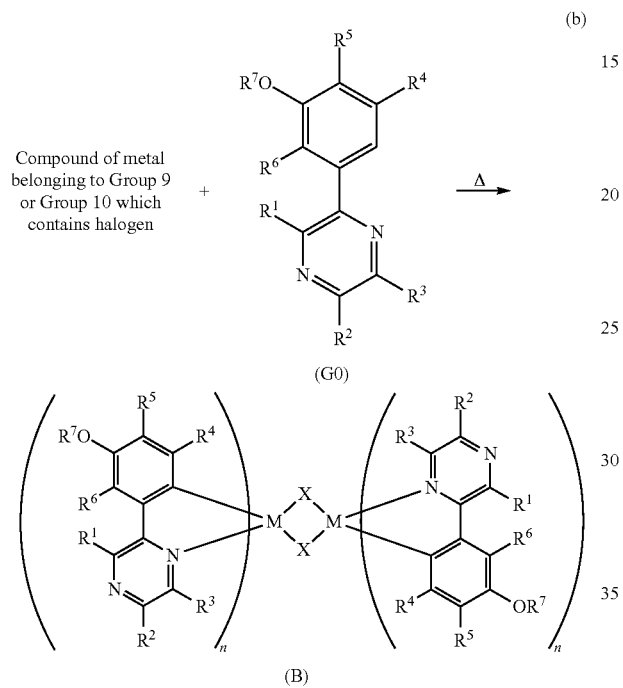

(b)

(G0)

(B)

Furthermore, as represented by Synthesis Scheme (c) below, the dinuclear complex (B) obtained by above Synthesis Scheme (b) and HL that is a material of a monoanionic ligand are reacted, whereby a proton of HL is eliminated to be coordinated to the central metal M, giving the organometallic complex which is one embodiment of the present invention, which is represented by General Formula (G4). Note that, in Synthesis Scheme (c), M represents an element belonging to Group 9 or Group 10, and X represents a halogen element. In addition, n is 2 when M is an element belonging to Group 9, and n is 1 when M is an element belonging to Group 10.

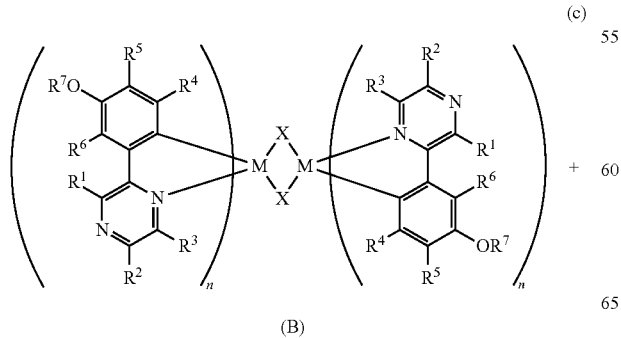

(c)

(B)

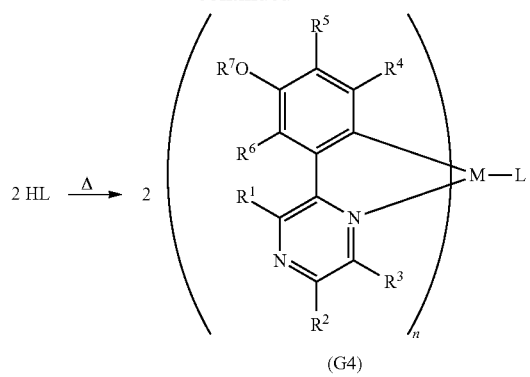

(G4)

Note that, in General Formula (G4), $R^1$ represents any of an alkyl group having 1 to 4 carbon atoms, an alkoxy group having 1 to 4 carbon atoms, or an alkoxycarbonyl group having 1 to 5 carbon atoms. Each of $R^2$ and $R^3$ represents either hydrogen or an alkyl group having 1 to 4 carbon atoms. In addition, each of $R^4$, $R^5$, and $R^6$ represents any of hydrogen, an alkyl group having 1 to 4 carbon atoms, an alkoxy group having 1 to 4 carbon atoms, a halogen group, a trifluoromethyl group, or an aryl group having 6 to 12 carbon atoms. In addition, $R^7$ represents either a straight-chain alkyl group having 1 to 4 carbon atoms or a branched-chain alkyl group having 1 to 4 carbon atoms. Note that the alkyl group may be substituted with a phenyl group. M is a central metal and represents either an element belonging to Group 9 or an element belonging to Group 10. L represents a monoanionic ligand. Moreover, n is 2 when M is an element belonging to Group 9, and n is 1 when M is an element belonging to Group 10.

The monoanionic ligand (L) in General Formula (G4) is any of a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen.

Further, the monoanionic ligand (L) in General Formula (G4) is represented by any of Structural Formulae (L1) to (L8) below.

(L1)

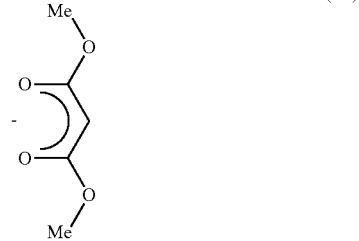

(L2)

-continued (L3)
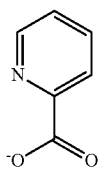

(L4)
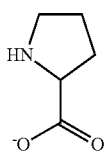

(L5)
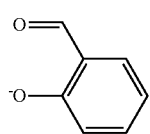

(L6)
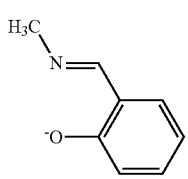

(L7)
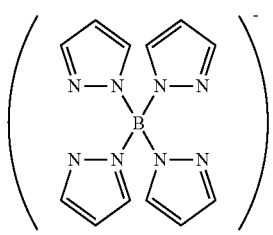

(L8)
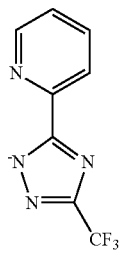

The organometallic complex of one embodiment of the present invention, which is represented by above General Formula (G7), can be synthesized by Synthesis Scheme (d) below. In other words, the organometallic complex can be obtained by heating the organometallic complex represented by General Formula (G4) which is obtained by above Synthesis Scheme (c) and the m-alkoxyphenyl pyrazine derivative represented by General Formula (G0) in a high boiling solvent such as glycerin at a high temperature of about 200° C. Note that, in Synthesis Scheme (d), M represents an element belonging to Group 9 or Group 10, and X represents a halogen element. In addition, n is 2 when M is an element belonging to Group 9, and n is 1 when M is an element belonging to Group 10.

(d)

(G4)

(G0)

(G7)

Note that, in General Formula (G7), $R^1$ represents any of an alkyl group having 1 to 4 carbon atoms, an alkoxy group having 1 to 4 carbon atoms, or an alkoxycarbonyl group having 1 to 5 carbon atoms. Each of $R^2$ and $R^3$ represents either hydrogen or an alkyl group having 1 to 4 carbon atoms. In addition, each of $R^4$, $R^5$, and $R^6$ represents any of hydrogen, an alkyl group having 1 to 4 carbon atoms, an alkoxy group having 1 to 4 carbon atoms, a halogen group, a trifluoromethyl group, or an aryl group having 6 to 12 carbon atoms. In addition, $R^7$ represents either a straight-chain alkyl group having 1 to 4 carbon atoms or a branched-chain alkyl group having 1 to 4 carbon atoms. Note that the alkyl group may be substituted with a phenyl group. M is a central metal and represents either an element belonging to Group 9 or an element belonging to Group 10. Moreover, n is 2 when M is an element belonging to Group 9, and n is 1 when M is an element belonging to Group 10.

The organometallic complex which is one embodiment of the present invention is formed by use of the central metal M and the monoanionic ligand L described above in combination as appropriate. Hereinafter, specific structural formulae of organometallic complexes each of which is one embodiment of the present invention are given (Structural Formulae (100) to (147) below). However, the present invention is not limited thereto.
(100)
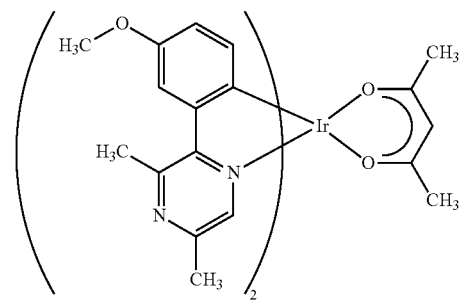
(101)
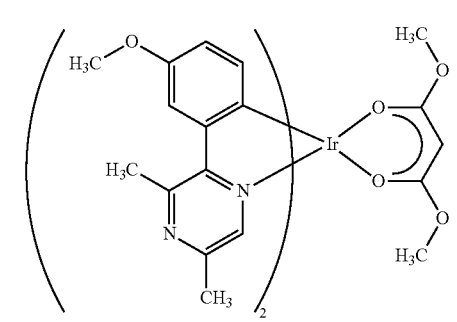
(102)
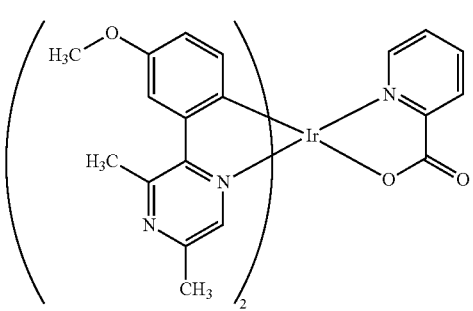
(103)
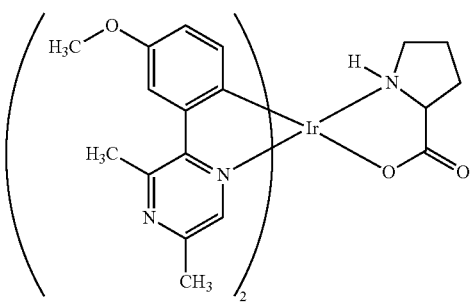
(104)
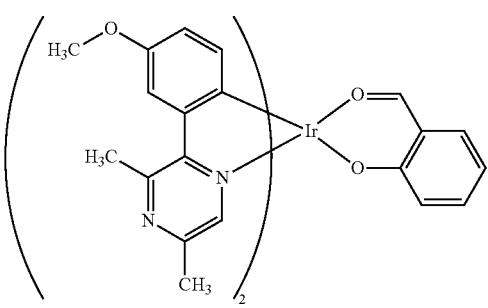
-continued
(105)
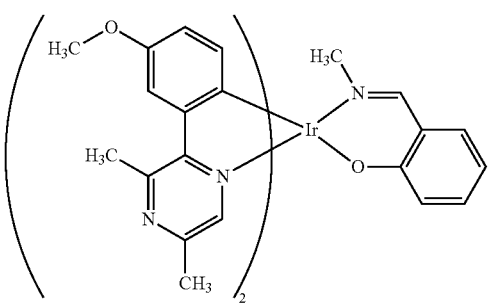
(106)
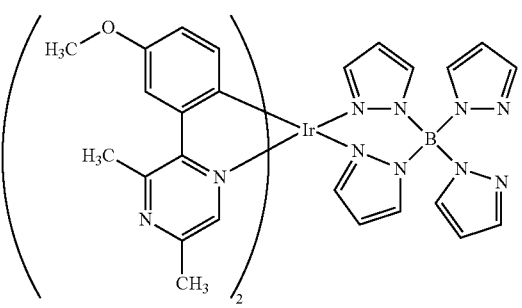
(107)
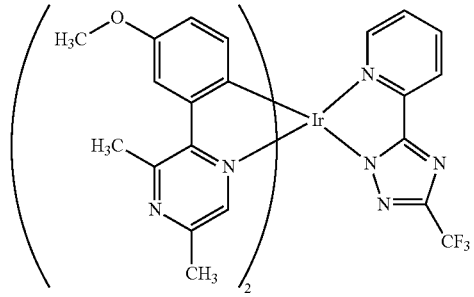
(108)
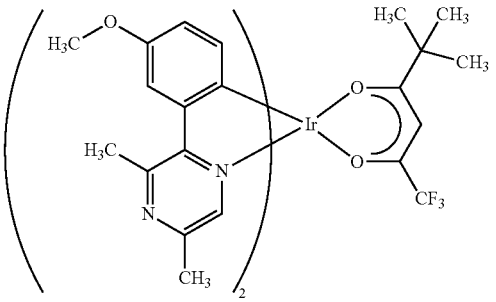
(109)
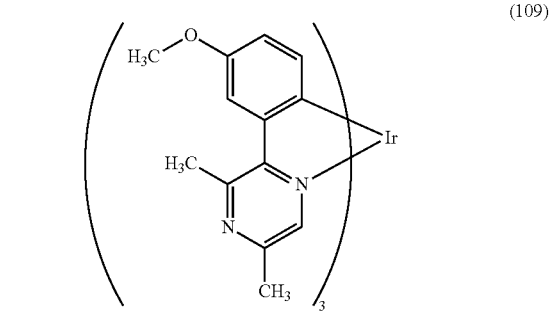

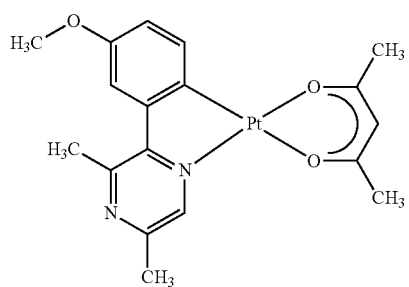
(110)
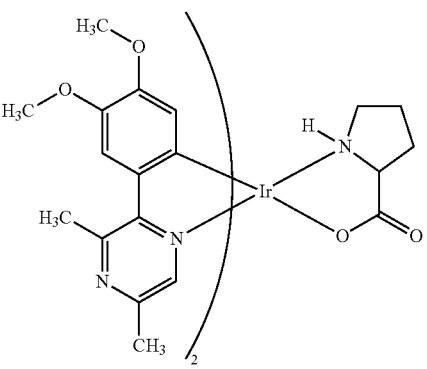
(114)
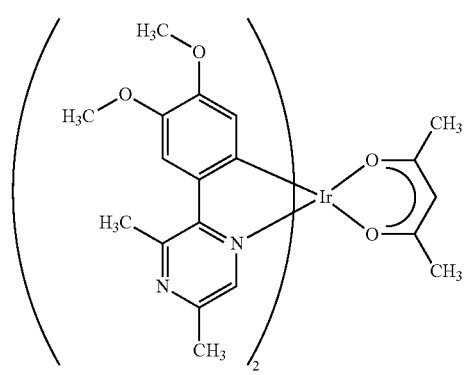
(111)
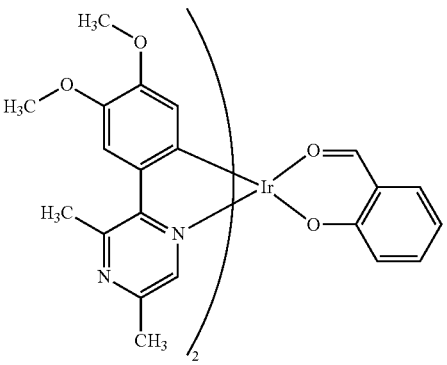
(115)
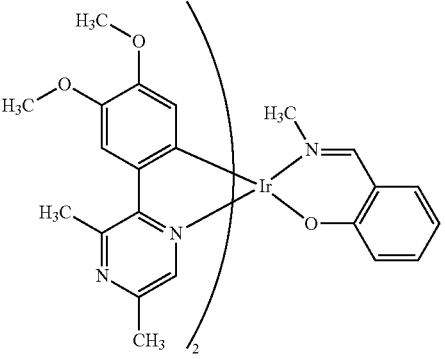
(112)
(116)
(113)
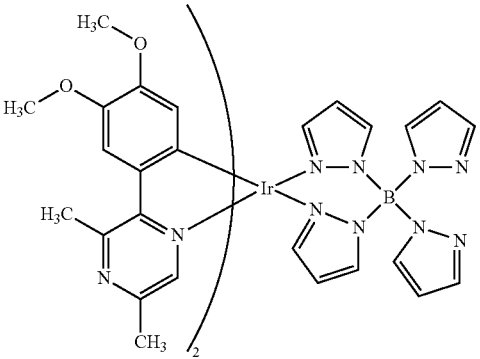
(117)

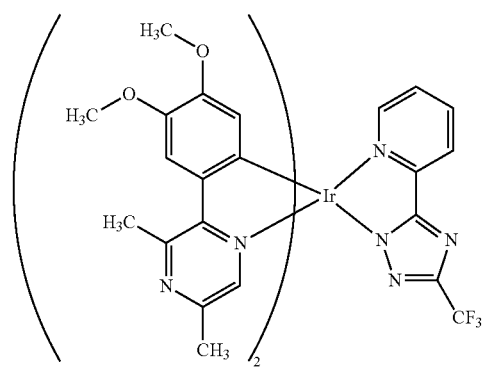
(118)
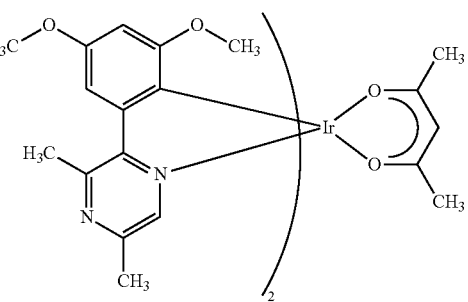
(122)
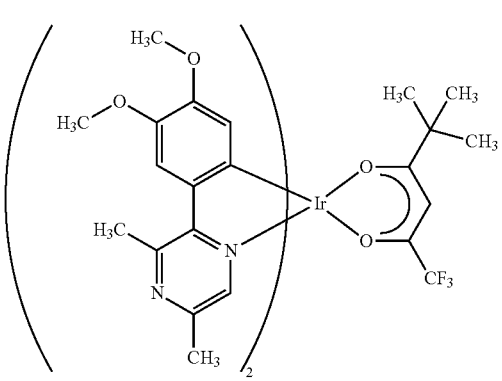
(119)
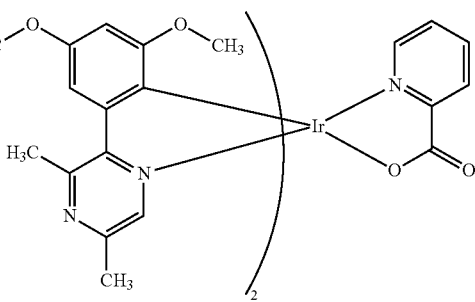
(123)
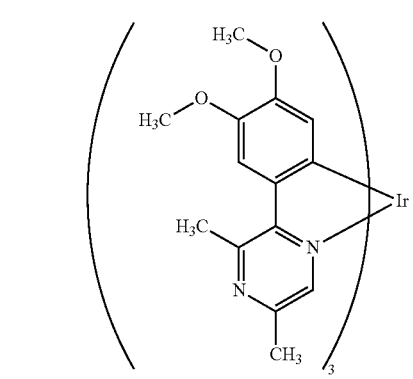
(120)
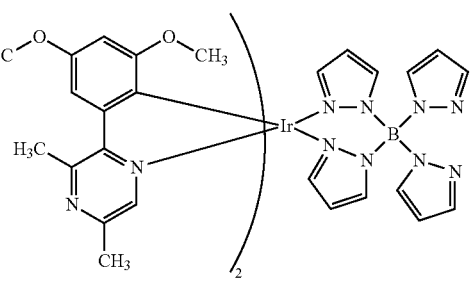
(124)
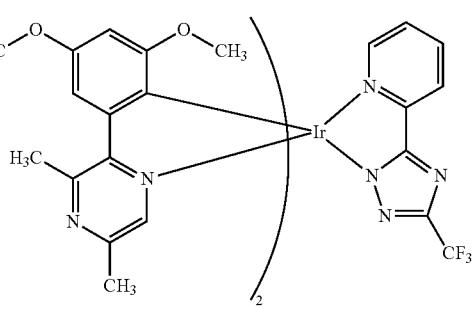
(125)
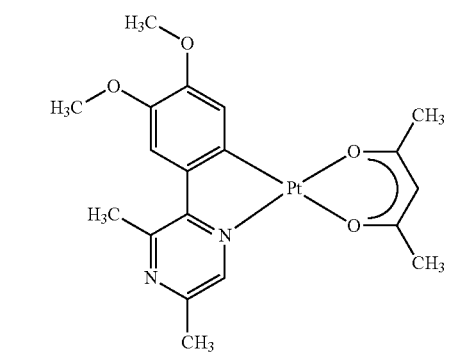
(121)
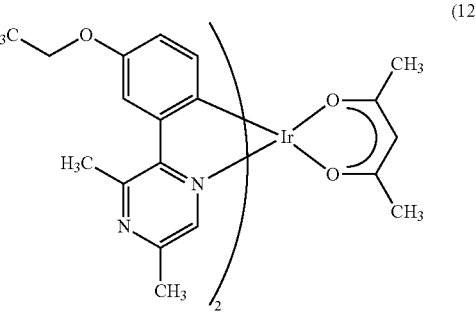
(126)

(127) 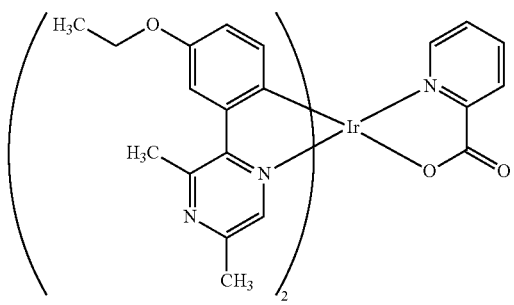
(128) 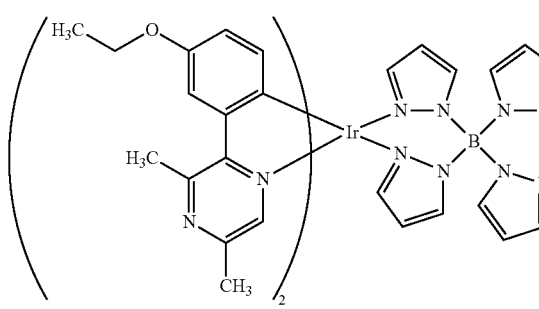
(129) 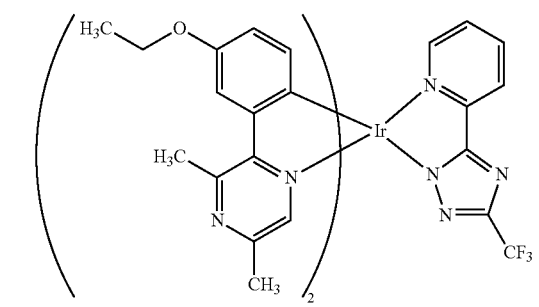
(130) 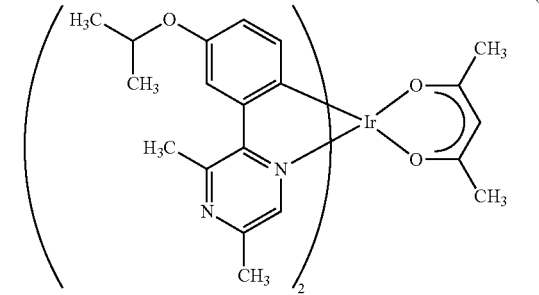
(131) 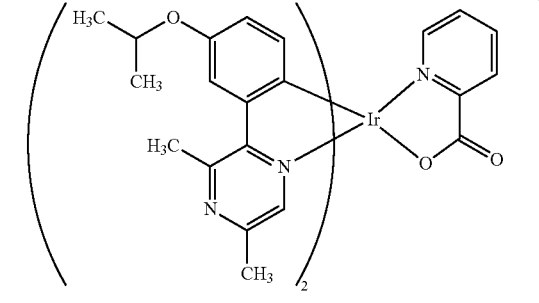
(132) 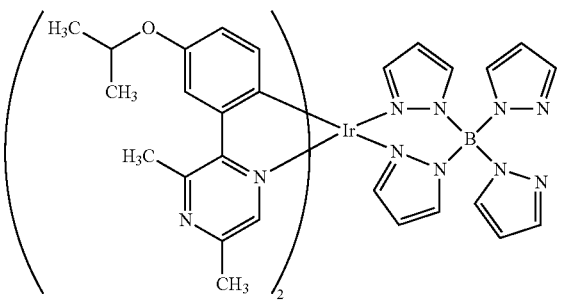
(133) 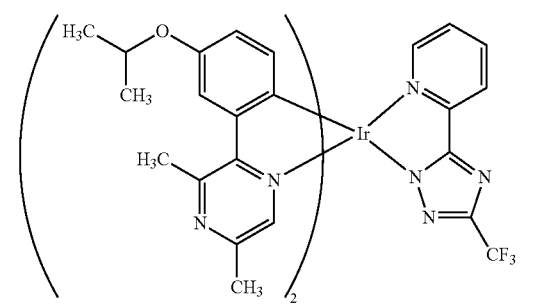
(134) 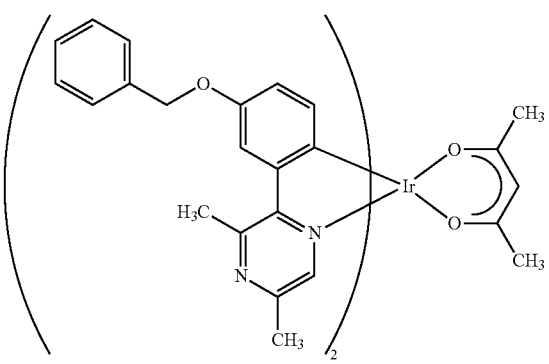
(135) 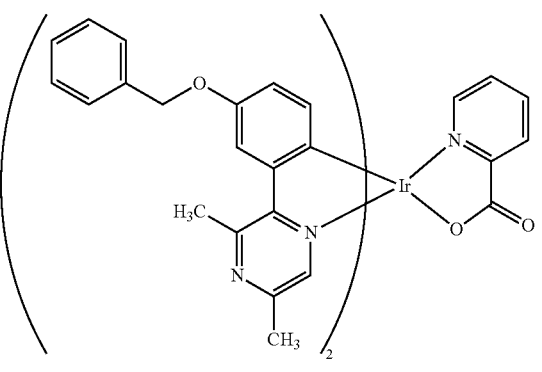

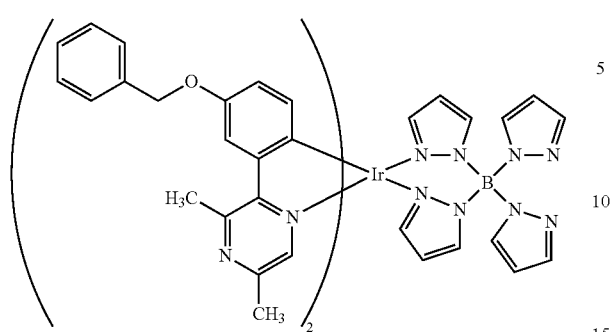
(136)
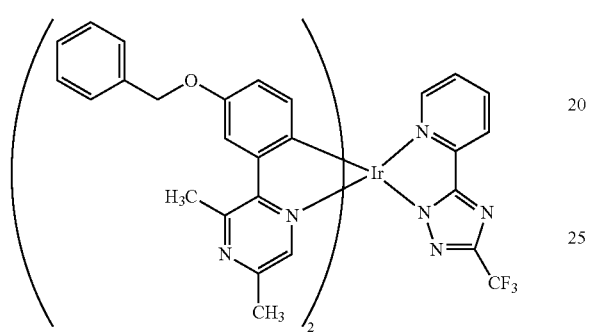
(137)
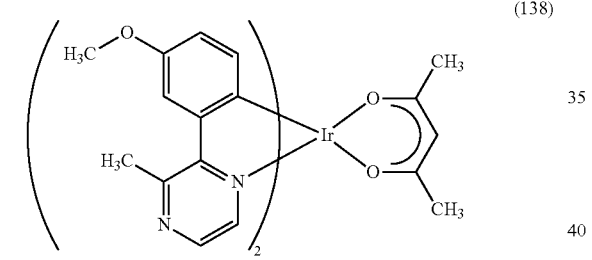
(138)
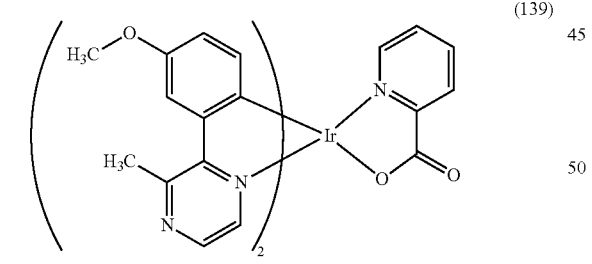
(139)
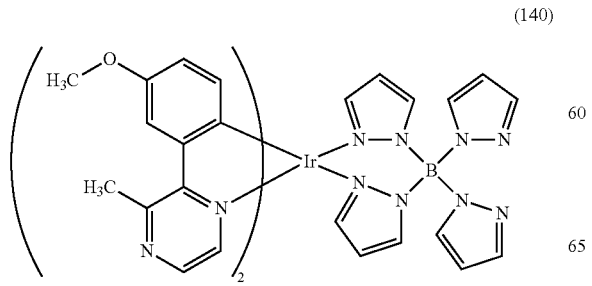
(140)
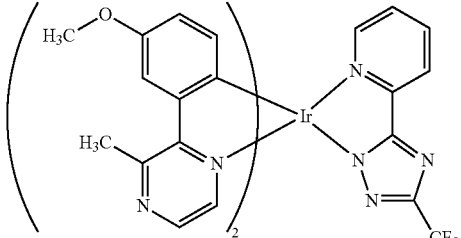
(141)
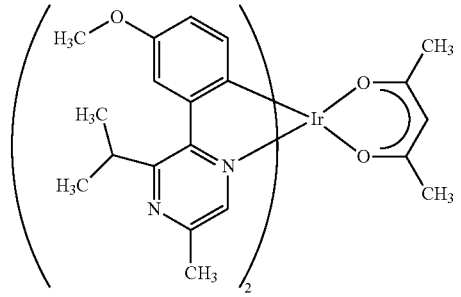
(142)
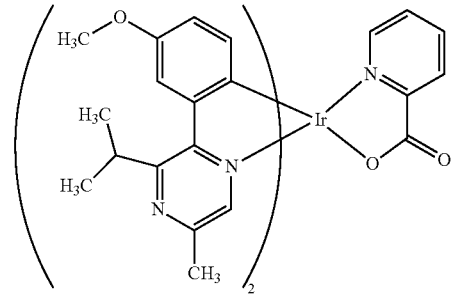
(143)
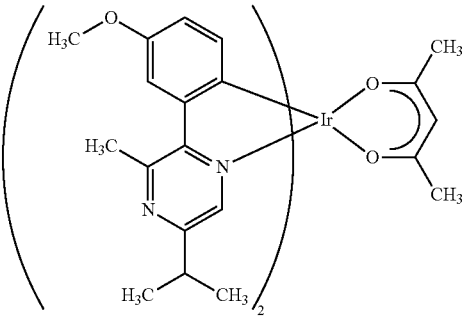
(144)
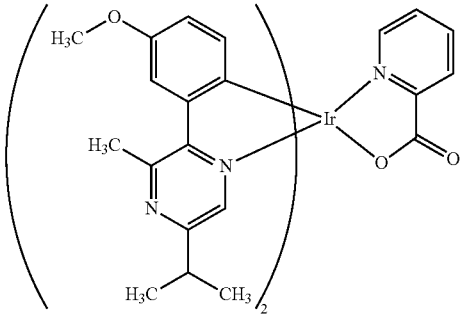
(145)

-continued (146)

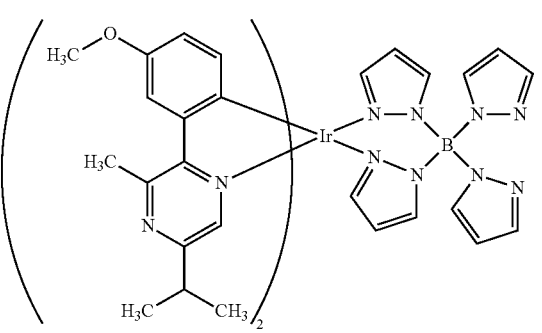

(147)

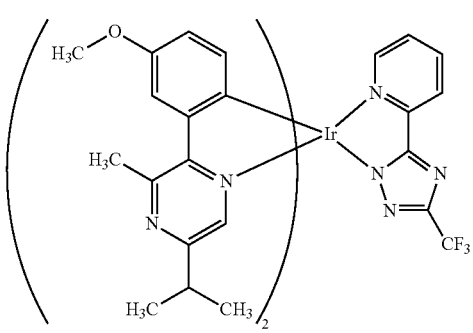

-continued (ii)

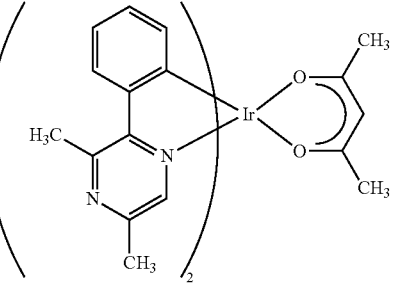

Ir(mppr-Me)₂acac (100)

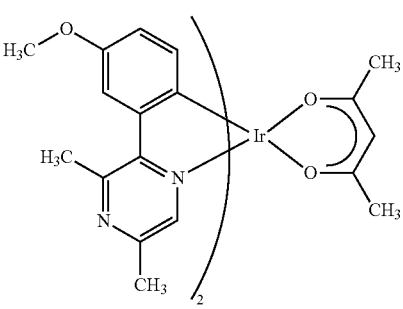

Ir(dm5moppr)₂acac

Note that stereoisomers which can exist in each of the organometallic complexes represented by above Structural Formulae (100) to (147) depends on the type of ligand. The organometallic complex which is one embodiment of the present invention includes all of these isomers.

Further, the above-described organometallic complexes each of which is one embodiment of the present invention can be used as a photosensitizer owing to its capability of intersystem crossing. In addition, the organometallic complexes are capable of emitting phosphorescence, and therefore can be used as a light-emitting material or a light-emitting substance for a light-emitting element.

Here, the calculation results indicating that the organometallic complex which is one embodiment of the present invention is capable of emitting red phosphorescence owing to its structure are shown.

The structures of the organometallic complexes used for the calculation are represented by Structural Formulae (i), (ii), and (100).

(i)

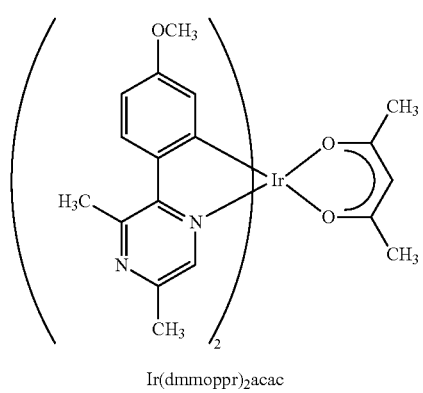

Ir(dmmoppr)₂acac

Note that [Ir(dmmoppr)₂(acac)] that is a comparative example is represented by Structural Formula (I), [Ir(mppr-Me)₂(acac)] that is a comparative example is represented by Structural Formula (II), and [Ir(dm5moppr)₂(acac)] that is an organometallic complex of one embodiment of the present invention is represented by Structural Formula (100).

First, the most stable structures of molecules represented by Structural Formulae (i), (ii), and (100) in a triplet state were calculated by using a density functional theory. The quantum chemistry computational program used here is Gaussian 03. As a basis function, 6-311G(d,p) was used for H, C, N, and O atoms, and LanL2DZ was used for Ir atoms. As a functional, B3PW91 was used.

Next, excitation energy of the molecules represented by Structural Formulae (i), (ii), and (100) was calculated by using the most stable structures in the triplet state, which were obtained by the above calculation, by using a time-dependent density functional theory. The basis function and functional used for this calculation were the same as those described above.

Table 1 shows the results of the first excitation energy in the triplet state obtained by the above calculation of the excitation energy.

TABLE 1

| | Ir(dmmoppr)₂(acac) | Ir(mppr-Me)₂(acac) | Ir(dm5moppr)₂(acac) |
|---|---|---|---|
| First excitation energy in the triplet state | 1.92 eV | 1.89 eV | 1.64 eV |

The calculation results indicate that when the meta position is substituted with an alkoxy group, the excitation energy is decreased, resulting in the shift of emission wavelength toward a longer wavelength side. Thus, the calculation results indicate that the organometallic complex of one embodiment of the present invention, which is formed by ortho-metallation of the m-alkoxyphenyl pyrazine derivative with respect to ions of metal belonging to Group 9 or Group 10, exhibits particularly dark red phosphorescent emission due to having the alkoxy group at the meta position.

Embodiment 2

In this embodiment, as one embodiment of the present invention, a light-emitting element in which an organometallic complex is used for a light-emitting layer will be described with reference to FIG. 1.

FIG. 1 illustrates a light-emitting element in which an EL layer 102 including a light-emitting layer 113 is interposed between a first electrode 101 and a second electrode 103. The light-emitting layer 113 contains the organometallic complex which is one embodiment of the present invention, which has been described in Embodiment 1.

By application of a voltage to such a light-emitting element, holes injected from the first electrode 101 side and electrons injected from the second electrode 103 side recombine in the light-emitting layer 113 to bring the organometallic complex into an excited state. Light is emitted when the organometallic complex in the excited state returns to the ground state. Thus, the organometallic complex which is one embodiment of the present invention functions as a light-emitting substance in the light-emitting element. Note that, in the light-emitting element described in this embodiment, the first electrode 101 functions as an anode and the second electrode 103 functions as a cathode.

When the first electrode 101 functions as an anode, it is preferably formed using a metal, an alloy, an electrically-conductive compound, a mixture thereof, or the like each having a high work function (specifically, a work function of 4.0 eV or higher). Specifically, for example, indium tin oxide (ITO), indium tin oxide containing silicon or silicon oxide, indium zinc oxide (IZO), indium oxide containing tungsten oxide and zinc oxide, and the like can be given. Other than the above, gold (Au), platinum (Pt), nickel (Ni), tungsten (W), chromium (Cr), molybdenum (Mo), iron (Fe), cobalt (Co), copper (Cu), palladium (Pd), titanium (Ti), or the like can be used.

Note that, in the case where in the EL layer 102, a layer formed in contact with the first electrode 101 is formed using a composite material in which an organic compound and an electron acceptor (acceptor) which are described later are mixed, the first electrode 101 can be formed using any of various types of metals, alloys, and electrically-conductive compounds, a mixture thereof, and the like regardless of the work function. For example, aluminum (Al), silver (Ag), an alloy containing aluminum (e.g., Al—Si), or the like can be used.

Note that the first electrode 101 can be formed by, for example, a sputtering method, an evaporation method (e.g., a vacuum evaporation method), or the like.

The EL layer 102 formed over the first electrode 101 includes at least the light-emitting layer 113 and is formed by containing an organometallic complex which is one embodiment of the present invention. For part of the EL layer 102, a known substance can be used, and either a low molecular compound or a high molecular compound can be used. Note that the substance used for forming the EL layer 102 may have not only a structure formed of only an organic compound but also a structure in which an inorganic compound is partially contained.

Further, as illustrated in FIG. 1, the EL layer 102 is formed by stacking as appropriate a hole-injecting layer 111 containing a substance having a high hole-transporting property, a hole-transporting layer 112 containing a substance having a high hole-transporting property, an electron-transporting layer 114 containing a substance having a high electron-transporting property, an electron-injecting layer 115 containing a substance having a high electron-injecting property, and the like in addition to the light-emitting layer 113.

The hole-injecting layer 111 is a layer containing a substance having a high hole-injecting property. As the substance having a high hole-injecting property, metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. Alternatively, a phthalocyanine compound such as phthalocyanine (abbreviation: $H_2Pc$), copper(II) phthalocyanine (abbreviation: CuPc), or vanadyl phthalocyanine (abbreviation: VOPc) can be used.

Alternatively, the following aromatic amine compounds which are low molecular organic compounds can be used: 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphtyl)-N-(9-phenylcarbazol-3-yl)amino]-9-phenylcarbazole (abbreviation: PCzPCN1), or the like.

Further alternatively, a high molecular compound (e.g., an oligomer, a dendrimer, or a polymer) can be used. For example, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine (abbreviation: poly-TPD) can be given. Further alternatively, a high molecular compound doped with acid, such as poly(3,4-ethylenedioxythiophene)/poly(styrenesulfonic acid) (PEDOT/PSS) or polyanline/poly(styrenesulfonic acid) (PAni/PSS) can be used.

A composite material in which an organic compound and an electron acceptor (acceptor) are mixed may be used for the hole-injecting layer 111. Such a composite material is excellent in a hole-injecting property and a hole-transporting property because holes are generated in the organic compound by the electron acceptor. In this case, the organic compound is preferably a material excellent in transporting the generated holes (a substance having a high hole-transporting property).

As the organic compound used for the composite material, a variety of compounds such as an aromatic amine compound, a carbazole derivative, an aromatic hydrocarbon, and a high molecular compound (e.g., an oligomer, a dendrimer, or a polymer) can be used. Note that the organic compound used for the composite material preferably has a high hole-transporting property. Specifically, a substance having a hole mobility of $10^{-6}$ cm$^2$/Vs or higher is preferable. However, materials other than these may alternatively be used as long as they have a hole-transporting property higher than an electron-transporting property. Specific examples of the organic compound that can be used for the composite material will be given below.

As the organic compound that can be used for the composite material, for example, an aromatic amine compound such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), or N,N'-bis(3-methylphenyl)-N,N'-diphenyl-[1,1'-biphenyl]-4,4'-diamine (abbreviation: TPD); and a carbazole derivative such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), or 1,4-bis[4-(N-carbazolyl)phenyl]-2,3,5,6-tetraphenylbenzene can be used.

Alternatively, an aromatic hydrocarbon compound such as 2-tert-butyl-9,10-di(2-naphthyl)anthracene (t-BuDNA), 2-tert-butyl-9,10-di(1-naphthyl)anthracene, 9,10-bis(3,5-diphenylphenyl)anthracene (DPPA), 2-test-butyl-9,10-bis(4-phenylphenyl)anthracene (t-BuDBA), 9,10-di(2-naphthyl)anthracene (DNA), 9,10-diphenylanthracene (DPAnth), 2-tert-butylanthracene (t-BuAnth), 9,10-bis(4-methyl-1-naphthyl)anthracene (DMNA), 9,10-bis[2-(1-naphthyl)phenyl]-2-tert-butylanthracene, 9,10-bis[2-(1-naphthyl)phenyl]anthracene, or 2,3,6,7-tetramethyl-9,10-di(1-naphthyl)anthracene can be used.

Further alternatively, an aromatic hydrocarbon compound such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), or 9,10-bis[4-(2,2-diphenylvinyl)phenyl]anthracene (abbreviation: DPVPA) can be used.

Further, as the electron acceptor, organic compounds such as 7,7,8,8-tetracyano-2,3,5,6-tetrafluoroquinodimethane (abbreviation: $F_4$-TCNQ) and chloranil; and transition metal oxides can be given. In addition, oxides of metals belonging to Group 4 to Group 8 of the periodic table can also be given. Specifically, vanadium oxide, niobium oxide, tantalum oxide, chromium oxide, molybdenum oxide, tungsten oxide, manganese oxide, and rhenium oxide are preferable because they have a high electron-accepting property. Among the above, molybdenum oxide is especially preferable because it is stable in the air, has low hygroscopic property, and is easy to handle.

Note that the hole-injecting layer 111 may be formed using a composite material of the above-described high molecular compound, such as PVK, PVTPA, PTPDMA, or Poly-TPD, and the above-described electron acceptor.

The hole-transporting layer 112 is a layer containing a substance having a high hole-transporting property. As the substance having a high hole-transporting property, an aromatic amine compound such as NPB, TPD, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB) can be used. The materials described here are mainly materials having a hole mobility of $10^{-6}$ cm$^2$/Vs or higher. However, substances other than these can also be used as long as they have a hole-transporting property higher than an electron-transporting property. Note that the layer containing a substance having a high hole-transporting property is not limited to a single layer, and a stacked layer in which two or more layers containing the above-described substance are stacked may be used.

Alternatively, for the hole-transporting layer 112, a high molecular compound such as PVK, PVTPA, PTPDMA, or Poly-TPD can be used.

The light-emitting layer 113 is preferably a layer containing the organometallic complex which is one embodiment of the present invention, specifically, a layer containing, as a host, a substance which has a higher triplet excitation energy than the organometallic complex which is one embodiment of the present invention and the organometallic complex which is one embodiment of the present invention dispersed as a guest. Thus, quenching of light emission from the organometallic complex caused due to the concentration can be prevented. Note that the triplet excitation energy indicates an energy gap between a ground state and a triplet excited state.

Although there is no particular limitation on the substance used for dispersing any of the above-described organometallic complexes (i.e., a host), a carbazole derivative such as CBP or 4,4',4''-tris(N-carbazolyl)triphenylamine (abbreviation: TCTA); and a metal complex such as bis[2-(2-hydroxyphenyl)pyridinato]zinc (abbreviation: $Znpp_2$), bis[2-(2-hydroxyphenyl)benzoxazolato]zinc (abbreviation: ZnBOX), bis(2-methyl-8-quinolinolato)(4-phenylphenolato)aluminum (abbreviation: BAlq), or tris(8-quinolinolato)aluminum (abbreviation: $Alq_3$) are preferable in addition to a compound having an arylamine skeleton, such as 2,3-bis(4-diphenylaminophenyl)quinoxaline (abbreviation: TPAQn) or NPB. Alternatively, a high molecular compound such as PVK can be used.

The electron-transporting layer 114 is a layer containing a substance having a high electron-transporting property. For the electron-transporting layer 114, metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, Zn(BOX)$_2$, or bis[2-(2'-hydroxyphenyl)pyridinato]zinc (abbreviation: Zn(BTZ)$_2$) can be given. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-pyridine-6,6'-diyl)] (abbreviation: PF-BPy) can be used. The substances described here are mainly materials having an electron mobility of $10^{-6}$ cm$^2$/Vs or higher. Note that materials other than these may alternatively be used as long as they have an electron-transporting property higher than a hole-transporting property.

Further, the electron-transporting layer is not limited to a single layer, and a stacked layer in which two or more layers containing any of the above-described substances are stacked may be used.

The electron-injecting layer 115 is a layer containing a substance having a high electron-injecting property. For the electron-injecting layer 115, an alkali metal, an alkaline earth metal, or a compound thereof, such as lithium (Li), cesium (Cs), calcium (Ca), lithium fluoride (LiF), cesium fluoride (CsF), calcium fluoride (CaF$_2$), or lithium oxide (LiOx), can be used. Alternatively, a rare earth metal compound such as erbium fluoride (ErF$_3$) can be used. Further alternatively, the substances for forming the electron-transporting layer 114, which are described above, can be used.

Alternatively, a composite material in which an organic compound and an electron donor (donor) are mixed may be used for the electron-injecting layer 115. Such a composite material is excellent in an electron-injecting property and an electron-transporting property because electrons are generated in the organic compound by the electron donor. In this case, the organic compound is preferably a material excellent in transporting the generated electrons. Specifically, for example, the substances for forming the electron-transporting layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like are given. In addition, alkali metal oxide or alkaline earth metal oxide such as lithium oxide, calcium oxide, barium oxide, and the like can be given. Lewis base such as magnesium oxide can alternatively be used. An organic compound such as tetrathiafulvalene (abbreviation: TTF) can alternatively be used.

Note that each of the above-described hole-injecting layer 111, hole-transporting layer 112, light-emitting layer 113, electron-transporting layer 114, and electron-injecting layer 115 can be formed by a method such as an evaporation method (e.g., a vacuum evaporation method), an ink-jet method, or a coating method.

When the second electrode 103 functions as a cathode, it can be formed using a metal, an alloy, an electrically-conductive compound, a mixture thereof, or the like having a low work function (preferably, a work function of 3.8 eV or lower). Specifically, Al, silver, or the like can be used besides an element belonging to Group 1 or Group 2 of the periodic table, that is, an alkali metal such lithium (Li) or cesium (Cs) and an alkaline earth metal such as magnesium (Mg), calcium (Ca), or strontium (Sr); an alloy of the above metals (e.g., MgAg and AlLi); a rare earth metal such as europium (Eu) or ytterbium (Yb); an alloy of the above metals, or the like.

Note that, in the case where in the EL layer 102, a layer formed in contact with the second electrode 103 is formed using a composite material in which the organic compound and the electron donor (donor), which are described above, are mixed, a variety of conductive materials such as Al, Ag, ITO, and indium tin oxide containing silicon or silicon oxide can be used regardless of the work function.

Note that the second electrode 103 can be formed by a vacuum evaporation method or a sputtering method. Alternatively, in the case of using a silver paste or the like, a coating method, an ink-jet method, or the like can be used.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a property of transmitting visible light.

Note that by use of the light-emitting element described in this embodiment, a passive matrix light-emitting device or an active matrix light-emitting device in which the driving of the light-emitting element is controlled by a thin film transistor (TFT) can be manufactured.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that, in this embodiment, the organometallic complex of one embodiment of the present invention, which is used for the light-emitting layer 113, exhibits red emission with excellent color purity. Thus, a light-emitting element which exhibits red emission with excellent color purity can be obtained.

In this embodiment, the structure described in this embodiment can be combined with the structure described in Embodiment 1 as appropriate.

Embodiment 3

The light-emitting element which is one embodiment of the present invention may include a plurality of light-emitting layers. A plurality of light-emitting layers are provided and light is emitted from each of the light-emitting layers, whereby emission in which plural types of light are mixed can be obtained. Thus, white light can be obtained, for example. In this embodiment, an embodiment of a light-emitting element including a plurality of light-emitting layers will be described with reference to FIG. 2.

Figure 2:
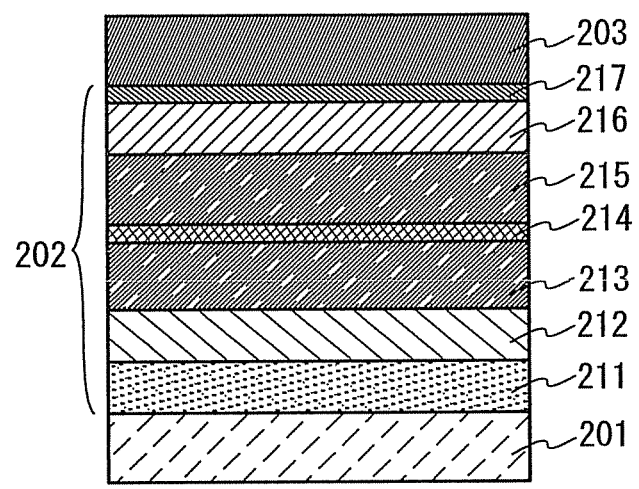
FIG. 2 is a view illustrating a light-emitting element which is one embodiment of the present invention.

In FIG. 2, an EL layer 202 including a first light-emitting layer 213 and a second light-emitting layer 215 is provided between a first electrode 201 and a second electrode 203. Emission in which light emitted from the first light-emitting layer 213 and light emitted from the second light-emitting layer 215 are mixed can be obtained. A separation layer 214 is preferably provided between the first light-emitting layer 213 and the second light-emitting layer 215.

When a voltage is applied so that the potential of the first electrode 201 is higher than the potential of the second electrode 203, current flows between the first electrode 201 and the second electrode 203, and holes and electrons recombine in the first light-emitting layer 213, the second light-emitting layer 215, or in the separation layer 214. Generated excitation energy is distributed to the first light-emitting layer 213 and the second light-emitting layer 215 to bring each of a first light-emitting substance contained in the first light-emitting layer 213 and a second light-emitting substance contained in the second light-emitting layer 215 into an excited state. The excited first and second light-emitting substances emit light when returning to the ground state.

The first light-emitting layer 213 contains the first light-emitting substance typified by a fluorescent compound such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, or bis(2-methyl-8-quinolinolato)galliumchloride (abbreviation: Gamq$_2$Cl); or a phosphorescent substance such as bis{2-[3,5-bis(trifluoromethyl)phenyl]pyridinato-N,C$^{2'}$}iridium(III)picolinate (abbreviation: Ir(CF$_3$ppy)$_2$(pic)), bis[2-(4,6-difluorophenyl)pyridinato-N,C$^{2'}$]iridium(III)acetylacetonate (abbreviation: FIr(acac)), bis[2-(4,6-difluorophenyl)pyridinato-N,C$^{2'}$]iridium(III)picolinate (abbreviation: FIrpic), or bis[2-(4,6-difluorophenyl)pyridinato-N,C$^{2'}$]iridium(III)tetra(1-pyrazolyl)borate (abbreviation: FIr6), from which emission having a peak at 450 nm to 510 nm in an emission spectrum (i.e., blue light to blue green light) can be obtained.

Further, in the case where the first light-emitting substance is a fluorescent compound, the first light-emitting layer 213 preferably has a structure in which a substance having a larger singlet excitation energy than the first light-emitting substance is used as a first host and the first light-emitting substance is dispersed as a guest. Further, in the case where the first light-emitting substance is a phosphorescent compound, the first light-emitting layer 213 preferably has a structure in which a substance having a higher triplet excitation energy than the first light-emitting substance is used as a first host and the first light-emitting substance is dispersed as a guest. As the first host, DNA, t-BuDNA, or the like can be used in addition to the above-described NPB, CBP, TCTA, and the like. Note that the singlet excitation energy is an energy difference between a ground state and a singlet excited state. In addition, the triplet excitation energy is an energy difference between a ground state and a triplet excited state.

On the other hand, the second light-emitting layer 215 contains the organometallic complex which is one embodiment of the present invention and can exhibit red emission. The second light-emitting layer 215 may have a similar structure to the light-emitting layer 113 described in Embodiment 2.

In addition, specifically, the separation layer 214 can be formed using TPAQn, NPB, CBP, TCTA, Znpp$_2$, ZnBOX, or the like described above. In this way, with provision of the separation layer 214, a defect that emission intensity of one of the first light-emitting layer 213 and the second light-emitting layer 215 is stronger than the other can be prevented. Note that the separation layer 214 is not necessarily provided, and it may be provided as appropriate such that the ratio in emission intensity of the first light-emitting layer 213 to the second light-emitting layer 215 can be adjusted.

Note that, in this embodiment, the organometallic complex which is one embodiment of the present invention is used for the second light-emitting layer 215 and another light-emitting substance is used for the first light-emitting layer 213, whereas the organometallic complex which is one embodiment of the present invention may be used for the first light-emitting layer 213 and another light-emitting substance may be used for the second light-emitting layer 215.

Further, the light-emitting element in which two light-emitting layers are provided as illustrated in FIG. 2 is described in this embodiment; however, the number of the light-emitting layers is not limited to two, and may be, for example, three. Emission from each light-emitting layer may be mixed. As a result, for example, white color emission can be obtained.

Note that the first electrode 201 may have a structure similar to that of the first electrode 101 described in Embodiment 2. In addition, the second electrode 203 may also have a structure similar to that of the second electrode 103 described in Embodiment 2.

Further, in this embodiment, as illustrated in FIG. 2, a hole-injecting layer 211, a hole-transporting layer 212, an electron-transporting layer 216, and an electron-injecting layer 217 are provided. As for structures of these layers, the structures of the respective layers described in Embodiment 2 may be applied. However, these layers are not necessarily provided and may be provided according to element characteristics.

Note that the structure described in this embodiment can be combined with the structure described in Embodiment 1 or 2 as appropriate.

Embodiment 4

Figure 3:
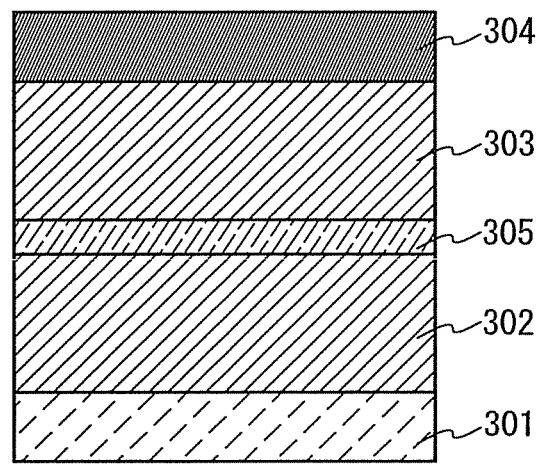
FIG. 3 is a view illustrating a light-emitting element which is one embodiment of the present invention.

In this embodiment, as one embodiment of the present invention, a structure of a light-emitting element in which a plurality of EL layers are included (hereinafter, such a light-emitting element is referred to as a stacked-type element) will be described with reference to FIG. 3. This light-emitting element is a stacked-type light-emitting element including a plurality of EL layers (a first EL layer 302 and a second EL layer 303) between a first electrode 301 and a second electrode 304. Note that, although the structure in which two EL layers are formed is described in this embodiment, a structure in which three or more EL layers are formed may be employed.

In this embodiment, the first electrode 301 functions as an anode, and the second electrode 304 functions as a cathode. Note that for the first electrode 301 and the second electrode 304, structures similar to those described in Embodiment 2 can be employed. In addition, although the plurality of EL layers (the first EL layer 302 and the second EL layer 303) may have structures similar to those described in Embodiment 2, any of the EL layers may have a structure similar to that described in Embodiment 2. In other words, the structures of the first EL layer 302 and the second EL layer 303 may be the same or different from each other and can be similar to those described in Embodiment 2.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In this embodiment, when a voltage is applied so that the potential of the first electrode 301 is higher than that of the second electrode 304, the charge generation layer 305 injects electrons into the first EL layer 302 and injects holes into the second EL layer 303.

Note that the charge generation layer 305 preferably has a property of transmitting visible light in terms of light extraction efficiency. Further, the charge generation layer 305 functions even if it has lower conductivity than the first electrode 301 or the second electrode 304.

The charge generation layer 305 may have either a structure in which an electron acceptor (acceptor) is added to an organic compound having a high hole-transporting property or a structure in which an electron donor (donor) is added to an organic compound having a high electron-transporting property. Alternatively, both of these structures may be stacked.

In the case of the structure in which an electron acceptor is added to an organic compound having a high hole-transporting property, as the organic compound having a high hole-transporting property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The materials described here are mainly materials having a hole mobility of $10^{-6}$ cm$^2$/Vs or higher. However, substances other than the above substances may be used as long as they are organic compounds having a hole-transporting property higher than an electron-transporting property.

Further, as the electron acceptor, 7,7,8,8-tetracyano-2,3,5,6-tetrafluoroquinodimethane (abbreviation: F$_4$-TCNQ), chloranil, and the like can be given. In addition, transition metal oxides can be given. Moreover, oxides of metals belonging to Groups 4 to 8 of the periodic table can be used. Specifically, vanadium oxide, niobium oxide, tantalum oxide, chromium oxide, molybdenum oxide, tungsten oxide, manganese oxide, and rhenium oxide are preferable because they have high electron-accepting properties. Among these, molybdenum oxide is especially preferable because it is stable in the air, has low hygroscopic property, and is easy to handle.

On the other hand, in the case of the structure in which an electron donor is added to an organic compound having a high electron-transporting property, as the organic compound having a high electron-transporting property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The materials described here are mainly materials having an electron mobility of $10^{-6}$ cm$^2$/Vs or higher. Note that substances other than the above substances may be used as long as they are organic compounds having an electron-transporting property higher than a hole-transporting property.

Further, as the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that by formation of the charge generation layer 305 using any of the above materials, an increase in the drive voltage in the case where the EL layers are stacked can be suppressed.

Although the light-emitting element having two EL layers has been described in this embodiment, the present invention can be similarly applied to a light-emitting element in which three or more EL layers are stacked. A plurality of EL layers are arranged to be separated from each other with a charge generation layer between a pair of electrodes, like the light-emitting element according to this embodiment, whereby an element having a long lifetime and high luminance can be achieved with current density kept low. When the light-emitting element is applied to a lighting device, a drop in voltage due to the resistance of an electrode material can be suppressed, and thus uniform emission in a large area can be achieved. Moreover, a light-emitting device which can be driven at a low voltage and has low power consumption can be achieved.

Further, when the EL layers have different emission colors, a desired emission color can be obtained from the whole light-emitting element. For example, in the light-emitting element having two EL layers, when an emission color of the first EL layer and an emission color of the second EL layer are made to be complementary colors, it is possible to obtain a light-emitting element from which white light is emitted from the whole light-emitting element. Note that "complementary color" refers to a relation between colors which become achromatic color by being mixed. In other words, white emission can be obtained by mixture of light obtained from substances whose emission colors are complementary colors.

Also in a light-emitting element having three EL layers, for example, white light can be similarly obtained from the whole light-emitting element when an emission color of a first EL layer is red, an emission color of a second EL layer is green, and an emission color of a third EL layer is blue.

Note that the structure described in this embodiment can be combined with any of the structures described in other embodiments as appropriate.

Embodiment 5

In this embodiment, as one embodiment of the present invention, an embodiment of a light-emitting element in which an organometallic complex is used as a sensitizer will be described with reference to FIG. 1.

FIG. 1 illustrates the light-emitting element in which the EL layer 102 including the light-emitting layer 113 is interposed between the first electrode 101 and the second electrode 103. The light-emitting layer 113 contains the organometallic complex which is one embodiment of the present invention and a fluorescent compound which can emit light with a longer wavelength than that of the light emitted from this organometallic complex.

In such a light-emitting element, holes injected from the first electrode 101 and electrons injected from the second electrode 103 side recombine in the light-emitting layer 113 to bring the fluorescent compound into an excited state. Light is emitted when the fluorescent compound in the excited state returns to the ground state. In this case, the organometallic complex which is one embodiment of the present invention acts as a sensitizer for the fluorescent compound to increase the number of molecules of the fluorescent compound in the singlet excited state. As described above, the organometallic complex of the present invention is used as a sensitizer, whereby a light-emitting element with good emission efficiency can be obtained. Note that in the light-emitting element of this embodiment, the first electrode 101 functions as an anode and the second electrode 103 function as a cathode.

The light-emitting layer 113 contains the organometallic complex which is one embodiment of the present invention and the fluorescent compound which can emit light with a longer wavelength than this organometallic complex. The light-emitting layer 113 may have a structure in which a substance having a larger singlet excitation energy than the fluorescent substance as well as a higher triplet excitation energy than the organometallic complex is used as a host, and the organometallic complex and the fluorescent compound are dispersed as a guest.

Note that there is no particular limitation on the substance used for dispersing the organometallic complex and the fluorescent compound (i.e., host), and the substances given as examples of the host in Embodiment 2, or the like can be used.

Further, although there is also no particular limitation on the fluorescent compound, a compound which can exhibit emission of red light to red infrared light, such as 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, or phthalocyanine, or the like is preferable.

Note that the first electrode 101 and the second electrode 103 described in this embodiment may have structures similar to those of the first electrode and the second electrode described in Embodiment 2, respectively.

Further, the hole-injecting layer 111, the hole-transporting layer 112, the electron-transporting layer 114, and the electron-injecting layer 115 are provided as illustrated in FIG. 1 in this embodiment, and as for structures of these layers, the structures of the respective layers described in Embodiment 2 may be applied. However, these layers are not necessarily provided and may be provided according to element characteristics.

The above-described light-emitting element can emit light with high efficiency by use of the organometallic complex which is one embodiment of the present invention as a sensitizer.

Note that the structure described in this embodiment can be combined with any of the structures described in Embodiments 1 to 4 as appropriate.

Embodiment 6

In this embodiment, as one embodiment of the present invention, a passive matrix light-emitting device and an active matrix light-emitting device each of which is a light-emitting device manufactured using a light-emitting element will be described.

FIGS. 4A to 4D and FIG. 5 illustrate examples of passive matrix light-emitting devices.

In a passive-matrix (also referred to as "simple-matrix") light-emitting device, a plurality of anodes arranged in stripes (in strip form) are provided to be perpendicular to a plurality of cathodes arranged in stripes, and a light-emitting layer is interposed at each intersection. Thus, a pixel at an intersection of an anode selected (to which a voltage is applied) and a cathode selected emits light.

Figure 4A:
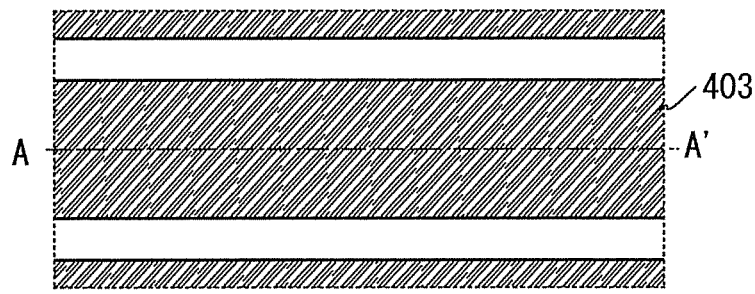
FIGS. 4A to 4D are views illustrating a passive matrix light-emitting device.
Figure 4B:
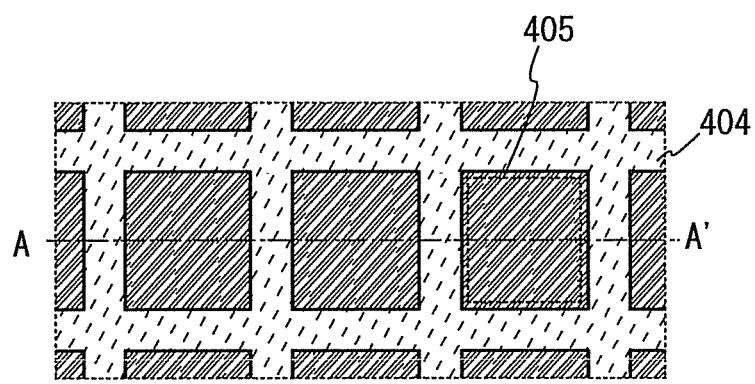
Figure 4C:
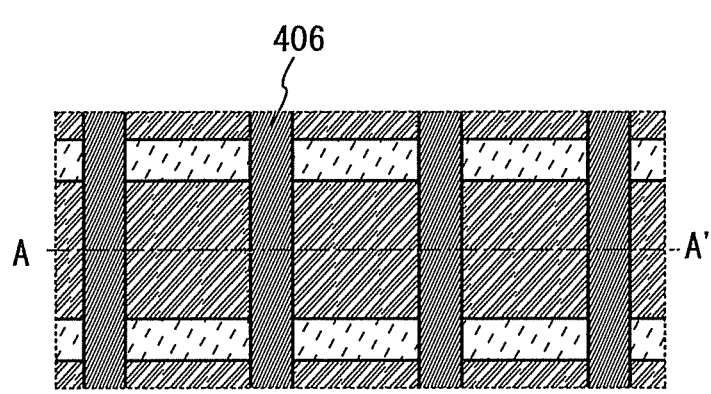
Figure 4D:
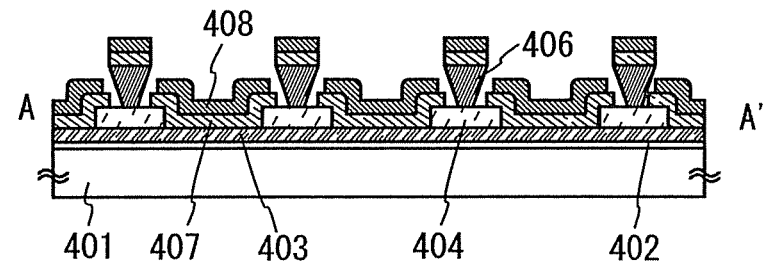

FIGS. 4A to 4C are top views illustrating a pixel portion before sealing. FIG. 4D is a cross-sectional view taken along the chain line A-A' in FIGS. 4A to 4C.

An insulating layer 402 is formed as a base insulating layer over a substrate 401. Note that the insulating layer 402 is not necessarily formed if the base insulating layer is not needed. A plurality of first electrodes 403 are arranged in stripes at regular intervals over the insulating layer 402 (FIG. 4A).

In addition, a partition wall 404 having openings each corresponding to a pixel is provided over the first electrodes 403. The partition wall 404 having the openings is formed of an insulating material (a photosensitive or nonphotosensitive organic material (e.g., polyimide, acrylic, polyamide, polyimide amide, resist, or benzocyclobutene) or an SOG film (e.g., a $SiO_x$ film containing an alkyl group). Note that the openings each corresponding to a pixel serve as light-emitting regions (FIG. 4B).

A plurality of inversely-tapered partition walls 406 parallel to each other are provided over the partition wall 404 having the openings to intersect with the first electrodes 403 (FIG. 4C). The inversely-tapered partition walls 1522 are formed by a photolithography method using a positive-type photosensitive resin, portion of which unexposed to light remains as a pattern, and by adjustment of the amount of light exposure or the length of development time so that a lower portion of a pattern is etched more.

After the inversely-tapered partition walls 406 are formed as illustrated in FIG. 4C, EL layers 407 and second electrodes 408 are sequentially formed as illustrated in FIG. 4D. The total thickness of the partition wall 404 having the openings and the inversely-tapered partition wall 406 is set to be larger than the total thickness of the EL layer 407 and the second electrode 408; thus, as illustrated in FIG. 4D, EL layers 407 and second electrodes 408 which are separated for plural regions are formed. Note that the plurality of separated regions are electrically isolated from one another.

The second electrodes 408 are electrodes in stripe form that are parallel to each other and extend along a direction intersecting with the first electrodes 403. Note that a plurality of stacked layers each including the EL layer 407 and part of conductive layer forming the second electrode 408 are also formed over the inversely-tapered partition walls 406; however, they are separated from the EL layer 407 and the second electrode 408.

Note that there is no particular limitation on the first electrode 403 and the second electrode 408 in this embodiment as long as one of them is an anode and the other is a cathode.

Note that a stacked structure in which the EL layer 407 is included may be adjusted as appropriate in accordance with the polarity of the electrode.

Further, if necessary, a sealing material such as a sealing can or a glass substrate may be attached to the substrate 401 for sealing with an adhesive such as a sealant, so that the light-emitting element is placed in the sealed space. This can prevents deterioration of the light-emitting element. Note that the sealed space may be filled with a filler or a dry inert gas. Furthermore, a desiccant or the like may be put between the substrate and the sealant in order to prevent deterioration of the light-emitting element due to moisture. The desiccant removes a minute amount of moisture, thereby achieving sufficient desiccation. The desiccant may be a substance which absorbs moisture by chemical adsorption, such as an oxide of an alkaline earth metal as typified by calcium oxide or barium oxide. Alternatively, the desiccant may be a substance which adsorbs moisture by physical adsorption such as zeolite or silica gel.

Figure 5:
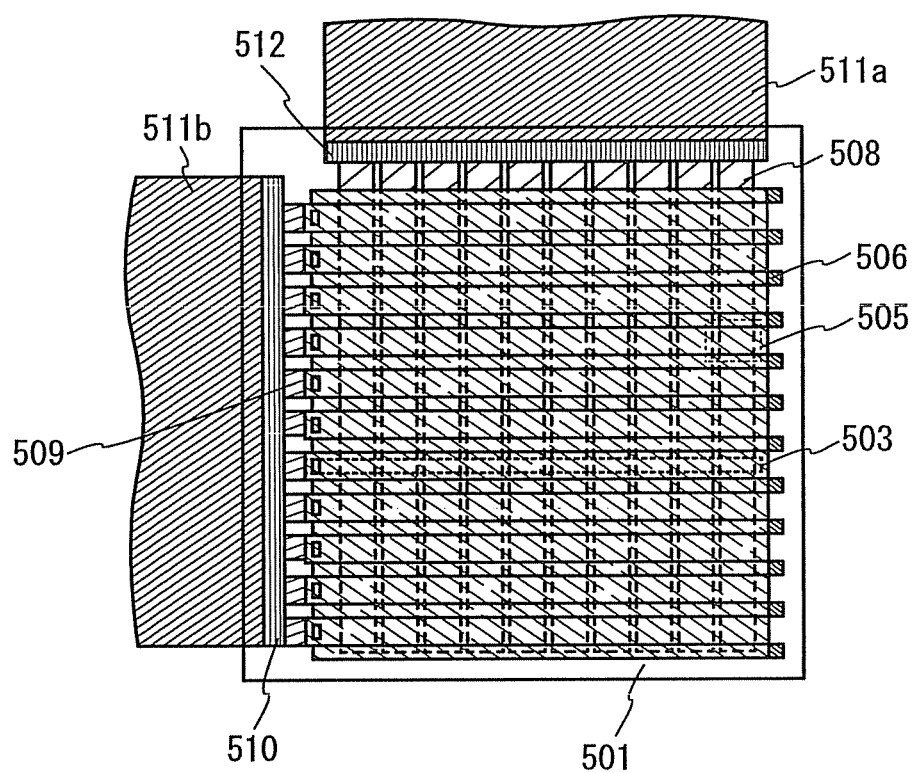
FIG. 5 is a view illustrating a passive matrix light-emitting device.

FIG. 5 is a top view of the case where the passive matrix light-emitting device illustrated in FIGS. 4A to 4D is mounted with an FPC and the like.

In FIG. 5, scan lines and data lines are perpendicularly intersect with each other in a pixel portion for displaying images over a substrate 501.

Here, the first electrode 403, the second electrode 408, and the inversely-tapered partition wall 406 in FIGS. 4A to 4D correspond to a scan line 503, a data line 508, and a partition wall 506 in FIG. 5, respectively. The EL layers 407 in FIGS. 4A to 4D are interposed between the data lines 508 and the scan lines 503, and an intersection portion indicated by a region 505 corresponds to one pixel.

Note that the scan lines 503 are electrically connected at their ends to connection wirings 509, and the connection wirings 509 are connected to an FPC 511b through an input terminal 510. In addition, the data lines are connected to an FPC 511a through the input terminal 512.

If necessary, a polarizing plate, a circularly polarizing plate (including an elliptically polarizing plate), a retardation plate (a quarter-wave plate or a half-wave plate), or an optical film such as a color filter may be provided as appropriate over a light-emitting surface. Further, the polarizing plate or the circularly polarizing plate may be provided with an anti-reflection film. For example, anti-glare treatment may be carried out by which reflected light can be diffused by projections and depressions on the surface so as to reduce the glare.

Note that, although FIG. 5 illustrates an example in which a driver circuit is not provided over the substrate, an IC chip including a driver circuit may be mounted on the substrate.

Further, in the case where the IC chip is mounted, a data line side IC and a scan line side IC, in each of which the driver circuit for transmitting a signal to a pixel portion is formed, are mounted on the periphery of (outside) the pixel portion by a COG method. The mounting may be performed using TCP or a wire bonding method other than the COG method. TCP is a TAB tape mounted with an IC, and a TAB tape is connected to a wiring over an element formation substrate and an IC is mounted. Each of the data line side IC and the scanning line side IC may be formed using a silicon substrate, or may be farmed by formation of a driver circuit with a TFT over a glass substrate, a quartz substrate, or a plastic substrate.

Figure 6A:
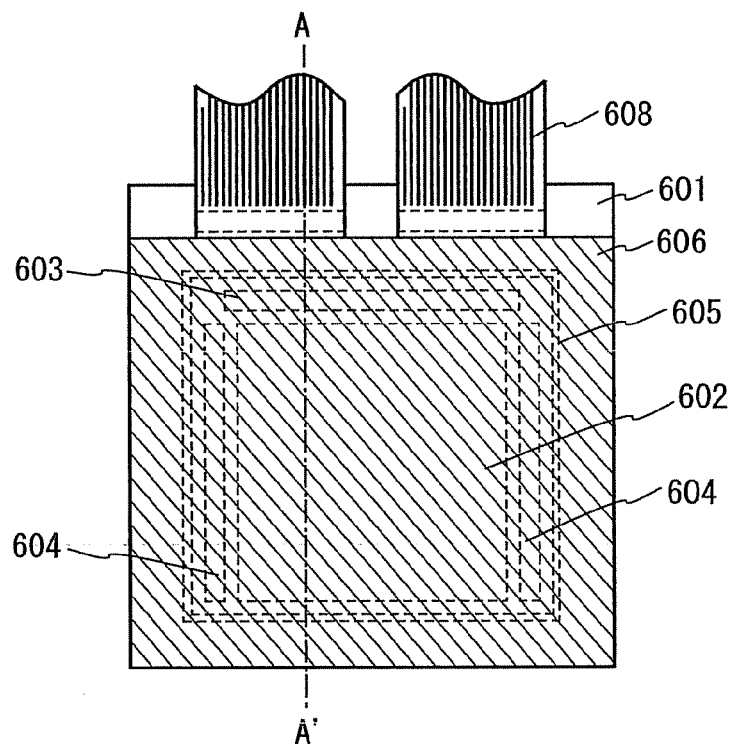
FIGS. 6A and 6B are views illustrating an active matrix light-emitting device.
Figure 6B:
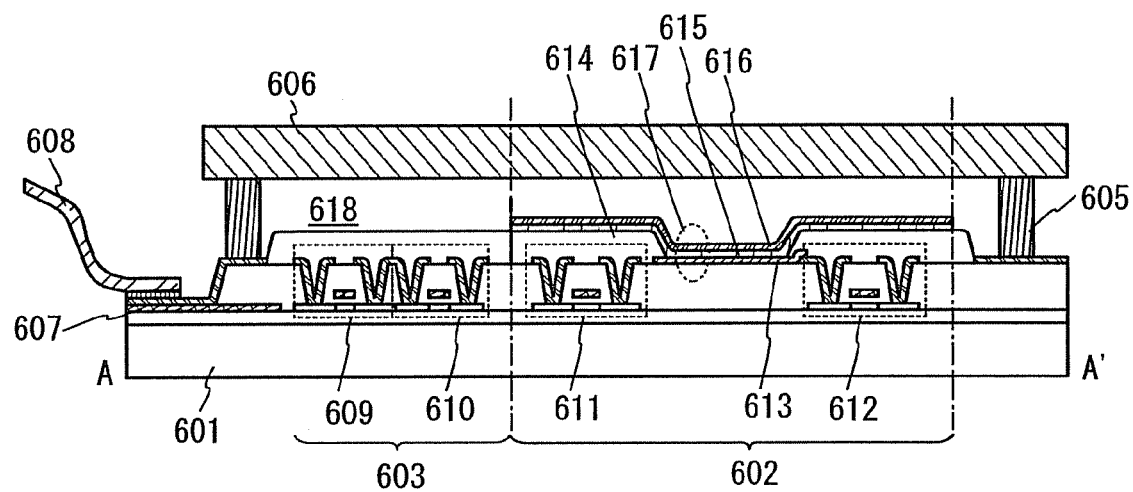

Next, an example of an active-matrix light-emitting device will be described with reference to FIGS. 6A and 6B. Note that FIG. 6A is a top view illustrating a light-emitting device and FIG. 6B is a cross-sectional view taken along the chain line A-A' in FIG. 6A. The active matrix light-emitting device according to this embodiment includes a pixel portion 602 provided over an element substrate 601, a driver circuit portion (a source side driver circuit) 603, and a driver circuit portion (a gate side driver circuit) 604. The pixel portion 602, the driver circuit portion 603, and the driver circuit portion 604 are sealed, with a sealing material 605, between the element substrate 601 and a sealing substrate 606.

In addition, over the element substrate 601, a lead wiring 607 for connecting an external input terminal, through which a signal (e.g., a video signal, a clock signal, a start signal, a reset signal, or the like) or an electric potential is transmitted to the driver circuit portion 603 and the driver circuit portion 604, is provided. Here, an example is described in which a flexible printed circuit (FPC) 608 is provided as the external input terminal. Although only an FPC is shown here, this FPC may have a printed wiring board (PWB) attached. The light-emitting device in this specification includes not only a light-emitting device itself but also a light-emitting device with an FPC or a PWB attached.

Next, a cross-sectional structure will be described with reference to FIG. 6B. The driver circuit portion and the pixel portion are formed over the element substrate 601, and in FIG. 6B, the driver circuit portion 603 that is a source side driver circuit and the pixel portion 602 are illustrated.

An example is illustrated in which a CMOS circuit which is a combination of an n-channel TFT 609 and a p-channel TFT 610 is formed as the driver circuit portion 603. Note that a circuit included in the driver circuit portion may be formed using various types of circuits such as CMOS circuits, PMOS circuits, or NMOS circuits. Although a driver integrated type in which the driver circuit is formed over the substrate is described in this embodiment, the driver circuit may not necessarily be formed over the substrate, and the driver circuit can be foamed outside, not over the substrate.

The pixel portion 602 is formed of a plurality of pixels each of which includes a switching TFT 611, a current control TFT 612, and an anode 613 which is electrically connected to a wiring (a source electrode or a drain electrode) of the current control TFT 612. Note that an insulator 614 is formed to cover end portions of the anode 613. In this embodiment, the insulator 614 is formed using a positive photosensitive acrylic resin.

The insulator 614 is preferably formed so as to have a curved surface with curvature at an upper end portion or a lower end portion thereof in order to obtain favorable coverage by a film which is to be stacked over the insulator 614. For example, in the case of using a positive photosensitive acrylic resin as a material for the insulator 614, the insulator 614 is preferably formed so as to have a curved surface with a curvature radius (0.2 μm to 3 μm) at the upper edge portion. Note that either a negative photosensitive material that becomes insoluble in an etchant by light irradiation or a positive photosensitive material that becomes soluble in an etchant by light irradiation can be used for the insulator 614. As the insulator 614, without limitation to an organic compound, either an organic compound or an inorganic compound such as silicon oxide or silicon oxynitride can be used.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance of the wiring is low and favorable ohmic contact with the ITO film can be obtained. Note that, although not illustrated in FIGS. 6A and 6B, the cathode 616 is electrically connected to an FPC 608 which is an external input terminal.

Note that in the EL layer 615, at least a light-emitting layer is provided, and in addition to the light-emitting layer, a hole-injecting layer, a hole-transporting layer, an electron-transporting layer, or an electron-injecting layer is provided as appropriate. A light-emitting element 617 is formed of a stacked structure of the anode 613, the EL layer 615, and the cathode 616.

Although the cross-sectional view of FIG. 6B illustrates only one light-emitting element 617, a plurality of light-emitting elements are arranged in matrix in the pixel portion 602. Light-emitting elements which provide three kinds of emissions (R, G, and B) are selectively formed in the pixel portion 602, whereby a light-emitting device capable of full color display can be formed. Alternatively, a light-emitting device which is capable of full color display may be manufactured by a combination with color filters.

Further, the sealing substrate 606 is attached to the element substrate 601 with the sealing material 605, whereby a light-emitting element 617 is provided in a space 618 surrounded by the element substrate 601, the sealing substrate 606, and the sealing material 605. The space 618 may be filled with an inert gas (such as nitrogen or argon), or the sealing material 605.

Note that an epoxy-based resin is preferably used as the sealing material 605. Such a material preferably allows as little moisture and oxygen as possible to penetrate. As the sealing substrate 606, a plastic substrate formed of FRP (fiberglass-reinforced plastics), PVF (polyvinyl fluoride), a polyester film; polyester or acrylic; or the like can be used instead of a glass substrate or a quartz substrate.

In this way, an active matrix light-emitting device can be obtained.

Note that the structure described in this embodiment can be combined with any of the structures described in Embodiments 1 to 5 as appropriate.

Embodiment 7

In this embodiment, examples of various electronic devices and lighting devices, which are completed using the light-emitting device of one embodiment of the present invention, will be described with reference to FIGS. 7A to 7E and FIG. 8.

As the electronic devices to which the light-emitting device is applied, for example, there are a television device (also referred to as TV or a television receiver), a monitor for a computer or the like, a camera such as a digital camera, a digital video camera, a digital photo frame, a mobile phone (also referred to as a cellular phone or a portable telephone device), a portable game machine, a portable information terminal, an audio playback device, and a large game machine such as a pin-ball machine. Specific examples of these electronic devices and lighting device are illustrated in FIGS. 7A to 7E.

Figure 7A:
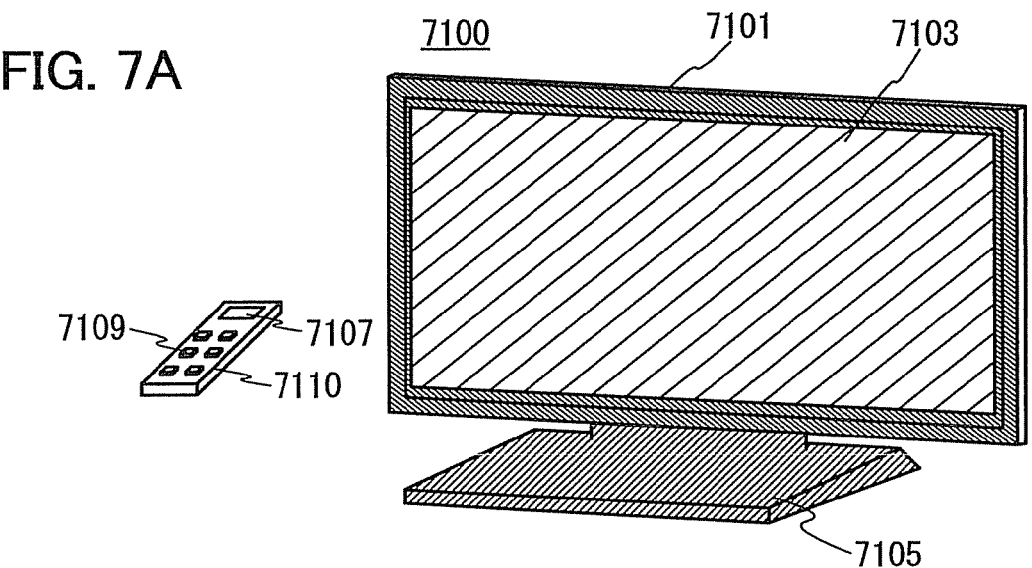
FIGS. 7A to 7E are diagrams illustrating electronic devices.

FIG. 7A illustrates an example of a television device 7100. In the television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 7B:
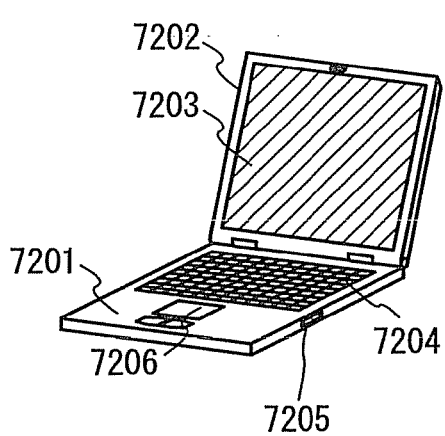

FIG. 7B illustrates a computer, which includes a main body 7201, a housing 7202, a display portion 7203, a keyboard 7204, an external connecting port 7205, a pointing device 8106, and the like. This computer is manufactured by using a light-emitting device for the display portion 7203.

Figure 7C:
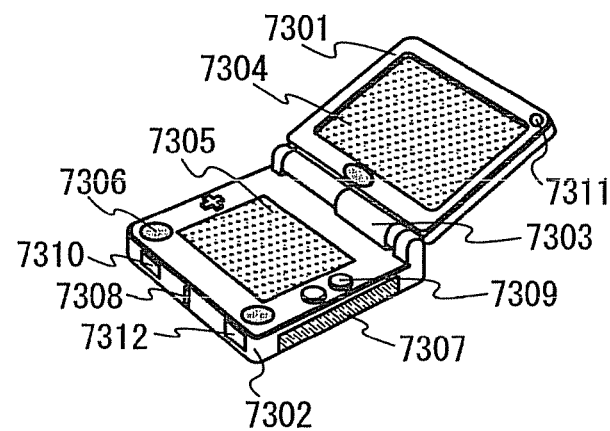

FIG. 7C illustrates a portable game machine, which includes two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 7C includes a speaker portion 7306, a recording medium insertion portion 7307, an LED lamp 7308, an input means (an operation key 7309, a connection terminal 73107, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
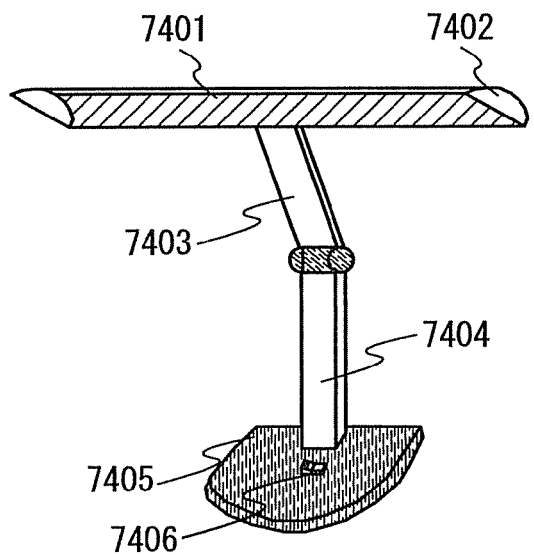

FIG. 7D illustrates a desk lamp, which includes a lighting portion 7401, a lampshade 7402, an adjustable arm 7403, a support 7404, a base 7405, and a power supply 7406. The desk lamp is manufactured using a light-emitting device for the lighting portion 7401. Note that the lighting device includes a ceiling light, a wall light, and the like in its category.

Figure 7E:
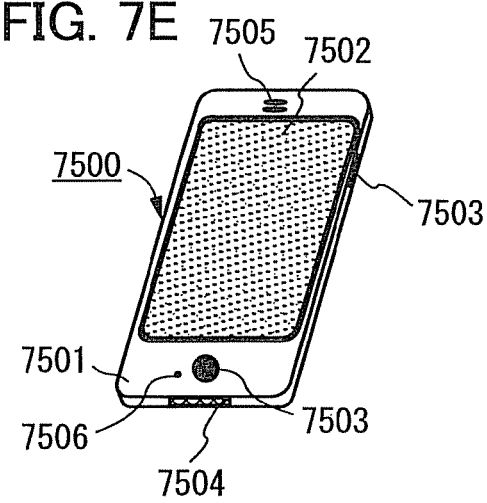

FIG. 7E illustrates an example of a cellular phone. The cellular phone 7500 is provided with a display portion 7502 incorporated in a housing 7501, operation buttons 7503, an external connection port 7504, a speaker 7505, a microphone 7506, and the like. Note that the cellular phone 7500 is manufactured using a light-emitting device for the display portion 7502.

When the display portion 7502 of the cellular phone 7500 illustrated in FIG. 7E is touched with a finger or the like, data can be input into the cellular phone 7500. Further, operations such as making calls and composing e-mails can be performed by touching the display portion 7502 with a finger or the like.

There are mainly three screen modes of the display portion 7502. The first mode is a display mode mainly for displaying an image. The second mode is an input mode mainly for inputting information such as characters. The third mode is a display-and-input mode in which two modes of the display mode and the input mode are mixed.

For example, in the case of making a call or composing an e-mail, a text input mode mainly for inputting text is selected for the display portion 7502 so that text displayed on a screen can be inputted. In that case, it is preferable to display a keyboard or number buttons on almost all the area of the screen of the display portion 7502.

When a detection device including a sensor for detecting inclination, such as a gyroscope or an acceleration sensor, is provided inside the cellular phone 7500, display on the screen of the display portion 7502 can be automatically changed by determining the orientation of the cellular phone 7500 (whether the mobile phone handset 1000 is placed horizontally or vertically for a landscape mode or a portrait mode).

The screen modes are switched by touching the display portion 7502 or operating the operation buttons 7503 of the housing 7501. Alternatively, the screen modes can be switched depending on kinds of images displayed on the display portion 7502. For example, when a signal for an image displayed in the display portion is data of moving images, the screen mode is switched to the display mode. When the signal is text data, the screen mode is switched to the input mode.

Moreover, in the input mode, when input by touching the display portion 7502 is not performed within a specified period while a signal detected by an optical sensor in the display portion 7502 is detected, the screen mode may be controlled so as to be switched from the input mode to the display mode.

The display portion 7502 can function as an image sensor. For example, an image of a palm print, a fingerprint, or the like is taken by touching the display portion 7502 with the palm or the finger, whereby personal authentication can be performed. Furthermore, by provision of a backlight or a sensing light source emitting a near-infrared light for the display portion, an image of a finger vein, a palm vein, or the like can also be taken.

FIG. 8 illustrates an example in which the light-emitting device is used for an indoor lighting device 801. Since the light-emitting device can have a larger area, the light-emitting device can be used as a lighting device having a large area. Alternatively, the light-emitting device can be used as a roll-type lighting device 802. Note that as illustrated in FIG. 8, a desk lamp 803 described with reference to FIG. 7D may be used together in a room provided with the indoor lighting device 801.

As described above, electronic devices and a lighting device can be obtained by application of the light-emitting device. Application range of the light-emitting device is so wide that the light-emitting device can be applied to electronic devices in a variety of fields.

Note that the structure described in this embodiment can be combined with any of the structures described in Embodiments 1 to 6 as appropriate.

Example 1

Synthesis Example 1

In this example, a synthesis method of (acetylacetonato)bis[2-(5-methoxyphenyl)-3,5-dimethylpyrazinato)iridium (III) (abbreviation: [Ir(dm5moppr)$_2$(acac)]), which is the organometallic complex of one embodiment of the present invention represented by Structural Formula (100) in Embodiment 1, will be described. A structure of [Ir(dm5moppr)$_2$(acac)] is shown below.

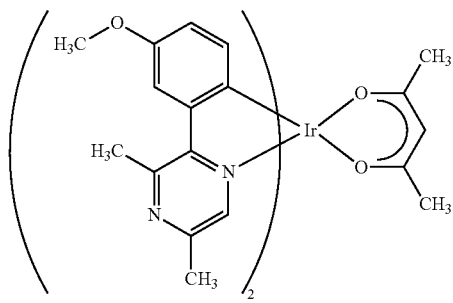

(100)

Step 1: Synthesis of 2-(3-methoxyphenyl)-3,5-dimethylpyrazine (Abbreviation: Hdm5moppr)

First, into a recovery flask equipped with a reflux pipe were put 1.01 g of 2-chloro-3,5-dimethylpyrazine, 1.08 g of 3-methoxyphenylboronic acid, 0.75 g of sodium carbonate, 0.032 g of bis(triphenylphosphine)palladium(II)dichloride (abbreviation: Pd(PPh$_3$)$_2$Cl$_2$), 10 mL of water, and 10 mL of acetonitrile, and the atmosphere in the flask was replaced with argon. This reaction container was subjected to irradiation with microwave (2.45 GHz, 100 W) for 10 minutes to be heated. Note that the irradiation with microwave in this example was performed using a microwave synthesis system (Discover, produced by CEM Corporation).

Next, water was added to this solution, and an organic layer was extracted with dichloromethane. The obtained organic layer was washed with water and dried with magnesium sulfate. After the drying, the solution was filtrated. The solvent of this solution was distilled off, whereby a pyrazine derivative Hdm5moppr, which was a target substance, was obtained (dark yellow liquid, yield: 85%). A synthesis scheme of Step 1 is shown in (a-1) below.

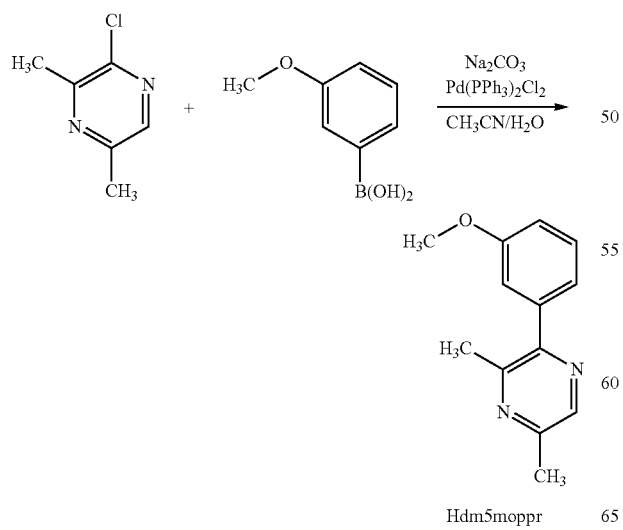

(a-1)

Step 2: Synthesis of di-β-chloro-bis[bis{2-(5-methoxyphenyl)-3,5-dimethylpyrazinato}iridium(III)] (Abbreviation: [Ir(dm5moppr)$_2$Cl]$_2$)

Next, into a recovery flask equipped with a reflux pipe were put 15 mL of 2-ethoxyethanol, 5 mL of water, 1.29 g of Hdm5moppr obtained in above Step 1, and 0.72 g of iridium chloride hydrate (IrCl$_3$.H$_2$O) (produced by Sigma-Aldrich Corp.), and the atmosphere in the flask was replaced with argon. After that, irradiation with microwave (2.45 GHz, 100 W) for 30 minutes was performed to cause a reaction. The solution after the reaction was concentrated and a residue obtained was washed with ethanol, whereby a dinuclear complex [Ir(dm5moppr)$_2$Cl]$_2$ was obtained (a dark yellow powder, yield: 71%). Further, a synthesis scheme of Step 2 is shown in (b-1) below.

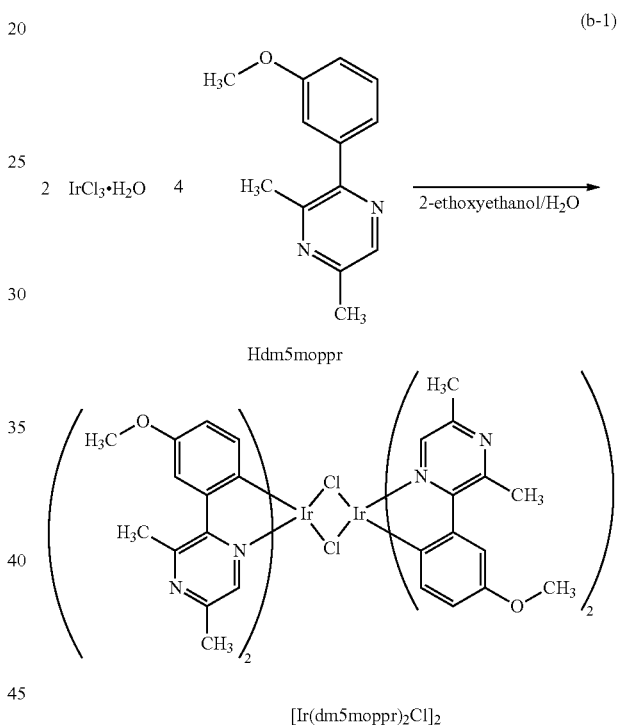

(b-1)

Step 3: Synthesis of (acetylacetonato)bis[2-(5-methoxyphenyl)-3,5-dimethylpyrazinato]iridium(III) (Abbreviation: [Ir(dm5moppr)$_2$(acac)])

Furthermore, into a recovery flask equipped with a reflux pipe were put 10 mL of 2-ethoxyethanol, 0.51 g of the dinuclear complex [Ir(dm5moppr)$_2$Cl]$_2$ obtained in above Step 2, 0.12 mL of acetylacetone, and 0.41 g of sodium carbonate, and the atmosphere in the flask was replaced with argon. After that, irradiation with microwave (2.45 GHz, 100 W) for 30 minutes was performed to cause a reaction. The reaction solution was filtrated. The obtained solid was dissolved in ethanol and the solution was filtrated to remove insoluble matter. Then, the filtrate was recrystallized with ethanol, whereby the organometallic complex [Ir(dm5moppr)$_2$(acac)], which is one embodiment of the present invention, was obtained (a red powder, yield: 67%). A synthesis scheme of Step 3 is shown in (c-1) below.

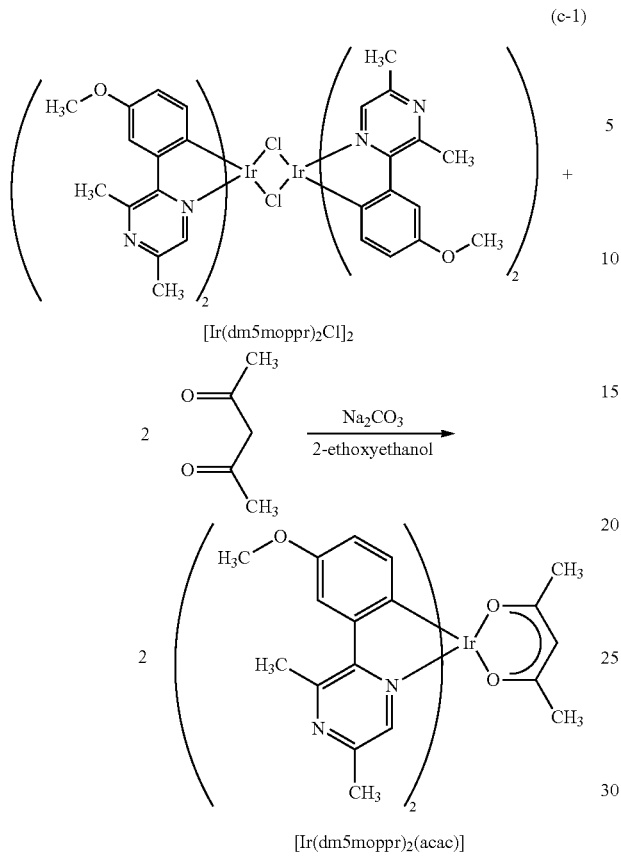

[Ir(dm5moppr)₂Cl]₂

[Ir(dm5moppr)₂(acac)]

Figure 9:
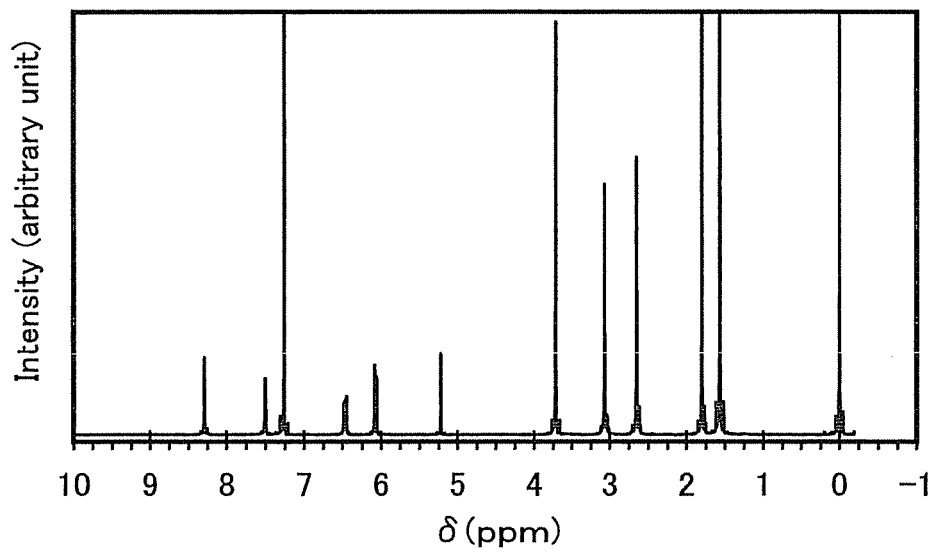
FIG. 9 is a $^1$H-NMR chart of an organometallic complex represented by Structural Formula (100)

Results of analysis of the red powder obtained in above Step 3 by nuclear magnetic resonance spectrometry ($^1$H NMR) are shown below. In addition, FIG. 9 is a $^1$H NMR chart. According to the results, it was found that the organometallic complex [Ir(dm5moppr)₂(acac)], which is one embodiment of the present invention and represented by Structural Formula (100) above, was obtained in this example.

$^1$H-NMR. δ (CDCl₃): 1.80 (s, 6H), 2.65 (s, 6H), 3.07 (s, 6H), 3.71 (s, 6H), 5.22 (s, 1H), 6.07 (d, 2H), 6.47 (dd, 2H), 7.50 (d, 2H), 8.29 (s, 2H).

Figure 10:
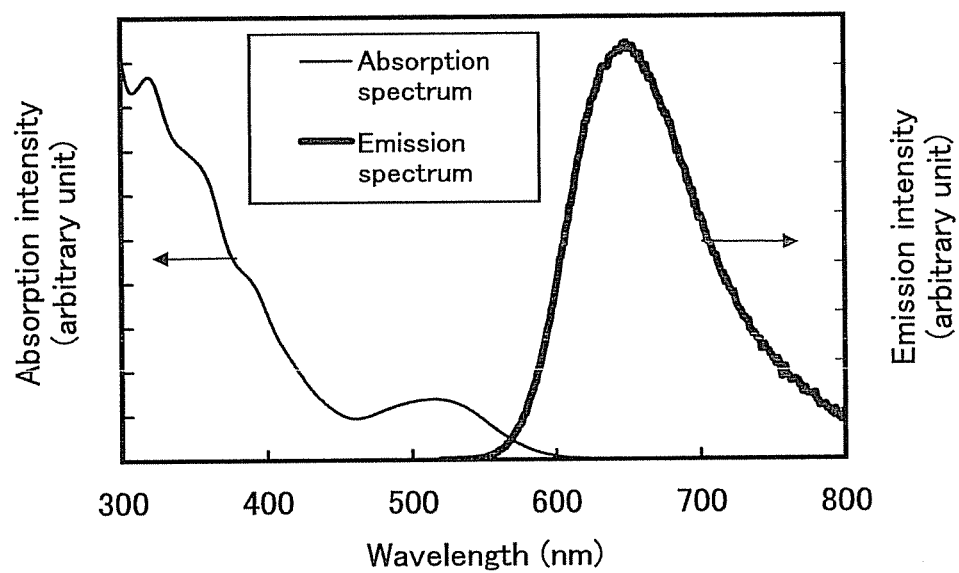
FIG. 10 is a graph showing an ultraviolet-visible absorption spectrum and an emission spectrum of the organometallic complex represented by Structural Formula (100)

Next, [Ir(dm5moppr)₂(acac)] was analyzed by an ultraviolet-visible (UV) absorption spectroscopy. The UV spectrum was measured using an ultraviolet-visible spectrophotometer (V550, produced by JASCO Corporation) at a room temperature by use of a dichloromethane solution (0.071 mmol/L). In addition, an emission spectrum of [Ir(dm5moppr)₂(acac)] was measured. The emission spectrum was measured by a fluorescence spectrophotometer (FS920, produced by Hamamatsu Photonics Corporation) using a degassed dichloromethane solution (0.42 mmol/L) at a room temperature. FIG. 10 shows the measurement results. The horizontal axis indicates the wavelength (nm), and the vertical axis indicates the absorption intensity (arbitrary unit) and the emission intensity (arbitrary unit).

As shown in FIG. 10, the organometallic complex [Ir(dm5moppr)₂(acac)] which is one embodiment of the present invention has a peak of emission at 648 nm, and red light was observed from the dichloromethane solution.

Example 2

Figure 11:
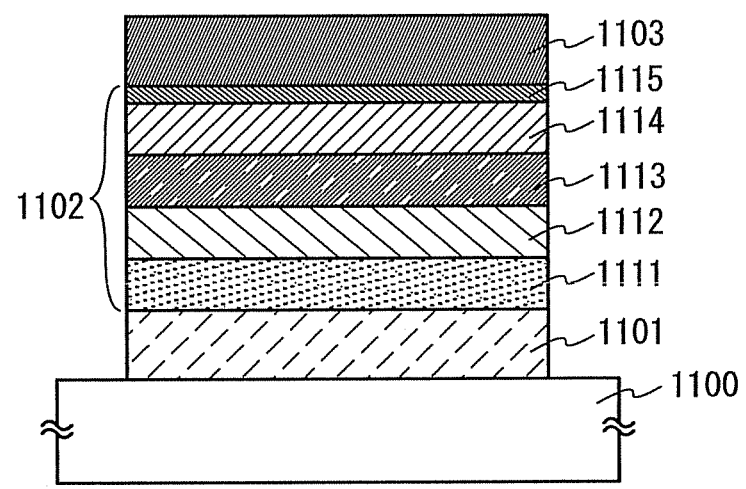
FIG. 11 is a view illustrating a light-emitting element which is one embodiment of the present invention.

A light-emitting element (a light-emitting element 3) will be described in which the organometallic complex [Ir(dm5moppr)₂(acac)], which is one embodiment of the present invention, represented by Structural Formula (100), and synthesized in Example 1, is used as a light-emitting substance. Further, as comparative light-emitting elements, light-emitting elements (a light-emitting element 1 and a light-emitting element 2) will also be described in which light-emitting substances represented by Structural Formulae (i) and (ii) below are used as light-emitting substances. Note that structures of organic compounds used in this example are represented by Structural Formulae (iii) to (vi). In addition, element structures of the light-emitting elements will be described on the basis of FIG. 11.

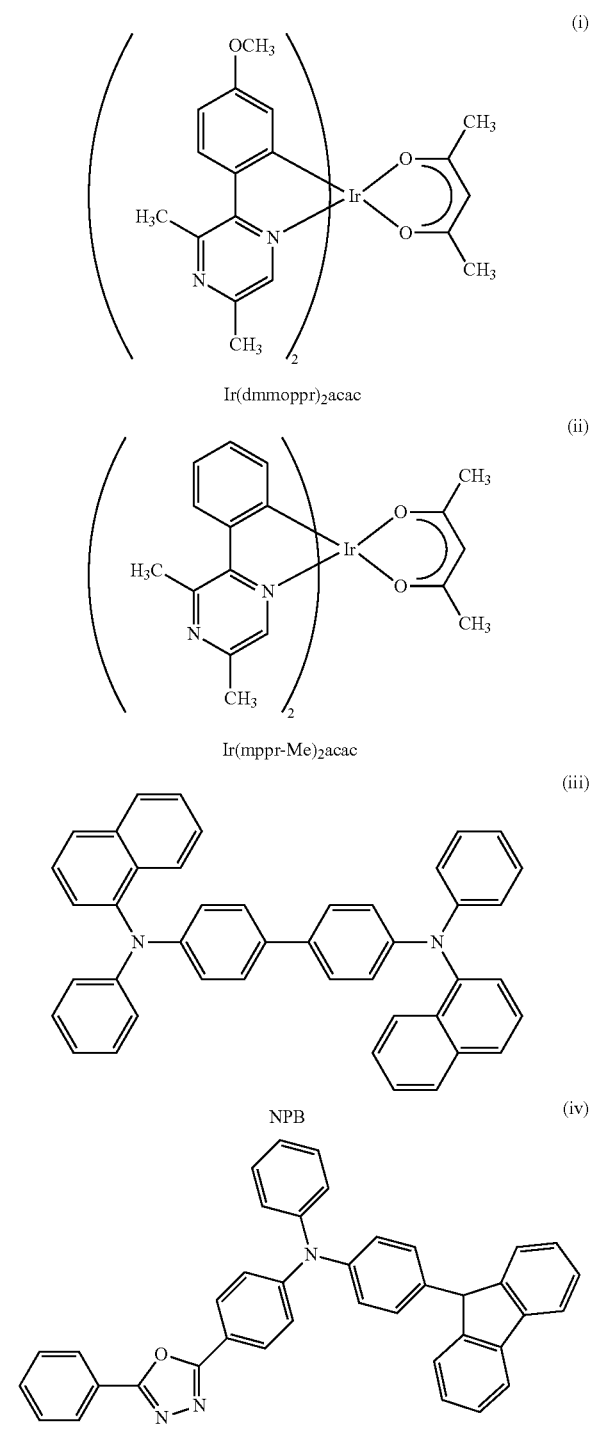

Ir(dmmoppr)₂acac

Ir(mppr-Me)₂acac

NPB

YGAO11

-continued

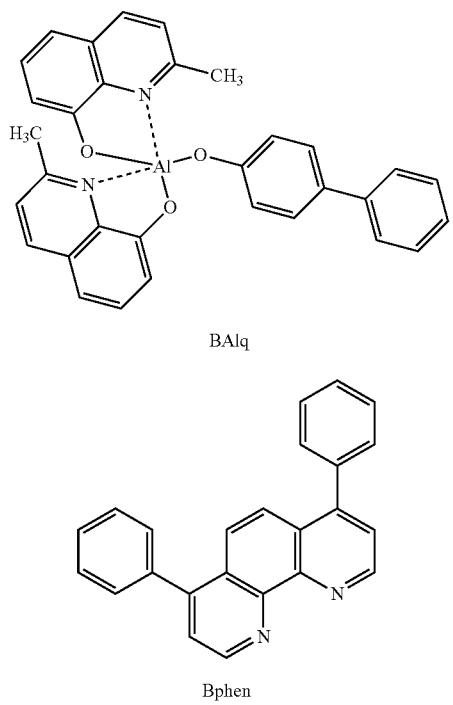

BAlq (v)

Bphen (vi)

<<Manufacture of Light-Emitting Elements 1 to 3>>

First, as a first electrode 1101, indium tin oxide containing silicon oxide (ITSO) is formed to a thickness of 110 nm over a substrate 1100 made of glass. Note that the periphery of the ITSO is covered with an insulating film so that a surface of the ITSO of 2 mm×2 mm is exposed. Here, the first electrode 1101 is an electrode that functions as an anode of the light-emitting element.

Next, as pretreatment for forming the light-emitting element over the substrate 1100, the surface of the substrate was washed with water using a porous resin brush, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injecting layer 1111, a hole-transporting layer 1112, a light-emitting layer 1113, an electron-transporting layer 1114, and an electron-injecting layer 1115 which are included in an EL layer 1102 are sequentially formed.

After reducing the pressure of the vacuum evaporation apparatus to $10^{-4}$ Pa, NPB represented by above Structural Formula (iii) and molybdenum(VI) oxide were co-evaporated with a mass ratio of NPB to molybdenum(VI) oxide being 4:1, whereby the hole-injecting layer 1111 was formed. The thickness of the hole-injecting layer 1111 was 50 nm. Note that the co-evaporation is an evaporation method in which some different substances are evaporated from some different evaporation sources at the same time.

Next, NPB was evaporated to a thickness of 10 nm as a hole-transporting layer 1112.

Next, the light-emitting layer 1113 was formed over the hole-transporting layer 1112. In the case of the light-emitting element 1, over the hole-transporting layer 1112, YGAO11 represented by above Structural Formula (Iv) and [Ir(dm-moppr)$_2$(acac)] represented by above Structural Formula (i) were co-evaporated with a mass ratio of YGAO11 to [Ir(dmmoppr)$_2$(acac)] being 1:0.05, whereby the light-emitting layer 1113 was formed. In the case of the light-emitting element 2, over the hole-transporting layer 1112, YGAO11 and [Ir(mppr-Me)$_2$(acac)] were co-evaporated with a mass ratio of YGAO11 to [Ir(mppr-Me)$_2$(acac)] being 1:0.05, whereby the light-emitting layer 1113 was formed. In the case of the light-emitting element 3, over the hole-transporting layer 1112, YGAO11 and [Ir(dm5moppr)$_2$(acac)] were co-evaporated with a mass ratio of YGAO11 to [Ir(dm5moppr)$_2$(acac)] being 1:0.05, whereby the light-emitting layer 1113 was formed. The thickness of the light-emitting layer 1113 in each case was 30 nm.

Next, after evaporating BAlq represented by above Structural Formula (v) to a thickness of 10 nm, BPhen represented by above Structural Formula (vi) was further evaporated to a thickness of 20 nm, whereby the electron-transporting layer 1114 was formed. Furthermore, lithium fluoride was evaporated to a thickness of 2 nm over the electron-transporting layer 1114, whereby the electron-injecting layer 1115 was formed.

Next, aluminum was deposited to a thickness of 200 nm as a second electrode 1103. Thus, the light-emitting elements (the light-emitting elements 1 to 3) each of which is one embodiment of the present invention were obtained. Note that the second electrode 1103 is an electrode that functions as a cathode. In the above evaporation steps, evaporation was all performed by a resistance heating method.

Further, these light-emitting elements were sealed in a glove box under a nitrogen atmosphere to prevent being exposed to the atmosphere.

<<Operation Characteristics of Light-Emitting Elements 1 to 3>>

Operation characteristics of each of the manufactured light-emitting elements (light-emitting elements 1 to 3) were measured. Note that the measurement was carried out at a room temperature (under an atmosphere in which the temperature was kept at 25° C.).

Figure 12:
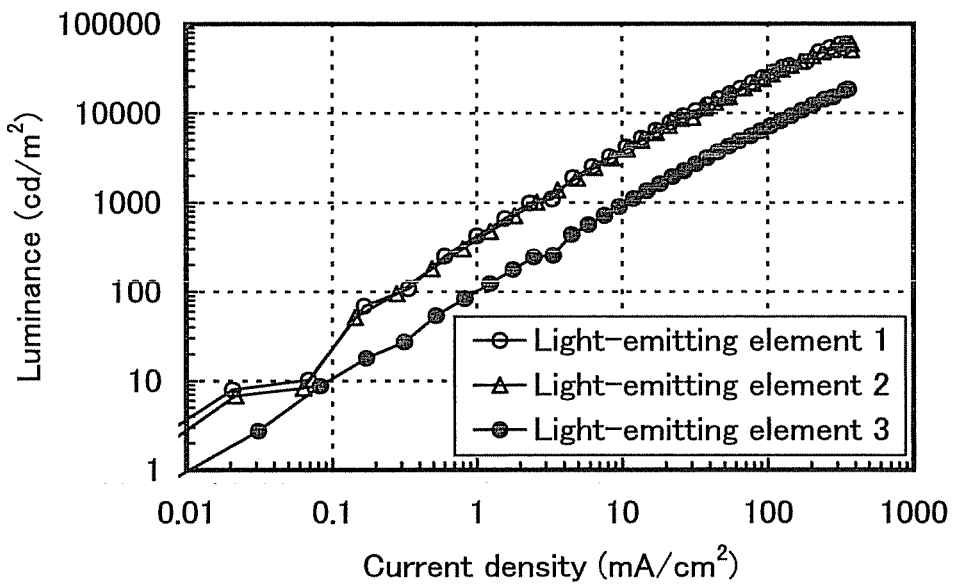
FIG. 12 is a graph showing current density-luminance characteristics of light-emitting elements each of which is one embodiment of the present invention.
Figure 13:
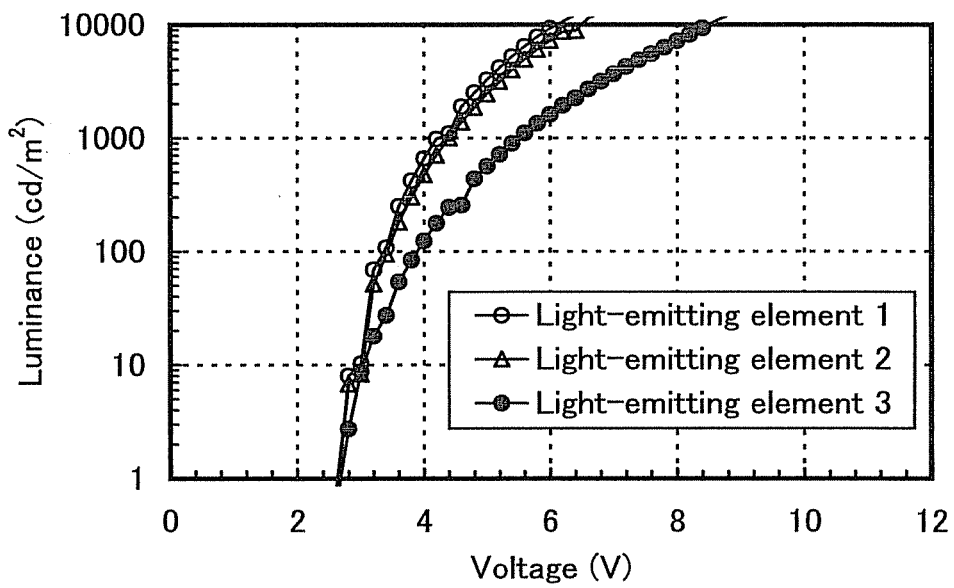
FIG. 13 is a graph showing voltage-luminance characteristics of the light-emitting elements each of which is one embodiment of the present invention.

FIG. 12 shows current density-luminance characteristics of each light-emitting element. In FIG. 12, the vertical axis represents luminance (cd/m$^2$) and the horizontal axis represents current density (mA/cm$^2$). FIG. 13 shows voltage-luminance characteristics of each light-emitting element. In FIG. 13, the vertical axis represents luminance (cd/m$^2$) and the horizontal axis represents voltage (V). Table 2 below shows initial values of main characteristics of each light-emitting element at a luminance of about 1000 cd/m$^2$.

TABLE 2

| | Voltage (V) | Chromaticity (x, y) | Current efficiency (cd/A) | External quantum efficiency (%) |
|---|---|---|---|---|
| Light-emitting element 1 | 4.2 | (0.50, 0.49) | 41.9 | 14.0 |
| Light-emitting element 2 | 4.4 | (0.54, 0.46) | 38.4 | 14.8 |
| Light-emitting element 3 | 5.4 | (0.68, 0.32) | 9.3 | 11.9 |

The above results show that the light-emitting element 3 has high emission efficiency because it exhibited external quantum efficiency substantially the same as external quantum efficiencies of the light-emitting element 1 and the light-emitting element 2. It was also found that, as for the color purity, the light-emitting element 3 exhibited red emission with higher color purity than the light-emitting elements 1 and 2 which exhibited orange emission.

Figure 14:
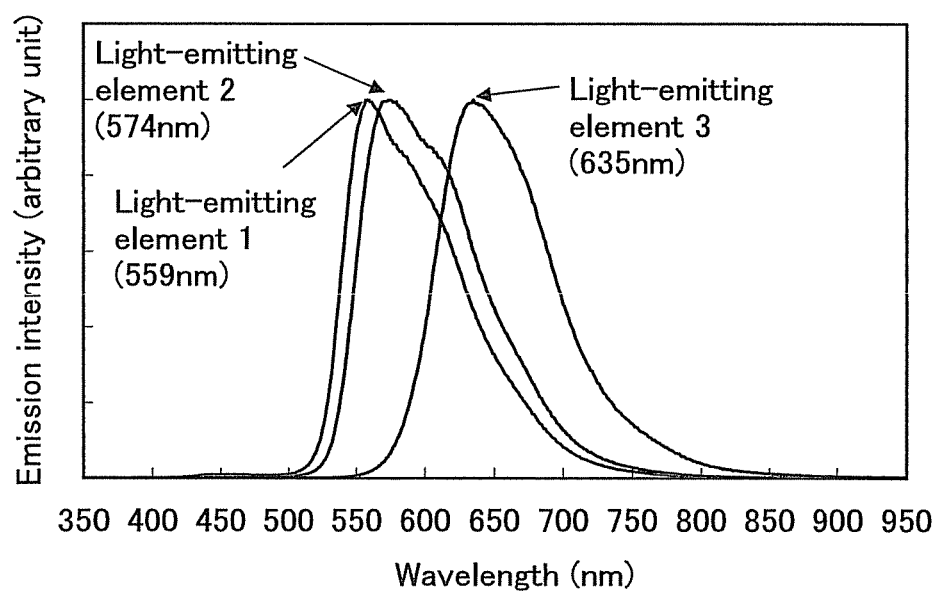
FIG. 14 is a graph showing emission spectra of the light-emitting elements each of which is one embodiment of the present invention.

FIG. 14 shows an emission spectrum when a current at a current density of 25 mA/cm$^2$ was supplied to each light-emitting element. As shown in FIG. 14, the light-emitting element 1, the light-emitting element 2, and the light-emitting element 3 have peaks of emission spectra at 559 nm, 574 nm, and 635 nm, respectively. FIG. 14 indicates that the emission spectrum of the light-emitting element 3 is derived from emission of the organometallic complex [Ir(dm5moppr)$_2$(acac)] which is one embodiment of the present invention.

Example 3

Synthesis Example 2

In this example, a synthesis method of an organometallic complex bis[2-(5-methoxyphenyl)-3,5-dimethylpyrazinato](picolinato)iridium(III) (abbreviation: [Ir(dm5moppr)$_2$(pic)]) of one embodiment of the present invention, which is represented by Structural Formula (102) in Embodiment 1, will be described. Note that a structure of [Ir(dm5moppr)$_2$(pic)] is shown below.

(102)

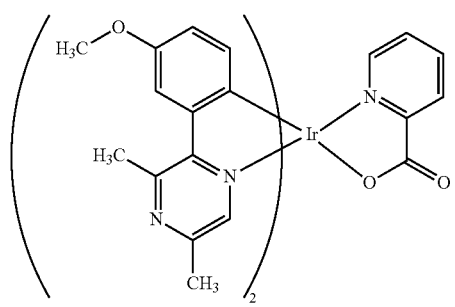

Synthesis of bis[2-(5-methoxyphenyl)-3,5-dimethylpyrazinato](picolinato)iridium(III) (Abbreviation: [Ir(dm5moppr)$_2$(pic)])

Into a recovery flask equipped with a reflux pipe were put 20 mL of dichloromethane, 0.68 g of the dinuclear complex [Ir(dm5moppr)$_2$Cl]$_2$, and 0.51 g of picolinic acid, and the atmosphere in the flask was replaced with argon. (Note that the dinuclear complex [Ir(dm5moppr)$_2$Cl]$_2$ can be obtained by the same synthesis method as in Step 2 of Synthesis Example 1 in Embodiment 1.) After that, irradiation with microwave (2.45 GHz, 100 W) for 30 minutes was performed to cause a reaction. Note that the irradiation with microwave in this example was performed using a microwave synthesis system (Discover, produced by CEM Corporation).

Next, the reaction solution was filtrated. The obtained filtrate was concentrated and dried using an evaporator. The obtained residue was recrystallized with methanol, whereby the organometallic complex [Ir(dm5moppr)$_2$(pic)] which is one embodiment of the present invention was obtained (a red powder, yield: 56%). A synthesis scheme of this step is shown in (c-2) below.

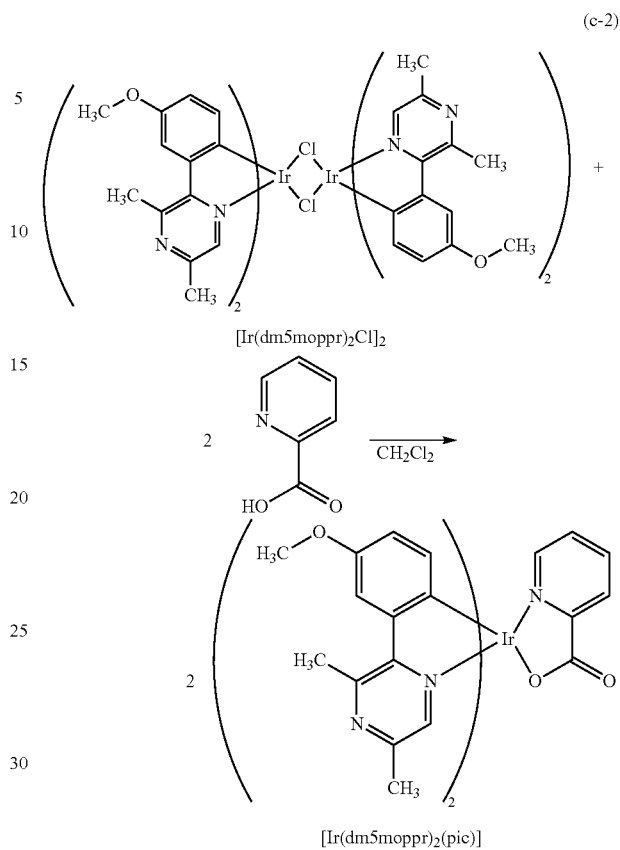

Figure 15:
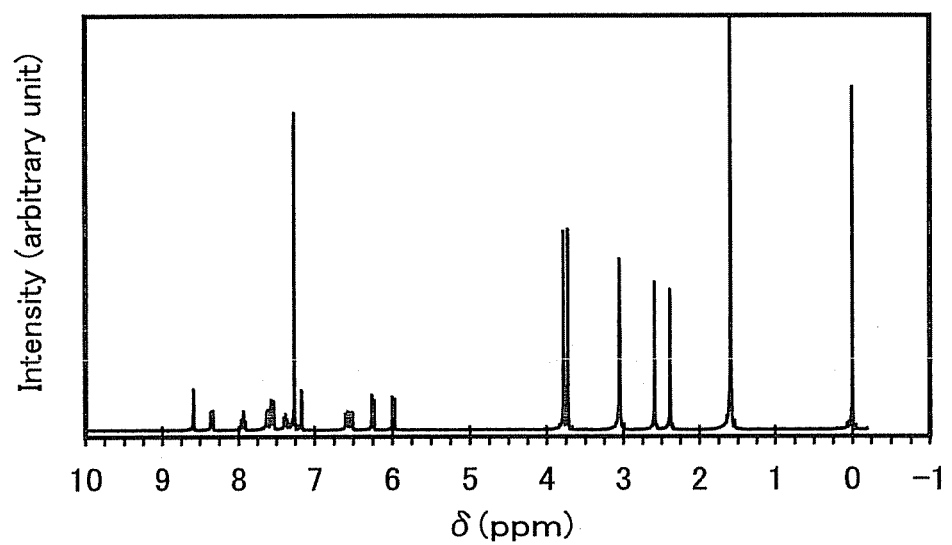
FIG. 15 is a $^1$H-NMR chart of an organometallic complex represented by Structural Formula (102)

Results of analysis of the red powder obtained in the above step by nuclear magnetic resonance spectrometry ($^1$H NMR) are shown below. In addition, FIG. 15 is a $^1$H NMR chart. According to the results, it was found that the organometallic complex [Ir(dm5moppr)$_2$(pic)] of one embodiment of the present invention, which is represented by Structural Formula (102) above, was obtained in this example.

$^1$H-NMR. δ (CDCl$_3$): 2.39 (s, 3H), 2.59 (s, 3H), 3.05 (s, 6H), 3.73 (s, 3H), 3.78 (s, 3H), 5.99 (d, 1H), 6.25 (d, 1H), 6.53 (dd, 1H), 6.59 (dd, 1H), 7.21 (s, 1H), 7.38 (m, 1H), 7.55 (dd, 2H), 7.62 (d, 1H), 7.94 (dt, 1H), 8.35 (d, 1H), 8.59 (s, 1H).

Figure 16:
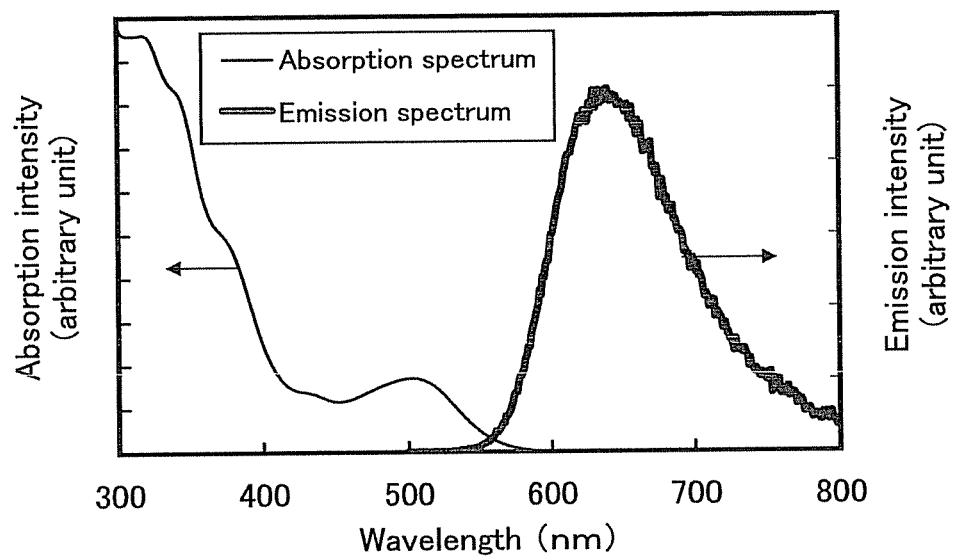
FIG. 16 is a graph showing an ultraviolet-visible absorption spectrum and an emission spectrum of the organometallic complex represented by Structural Formula (102)

Next, [Ir(dm5moppr)$_2$(pic)] was analyzed by an ultraviolet-visible (UV) absorption spectroscopy. The UV spectrum was measured using an ultraviolet-visible spectrophotometer (V550, produced by JASCO Corporation) at a room temperature by use of a dichloromethane solution (0.069 mmol/L). In addition, an emission spectrum of [Ir(dm5moppr)$_2$(pic)] was measured. The emission spectrum was measured by a fluorescence spectrophotometer (FS920, produced by Hamamatsu Photonics Corporation) using a degassed dichloromethane solution (0.41 mmol/L) at a room temperature. FIG. 16 shows the measurement results. The horizontal axis indicates the wavelength (nm), and the vertical axis indicates the absorption intensity (arbitrary unit) and the emission intensity (arbitrary unit).

As shown in FIG. 16, the organometallic complex [Ir(dm5moppr)$_2$(pic)] which is one embodiment of the present invention has a peak of emission at 639 nm, and red light was observed from the dichloromethane solution.

Example 4

A light-emitting element (a light-emitting element 4) will be described in which the organometallic complex [Ir (dm5moppr)$_2$(pic)] of one embodiment of the present invention, which is represented by Structural Formula (102) and synthesized in Example 3, is used as a light-emitting substance. Note that of organic compounds used in this example, the ones described in Example 2 will not be described. In addition, an element structure of the light-emitting element will be described on the basis of FIG. 11.

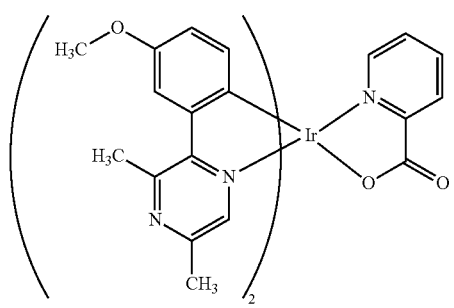

(102)

<<Manufacture of Light-Emitting Element 4>>

First, as a first electrode 1101, indium tin oxide containing silicon oxide (ITSO) is formed to a thickness of 110 nm over a substrate 1100 made of glass. Note that the periphery of the ITSO is covered with an insulating film so that a surface of the ITSO of 2 mm×2 mm is exposed. Here, the first electrode 1101 is an electrode that functions as an anode of the light-emitting element.

Next, as pretreatment for forming the light-emitting element over the substrate 1100, the surface of the substrate was washed with water using a porous resin brush, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injecting layer 1111, a hole-transporting layer 1112, a light-emitting layer 1113, an electron-transporting layer 1114, and an electron-injecting layer 1115 which are included in an EL layer 1102 are sequentially formed.

After reducing the pressure of the vacuum evaporation apparatus to $10^{-4}$ Pa, NPB and molybdenum(VI) oxide were co-evaporated with a mass ratio of NPB to molybdenum(VI) oxide being 4:1, whereby the hole-injecting layer 1111 was formed. The thickness of the hole-injecting layer 1111 was 50 nm. Note that the co-evaporation is an evaporation method in which some different substances are evaporated from some different evaporation sources at the same time.

Next, NPB was evaporated to a thickness of 10 nm as a hole-transporting layer 1112.

Next, over the hole-transporting layer 1112, YGAO11 and [Ir(dm5moppr)$_2$(pic)] represented by above Structural Formula (102) were co-evaporated with a mass ratio of YGAO11 to [Ir(dm5moppr)$_2$(pic)] being 1:0.05, whereby the light-emitting layer 1113 was formed. The thickness of the light-emitting layer 1113 was 30 nm.

Next, after evaporating BAlq to a thickness of 10 nm, BPhen was further evaporated to a thickness of 20 nm, whereby the electron-transporting layer 1114 was formed. Furthermore, lithium fluoride was evaporated to a thickness of 2 nm over the electron-transporting layer 1114, whereby the electron-injecting layer 1115 was formed.

Next, aluminum was deposited to a thickness of 200 nm as a second electrode 1103. Thus, the light-emitting element 4 which is one embodiment of the present invention was obtained. Note that the second electrode 1103 is an electrode that functions as a cathode. In the above evaporation steps, evaporation was all performed by a resistance heating method.

Further, the light-emitting element was sealed in a glove box under a nitrogen atmosphere to prevent being exposed to the atmosphere.

<<Operating Characteristics of Light-Emitting Element 4>>

Operation characteristics of the manufactured light-emitting element 4 were measured. Note that the measurement was carried out at a room temperature (under an atmosphere in which the temperature was kept at 25° C.).

Figure 17:
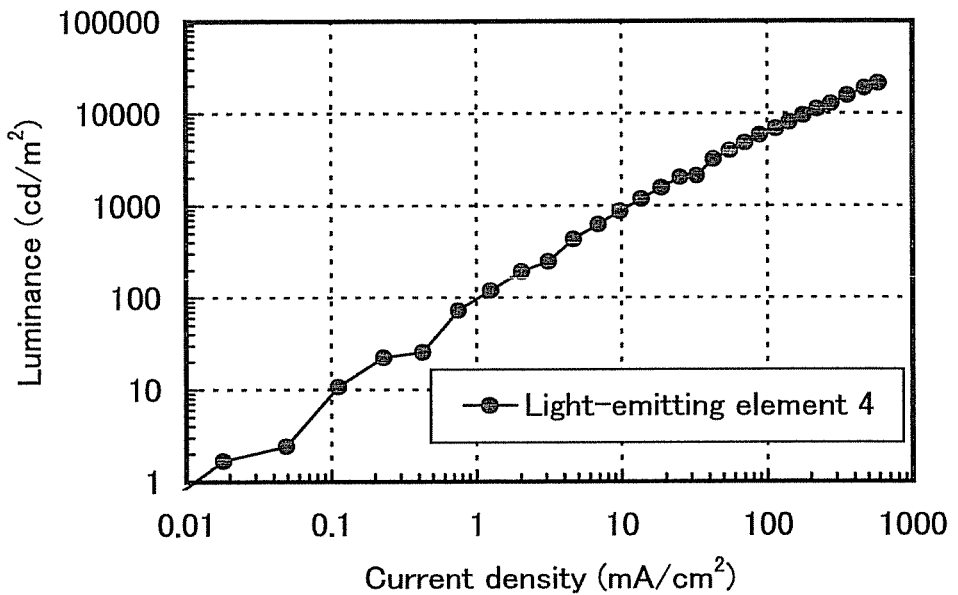
FIG. 17 is a graph showing current density-luminance characteristics of a light-emitting element which is one embodiment of the present invention.
Figure 18:
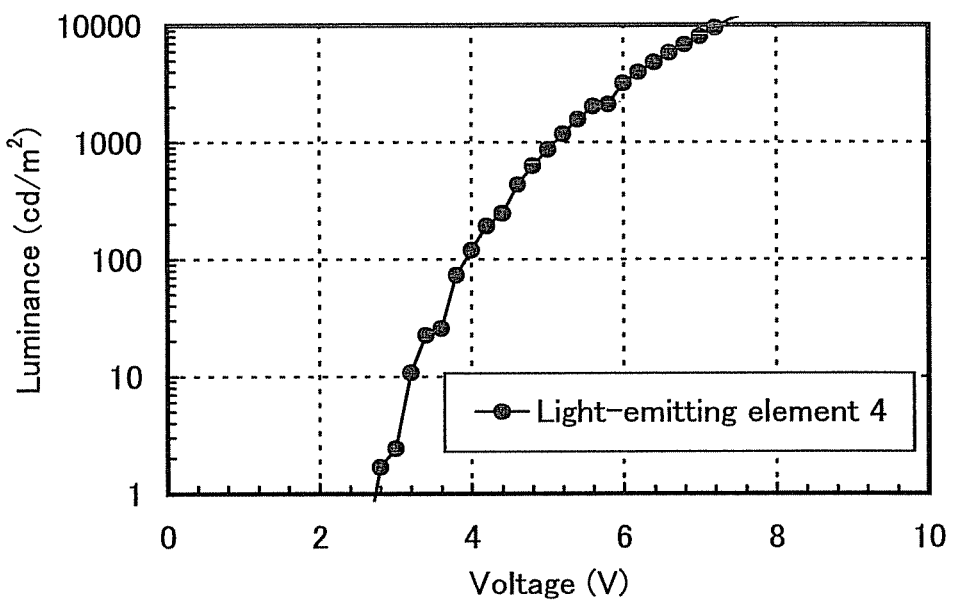
FIG. 18 is a graph showing voltage-luminance characteristics of the light-emitting element which is one embodiment of the present invention.

FIG. 17 shows current density-luminance characteristics of the light-emitting element 4. In FIG. 17, the vertical axis represents luminance (cd/m$^2$) and the horizontal axis represents current density (mA/cm$^2$). FIG. 18 shows voltage-luminance characteristics of the light-emitting element 4. In FIG. 18, the vertical axis represents luminance (cd/m$^2$) and the horizontal axis represents voltage (V).

In addition, the chromaticity of light emitted from the light-emitting element 4 is (0.64, 0.36), which shows that the light-emitting element 4 exhibits red emission with excellent color purity.

Figure 19:
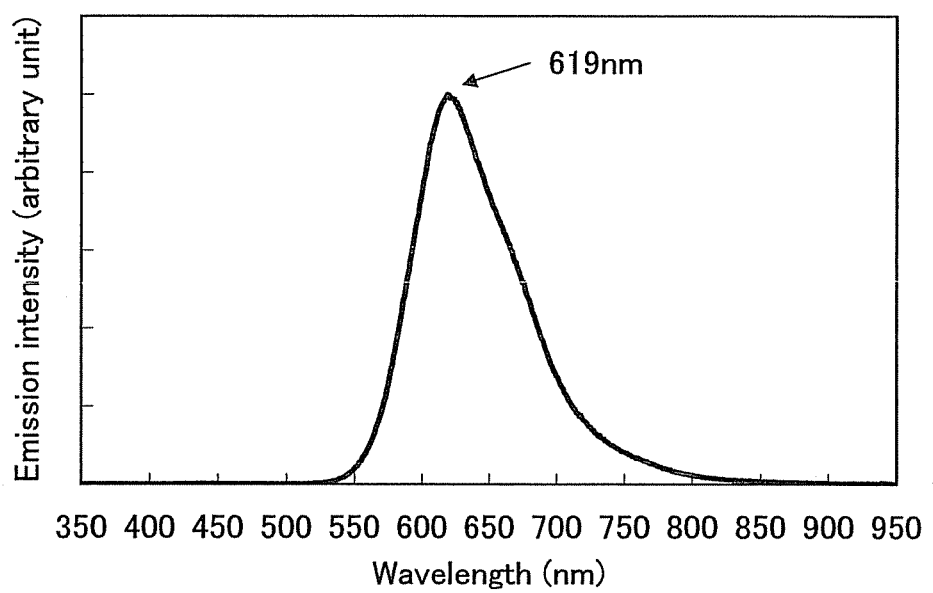
FIG. 19 is a graph showing an emission spectrum of the light-emitting element which is one embodiment of the present invention.

FIG. 19 shows an emission spectrum when a current at a current density of 25 mA/cm$^2$ was supplied to the light-emitting element 4. As shown in FIG. 19, the light-emitting element 4 has a peak of emission spectrum at 619 nm. FIG. 19 indicates that the emission spectrum of the light-emitting element 4 is derived from emission of the organometallic complex [Ir(dm5moppr)$_2$(pic)] which is one embodiment of the present invention.

Example 5

Synthesis Example 3

In this example, a synthesis method of an organometallic complex bis[2-(5-methoxyphenyl)-3,5-dimethylpyrazinato](pivaloyltrifluoroacetonato)iridium(III) (abbreviation: [Ir(dm5moppr)$_2$(pFac)]) of one embodiment of the present invention, which is represented by Structural Formula (108), in Embodiment 1 will be described. Note that a structure of [Ir(dm5moppr)$_2$(pFac)] is shown below.

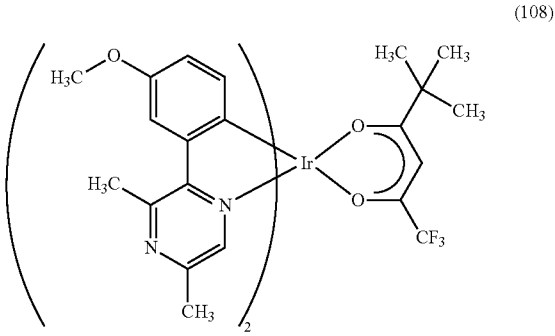

(108)

Synthesis of bis[2-(5-methoxyphenyl)-3,5-dimethylpyrazinato](pivaloyltrifluoroacetonato)iridium(III) (Abbreviation: [Ir(dm5moppr)$_2$(pFac)])

Into a recovery flask equipped with a reflux pipe were put 15 mL of 2-ethoxyethanol, 0.41 g of a dinuclear complex [Ir(dm5moppr)$_2$Cl]$_2$, 0.16 mL of pivaloyltrifluoroacetone, and 0.33 g of sodium carbonate, and the atmosphere in the flask was replaced with argon. (Note that the dinuclear complex [Ir(dm5moppr)$_2$Cl]$_2$ can be obtained by the same synthesis method as in Step 2 of Synthesis Example 1 in Embodiment 1.) After that, irradiation with microwave (2.45 GHz, 100 W) for 30 minutes was performed to cause a reaction. Note that the irradiation with microwave in this example was performed using a microwave synthesis system (Discover, produced by CEM Corporation).

Next, the reaction solution was filtrated. The obtained filtrate was concentrated and dried using an evaporator. The obtained residue was recrystallized with a mixed solvent of dichloromethane and methanol, whereby the organometallic complex [Ir(dm5moppr)$_2$(pFac)] which is one embodiment of the present invention was obtained (a red powder, yield: 26%). A synthesis scheme of this step is shown in (c-3) below.

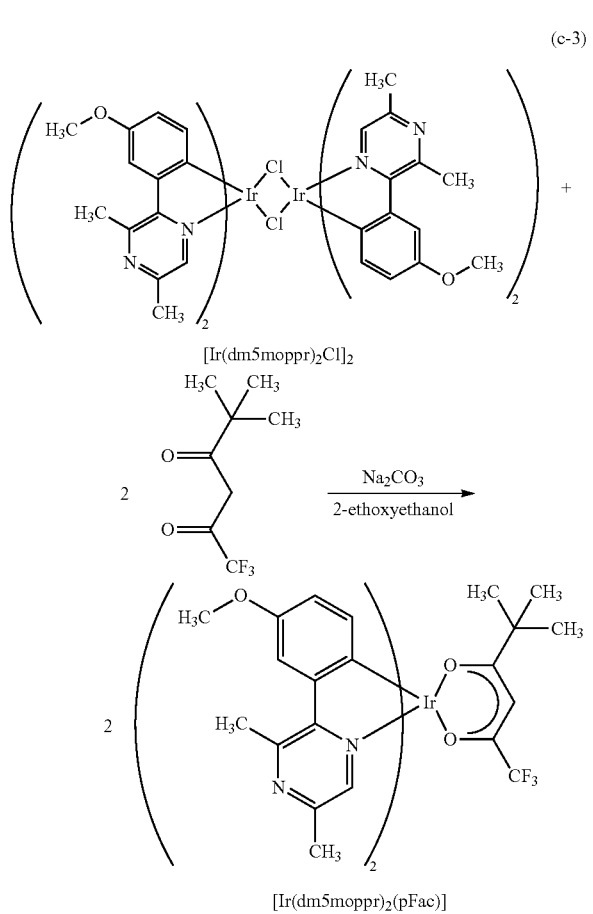

(c-3)

Figure 20:
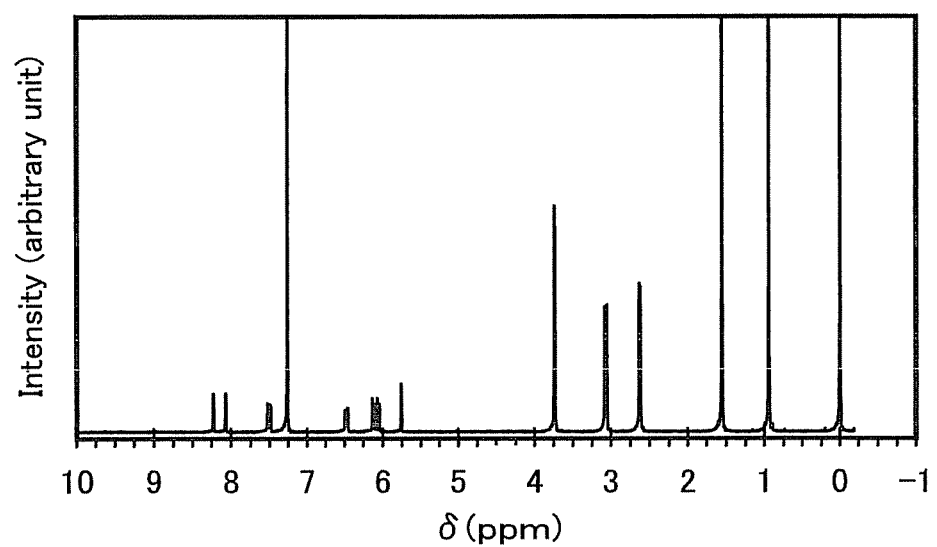
FIG. 20 is a $^1$H-NMR chart of an organometallic complex represented by Structural Formula (108)

Results of analysis of the red powder obtained in the above step by nuclear magnetic resonance spectrometry ($^1$H NMR) are shown below. In addition, FIG. 20 is a $^1$H NMR chart. According to the results, it was found that the organometallic complex [Ir(dm5moppr)$_2$(pFac)] of one embodiment of the present invention, which is represented by Structural Formula (108) above, was obtained in this example.

$^1$H-NMR. δ (CDCl$_3$): 0.94 (s, 9H), 2.62 (s, 6H), 3.05 (s, 3H), 3.08 (s, 3H), 3.74 (d, 6H), 5.76 (s, 1H), 6.09 (dd, 2H), 6.47 (td, 2H), 7.50 (dd, 2H), 8.07 (s, 1H), 8.22 (s, 1H).

Figure 21:
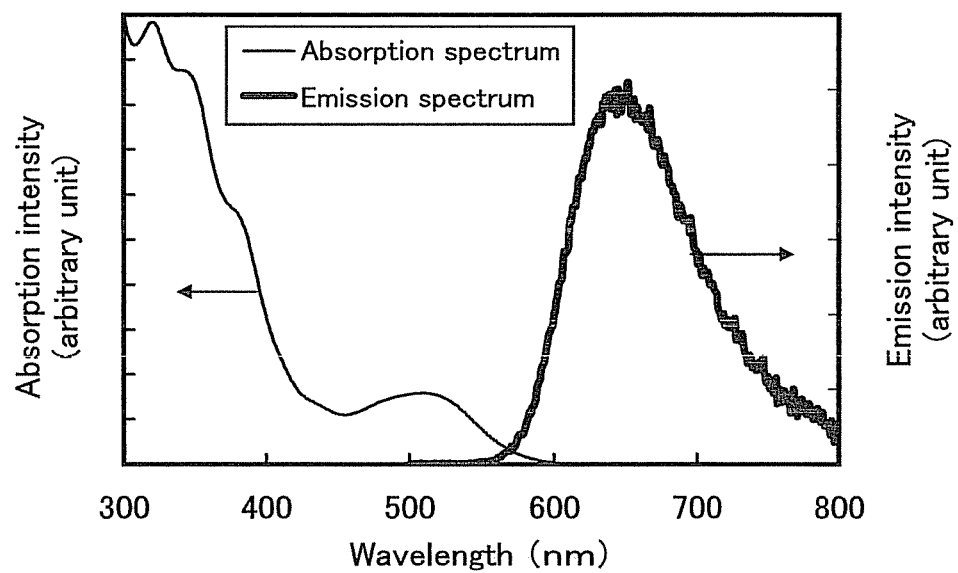
FIG. 21 is a graph showing an ultraviolet-visible absorption spectrum and an emission spectrum of the organometallic complex represented by Structural Formula (108)

Next, [Ir(dm5moppr)$_2$(pFac)] was analyzed by an ultraviolet-visible (UV) absorption spectroscopy. The UV spectrum was measured using an ultraviolet-visible spectrophotometer (V550, produced by JASCO Corporation) at a room temperature by use of a dichloromethane solution (0.069 mmol/L). In addition, an emission spectrum of [Ir(dm5moppr)$_2$(pFac)] was measured. The emission spectrum was measured by a fluorescence spectrophotometer (FS920, produced by Hamamatsu Photonics Corporation) using a degassed dichloromethane solution (0.41 mmol/L) at a room temperature. FIG. 21 shows the measurement results. The horizontal axis indicates the wavelength (nm), and the vertical axis indicates the absorption intensity (arbitrary unit) and the emission intensity (arbitrary unit).

As shown in FIG. 21, the organometallic complex [Ir(dm5moppr)$_2$(pFac)] which is one embodiment of the present invention has a peak of emission at 645 nm, and red light was observed from the dichloromethane solution.

Example 6

Synthesis Example 4

In this example, a synthesis method of an organometallic complex tris[2-(5-methoxyphenyl)-3,5-dimethylpyrazinato] (abbreviation: [Ir(dm5moppr)$_3$]) of one embodiment of the present invention, which is represented by Structural Formula (110) in Embodiment 1, will be described. Note that a structure of [Ir(dm5moppr)$_3$] is shown below.

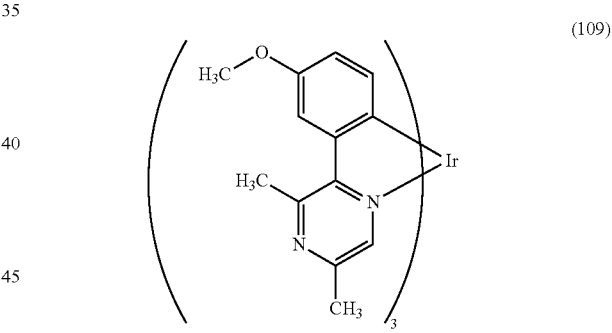

(109)

Synthesis of tris[2-(5-methoxyphenyl)-3,5-dimethylpyrazinato]iridium(III) (Abbreviation: [Ir(dm5moppr)$_3$])

Into a recovery flask equipped with a reflux pipe were put 20 mL of glycerin, 0.19 g of a uninuclear complex [Ir(dm5moppr)$_2$(acac)], and 0.14 g of Hdm5moppr that is a ligand, and the atmosphere in the flask was replaced with argon. (Note that the uninuclear complex [Ir(dm5moppr)$_2$(acac)] can be obtained by the same synthesis method as in Step 3 of Synthesis Example 1 in Embodiment 1, and Hdm5moppr that is a ligand can be obtained by the same synthesis method as in Step 1 of Synthesis Example 1 in Example 1.) After that, irradiation with microwave (2.45 GHz, 100 W) for 30 minutes was performed to cause a reaction. Note that the irradiation with microwave in this example was performed using a microwave synthesis system (Discover, produced by CEM Corporation).

Next, water was added to the reaction solution, the mixture solution was filtrated, and the solid obtained by the filtration was washed with ethanol. The obtained solid was dissolved in dichloromethane and the solution was filtrated. The obtained filtrate was concentrated and dried using an evaporator to obtain a residue. The residue was recrystallized with methanol, whereby the organometallic complex [Ir(dm5moppr)$_3$] which is one embodiment of the present invention was obtained (a red powder, yield: 5%). A synthesis scheme of this step is shown in (c-4) below.

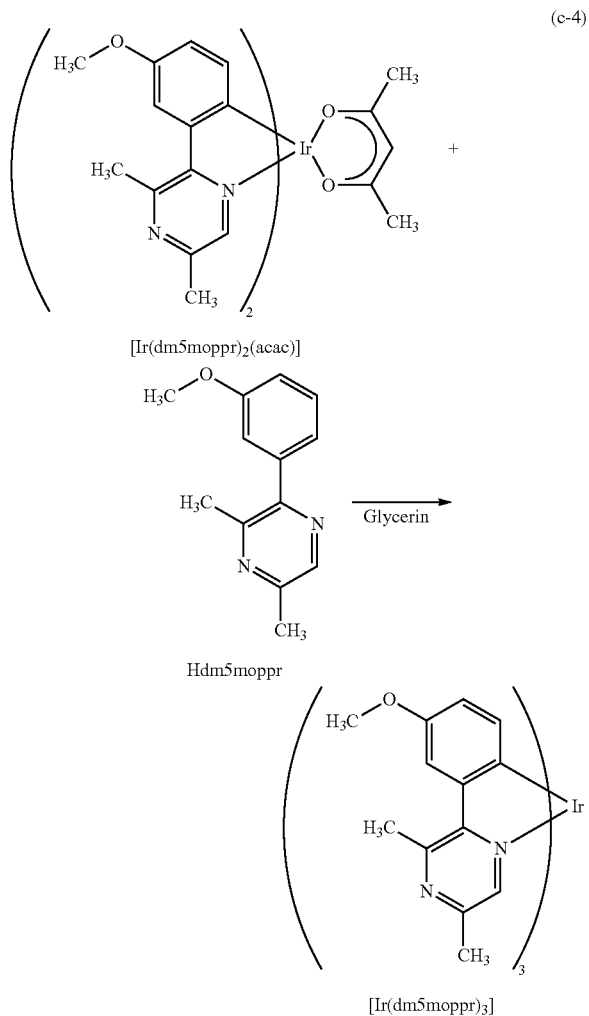

[Ir(dm5moppr)$_2$(acac)]

Hdm5moppr

[Ir(dm5moppr)$_3$]

Figure 22:
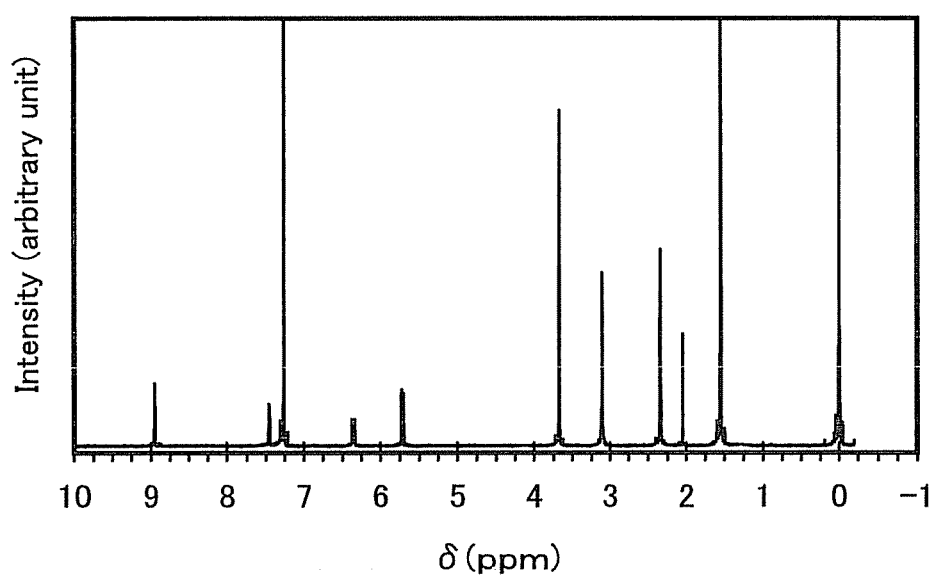
FIG. 22 is a $^1$H-NMR chart of an organometallic complex represented by Structural Formula (110)

Results of analysis of the red powder obtained in the above step by nuclear magnetic resonance spectrometry ($^1$H NMR) are shown below. In addition, FIG. 22 is a $^1$H NMR chart. According to the results, it was found that the organometallic complex [Ir(dm5moppr)$_3$] of one embodiment of the present invention, which is represented by Structural Formula (110) above, was obtained in this example.

$^1$H-NMR. δ (CDCl$_3$): 2.34 (s, 9H), 3.11 (s, 9H), 3.67 (s, 9H), 5.72 (d, 3H), 6.35 (dd, 3H), 7.46 (d, 3H), 8.95 (s, 3H).

Figure 23:
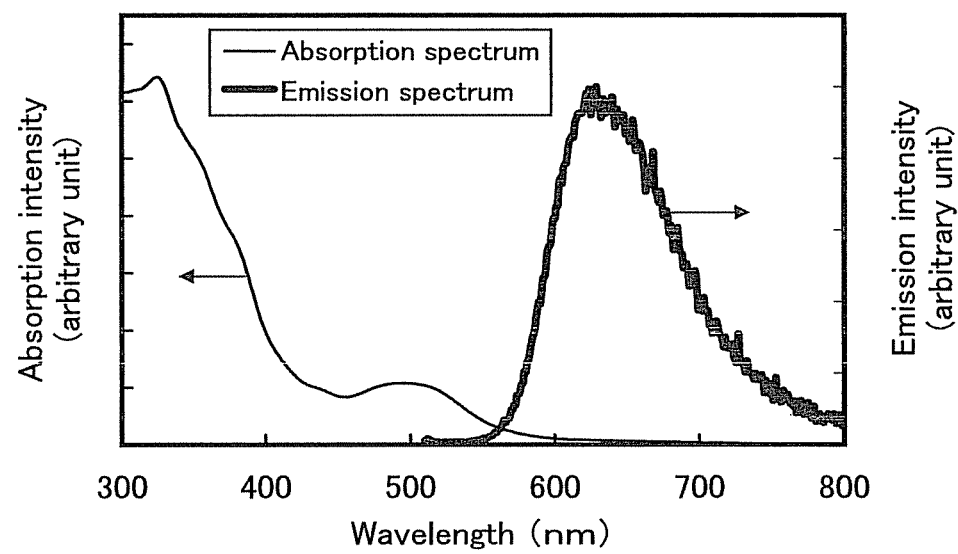
FIG. 23 is a graph showing an ultraviolet-visible absorption spectrum and an emission spectrum of the organometallic complex represented by Structural Formula (110)

Next, [Ir(dm5moppr)$_3$] was analyzed by an ultraviolet-visible (UV) absorption spectroscopy. The UV spectrum was measured using an ultraviolet-visible spectrophotometer (V550, manufactured by JASCO Corporation) at a room temperature by using a dichloromethane solution (0.051 mmol/L). In addition, an emission spectrum of [Ir(dm5moppr)$_3$] was measured. The emission spectrum was measured by a fluorescence spectrophotometer (FS920, produced by Hamamatsu Photonics Corporation) using a degassed dichloromethane solution (0.31 mmol/L) at a room temperature. FIG. 23 shows the measurement results. The horizontal axis indicates the wavelength (nm), and the vertical axis indicates the absorption intensity (arbitrary unit) and the emission intensity (arbitrary unit).

As shown in FIG. 23, the organometallic complex [Ir(dm5moppr)$_3$] which is one embodiment of the present invention has a peak of emission at 630 nm, and red light was observed from the dichloromethane solution.

Example 7

Synthesis Example 5

In this example, a synthesis method of an organometallic complex (acetylacetonato)bis[2-(4,5-methoxyphenyl)-3,5-dimethylpyrazinato)iridium(III) (abbreviation: [Ir(dm4,5moppr)$_2$(acac)]) of one embodiment of the present invention, which is represented by Structural Formula (112) in Embodiment 1, will be described. Note that a structure of [Ir(dm4,5moppr)$_2$(acac)] is shown below.

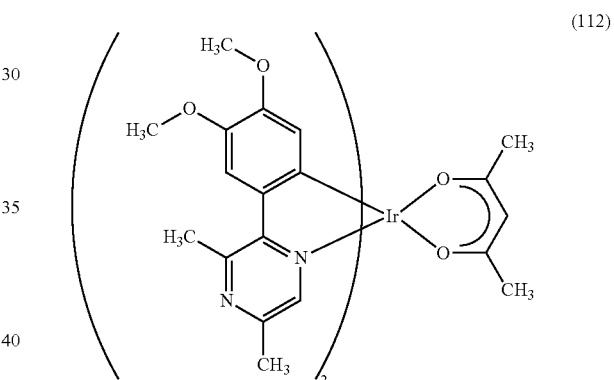

(112)

Step 1: Synthesis of
2-(3,4-methoxyphenyl)-3,5-dimethylpyrazine
(Abbreviation: Hdm4,5moppr)

First, into a recovery flask equipped with a reflux pipe were put 1.05 g of 2-chloro-3,5-dimethylpyrazine, 1.34 g of 4-methoxyphenylboronic acid, 0.78 g of sodium carbonate, 0.034 g of bis(triphenylphosphine)palladium(II)dichloride (abbreviation: Pd(PPh$_3$)$_2$Cl$_2$), 10 mL of water, and 10 mL of acetonitrile, and the atmosphere in the flask was replaced with argon. This reaction container was subjected to irradiation with microwave (2.45 GHz, 100 W) for 10 minutes to be heated. Note that the irradiation with microwave in this example was performed using a microwave synthesis system (Discover, produced by CEM Corporation).

Next, water was added to this solution, and an organic layer was extracted with dichloromethane. The obtained organic layer was washed with water and dried with magnesium sulfate. After the drying, the solution was filtrated. The solvent of this solution was distilled off, whereby a pyrazine derivative Hdm4,5moppr, which was a target substance, was obtained (a milky white powder, yield: 100%). A synthesis scheme of Step 1 is shown in (a-5) below.

(a-5)

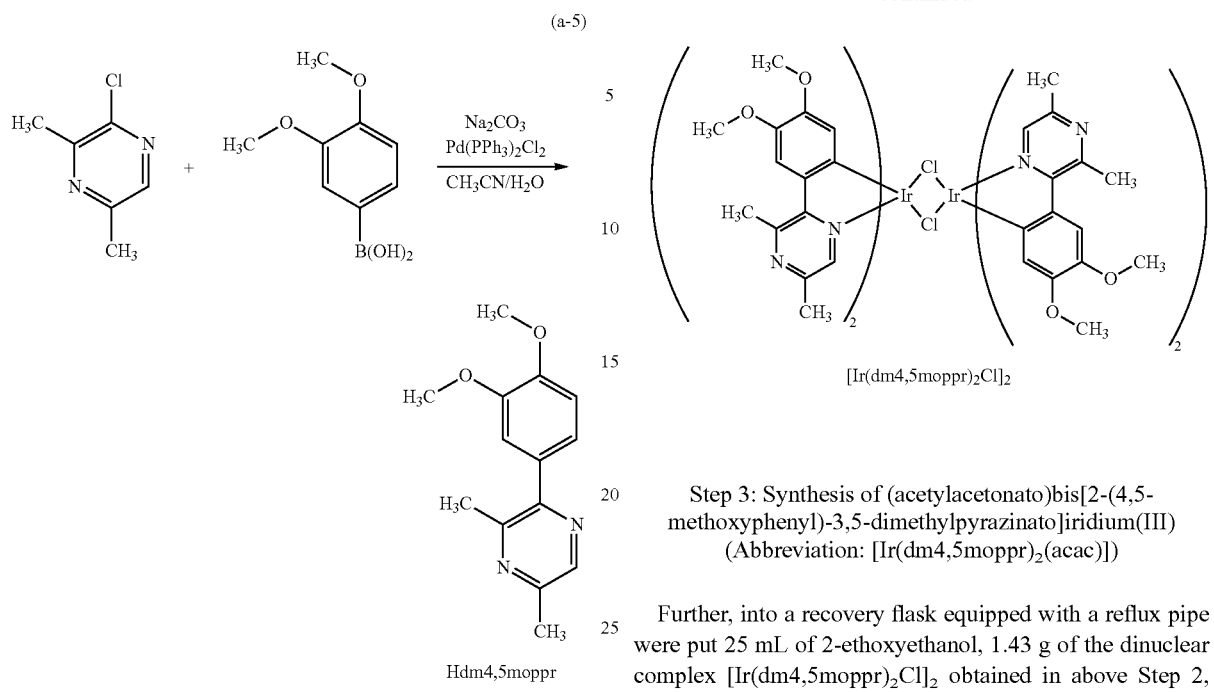

Hdm4,5moppr

[Ir(dm4,5moppr)$_2$Cl]$_2$

Step 3: Synthesis of (acetylacetonato)bis[2-(4,5-methoxyphenyl)-3,5-dimethylpyrazinato]iridium(III) (Abbreviation: [Ir(dm4,5moppr)$_2$(acac)])

Further, into a recovery flask equipped with a reflux pipe were put 25 mL of 2-ethoxyethanol, 1.43 g of the dinuclear complex [Ir(dm4,5moppr)$_2$Cl]$_2$ obtained in above Step 2, 0.31 mL of acetylacetone, and 1.06 g of sodium carbonate, and the atmosphere in the flask was replaced with argon. After that, irradiation with microwave (2.45 GHz, 100 W) for 30 minutes was performed to cause a reaction. The reaction solution was filtrated. The obtained solid was dissolved in ethanol and the solution was filtrated to remove insoluble matter. Then, the filtrate was recrystallized with ethanol, whereby the organometallic complex [Ir(dm4,5moppr)$_2$(acac)] which is one embodiment of the present invention was obtained (a red powder, yield: 43%). A synthesis scheme of Step 3 is shown in (c-5) below.

Step 2: Synthesis of di-μ-chloro-bis[bis{2-(4,5-methoxyphenyl)-3,5-dimethylpyrazinato}iridium(III)] (Abbreviation: [Ir(dm4,5moppr)$_2$Cl]$_2$)

Next, into a recovery flask equipped with a reflux pipe were put 15 mL of 2-ethoxyethanol, 5 mL of water, 1.91 g of Hdm4,5moppr obtained in above Step 1, and 0.93 g of iridium chloride hydrate (IrCl$_3$.H$_2$O) (produced by Sigma-Aldrich Corp.), and the atmosphere in the flask was replaced with argon. After that, irradiation with microwave (2.45 GHz, 100 W) for 30 minutes was performed to cause a reaction. The solution after the reaction was concentrated and a residue obtained was washed with ethanol, whereby a dinuclear complex [Ir(dm4,5moppr)$_2$Cl]$_2$ was obtained (a dark yellow powder, yield: 64%). A synthesis scheme of Step 2 is shown in (b-5) below.

(b-5)

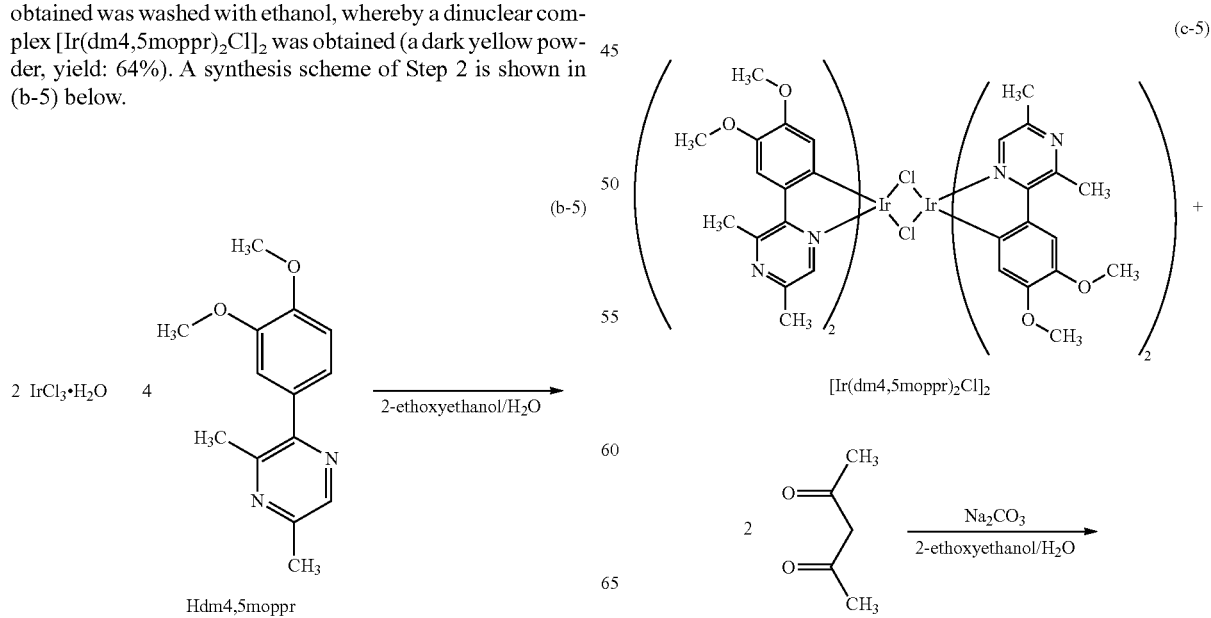

(c-5)

-continued

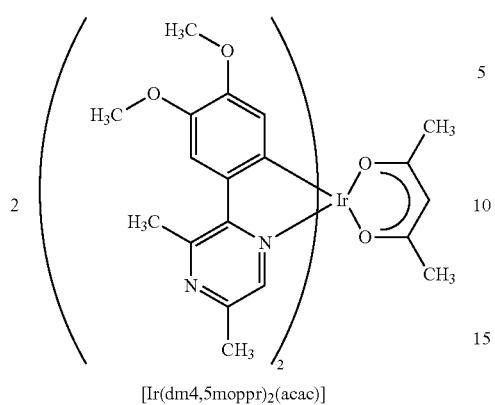

[Ir(dm4,5moppr)$_2$(acac)]

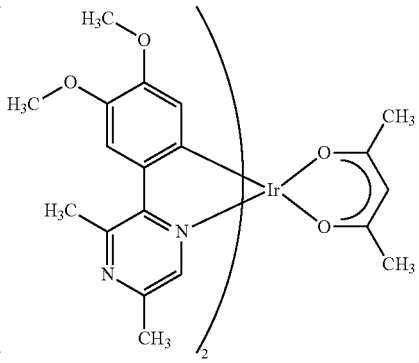

(112)

Figure 24:
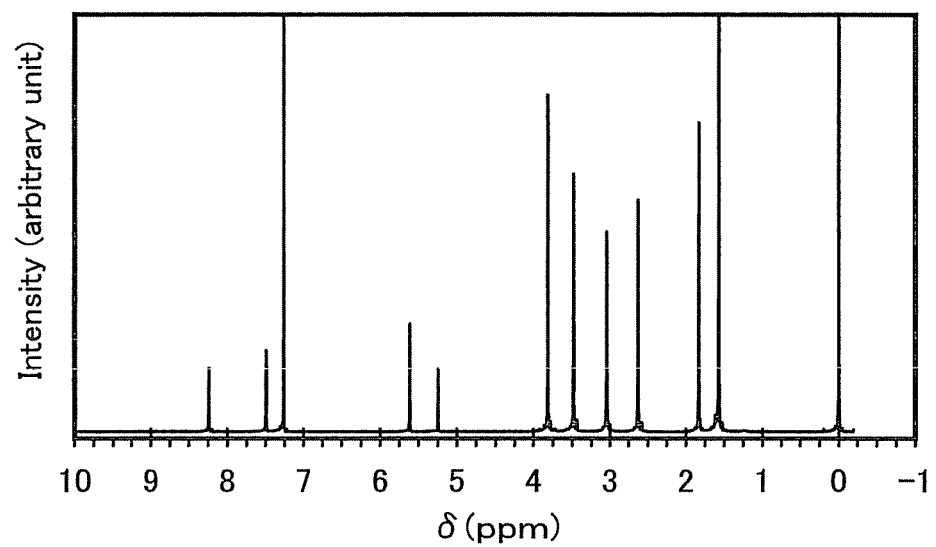
FIG. 24 is a $^1$H-NMR chart of an organometallic complex represented by Structural Formula (112)

Results of analysis of the red powder obtained in above Step 3 by nuclear magnetic resonance spectrometry ($^1$H NMR) are shown below. In addition, FIG. 24 is a $^1$H NMR chart. According to the results, it was found that the organometallic complex [Ir(dm4,5moppr)$_2$(acac)] of one embodiment of the present invention, which is represented by Structural Formula (112) above, was obtained in this example.

$^1$H-NMR. δ (CDCl$_3$): 1.83 (s, 6H), 2.63 (s, 6H), 3.05 (s, 6H), 3.48 (s, 6H), 3.82 (s, 6H), 5.25 (s, 1H), 5.61 (s, 2H), 7.49 (s, 2H), 8.24 (s, 2H).

Figure 25:
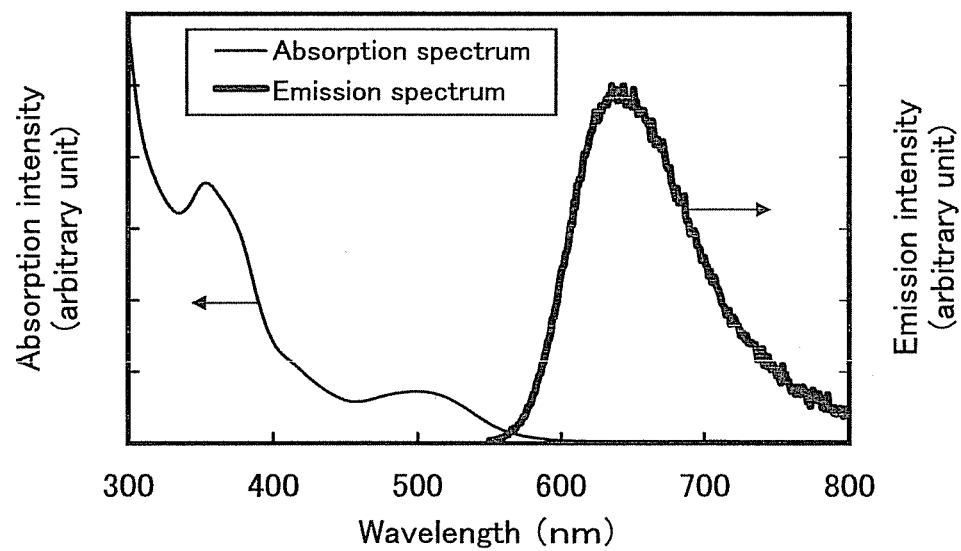
FIG. 25 is a graph showing an ultraviolet-visible absorption spectrum and an emission spectrum of the organometallic complex represented by Structural Formula (112)

Next, [Ir(dm4,5moppr)$_2$(acac)] was analyzed by an ultraviolet-visible (UV) absorption spectroscopy. The UV spectrum was measured using an ultraviolet-visible spectrophotometer (V550, produced by JASCO Corporation) at a room temperature by using a dichloromethane solution (0.066 mmol/L). In addition, an emission spectrum of [Ir(dm4,5moppr)$_2$(acac)] was measured. The emission spectrum was measured by a fluorescence spectrophotometer (FS920, produced by Hamamatsu Photonics Corporation) using a degassed dichloromethane solution (0.40 mmol/L) at a room temperature. FIG. 25 shows the measurement results. The horizontal axis indicates the wavelength (nm), and the vertical axis indicates the absorption intensity (arbitrary unit) and the emission intensity (arbitrary unit).

As shown in FIG. 25, the organometallic complex [Ir(dm4,5moppr)$_2$(acac)] which is one embodiment of the present invention has a peak of emission at 642 nm, and red light was observed from the dichloromethane solution.

Example 8

A light-emitting element (a light-emitting element 5) will be described in which the organometallic complex [Ir(dm4,5moppr)$_2$(acac)] of one embodiment of the present invention, which is represented by Structural Formula (112) and synthesized in Example 7, is used as a light-emitting substance. Note that of organic compounds used in this example, the ones described in Example 2 will not be described. In addition, an element structure of the light-emitting element will be described on the basis of FIG. 11.

<<Manufacture of Light-Emitting Element 5>>

First, as a first electrode 1101, indium tin oxide containing silicon oxide (ITSO) is formed to a thickness of 110 nm over a substrate 1100 made of glass. Note that the periphery of the ITSO is covered with an insulating film so that a surface of the ITSO of 2 mm×2 mm is exposed. Here, the first electrode 1101 is an electrode that functions as an anode of the light-emitting element.

Next, as pretreatment for forming the light-emitting element over the substrate 1100, the surface of the substrate was washed with water using a porous resin brush, baked at 200° C. for one hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injecting layer 1111, a hole-transporting layer 1112, a light-emitting layer 1113, an electron-transporting layer 1114, and an electron-injecting layer 1115 which are included in an EL layer 1102 are sequentially formed.

After reducing the pressure of the vacuum evaporation apparatus to 10$^{-4}$ Pa, NPB and molybdenum(VI) oxide were co-evaporated with a mass ratio of NPB to molybdenum(VI) oxide being 4:1, whereby the hole-injecting layer 1111 was formed. The thickness of the hole-injecting layer 1111 was 50 nm. Note that the co-evaporation is an evaporation method in which some different substances are evaporated from some different evaporation sources at the same time.

Next, NPB was evaporated to a thickness of 10 nm as a hole-transporting layer 1112.

Next, over the hole-transporting layer 1112, YGAO11 and [Ir(dm4,5moppr)$_2$(acac)] represented by above Structural Formula (102) were co-evaporated with a mass ratio of YGAO11 to [Ir(dm4,5moppr)$_2$(acac)] being 1:0.05, whereby the light-emitting layer 1113 was formed. The thickness of the light-emitting layer 1113 was 30 nm.

Next, after evaporating BAlq to a thickness of 10 nm, BPhen was further evaporated to a thickness of 20 nm, whereby the electron-transporting layer 1114 was formed. Furthermore, lithium fluoride was evaporated to a thickness of 2 nm over the electron-transporting layer 1114, whereby the electron-injecting layer 1115 was formed.

Next, aluminum was deposited to a thickness of 200 nm as a second electrode 1103. Thus, the light-emitting element 4 according to one embodiment of the present invention was obtained. Note that the second electrode 1103 is an electrode that functions as a cathode. In the above evaporation steps, evaporation was all performed by a resistance heating method.

Further, the light-emitting element was sealed in a glove box under a nitrogen atmosphere to prevent being exposed to the atmosphere.

<<Operation Characteristics of Light-Emitting Element 5>>

Operation characteristics of the manufactured light-emitting element 5 were measured. Note that the measurement was carried out at a room temperature (under an atmosphere in which the temperature was kept at 25° C.).

Figure 26:
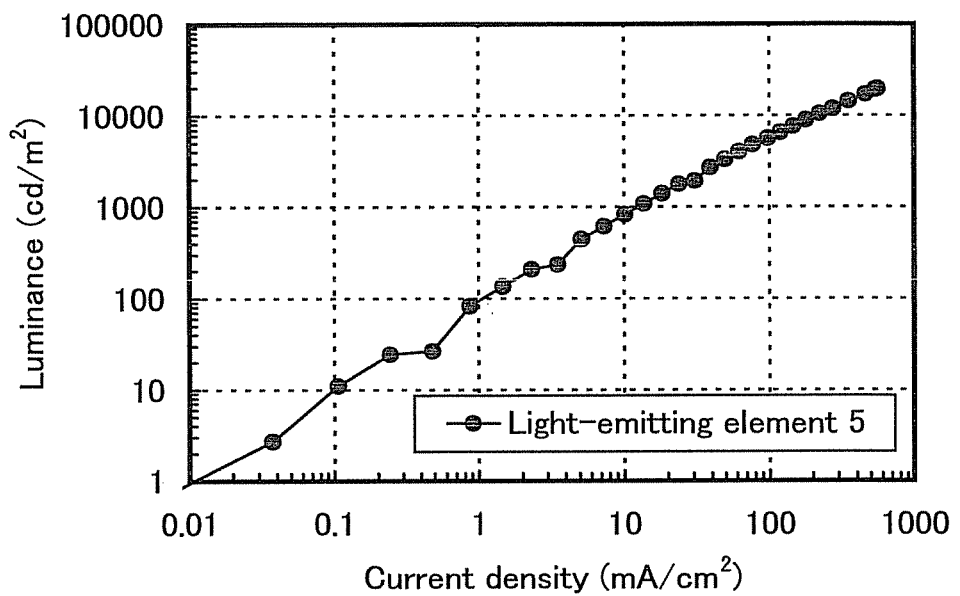
FIG. 26 is a graph showing current density-luminance characteristics of a light-emitting element which is one embodiment of the present invention.
Figure 27:
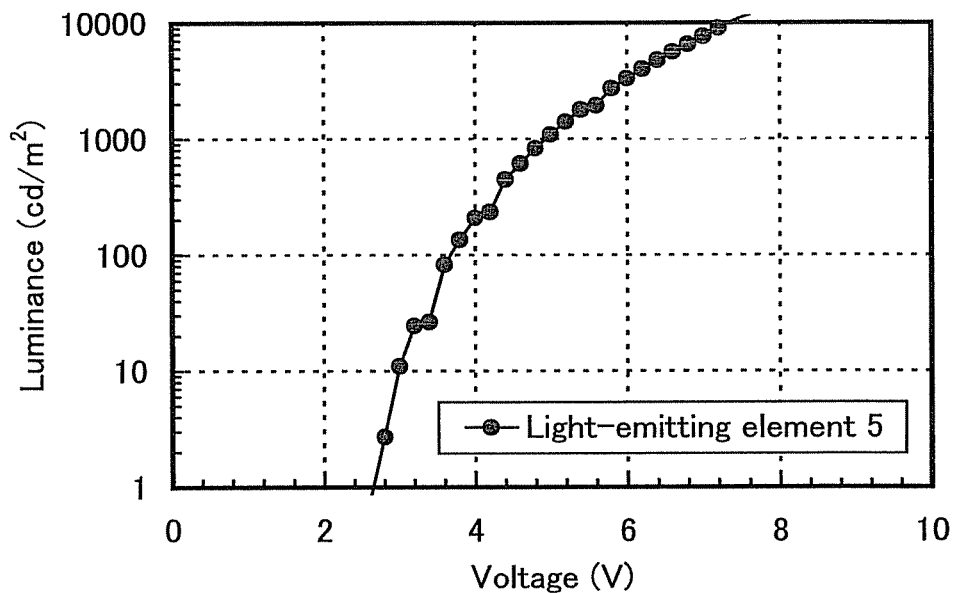
FIG. 27 is a graph showing voltage-luminance characteristics of the light-emitting element which is one embodiment of the present invention.

FIG. 26 shows current density-luminance characteristics of the light-emitting element 5. In FIG. 26, the vertical axis represents luminance (cd/m$^2$) and the horizontal axis represents current density (mA/cm$^2$). FIG. 27 shows voltage-luminance characteristics of the light-emitting element 5. In FIG. 27, the vertical axis represents luminance (cd/m$^2$) and the horizontal axis represents voltage (V).

In addition, the chromaticity of light emitted from the light-emitting element 5 is (0.66, 0.33), which shows that the light-emitting element 5 exhibits red emission with excellent color purity.

Figure 28:
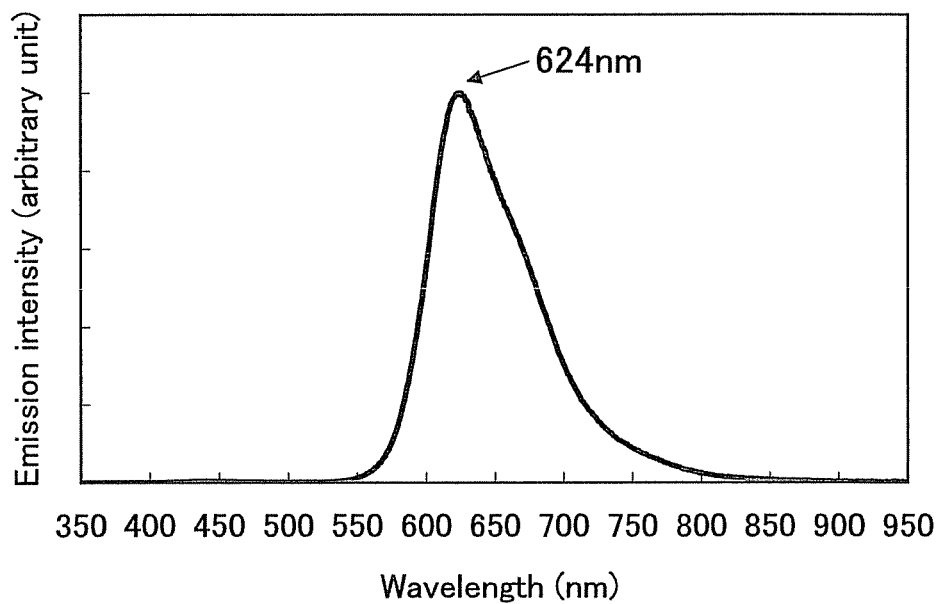
FIG. 28 is a graph showing an emission spectrum of the light-emitting element which is one embodiment of the present invention.

FIG. 28 shows an emission spectrum when a current at a current density of 25 mA/cm$^2$ was supplied to the light-emitting element 5. As shown in FIG. 28, the light-emitting element 5 has a peak of emission spectrum at 624 nm. FIG. 28 indicates that the emission spectrum of the light-emitting element 5 is derived from emission of the organometallic complex [Ir(dm4,5moppr)$_2$(acac)] which is one embodiment of the present invention.

Example 9

Synthesis Example 6

In this example, a synthesis method of an organometallic complex (acetylacetonato)bis[2-(3,5-methoxyphenyl)-3,5-dimethylpyrazinato]iridium(III) (abbreviation: [Ir(dm3,5moppr)$_2$(acac)]) of one embodiment of the present invention, which is represented by Structural Formula (124) in Embodiment 1, will be described. Note that a structure of [Ir(dm3,5moppr)$_2$(acac)] is shown below.

(122)

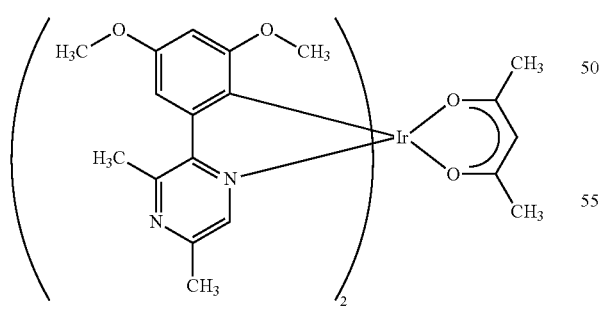

Step 1: Synthesis of 2-(3,5-dimethoxyphenyl)-3,5-dimethylpyrazine (Abbreviation: Hdm3,5moppr)

First, a recovery flask equipped with a reflux pipe were put 0.78 g of 2-chloro-3,5-dimethylpyrazine, 1.00 g of 3,5-dimethoxyphenylboronic acid, 0.58 g of sodium carbonate, 0.025 g of bis(triphenylphosphine)palladium(II)dichloride (abbreviation: Pd(PPh$_3$)$_2$Cl$_2$), 10 mL of water, and 10 mL of acetonitrile, and the atmosphere in the flask was replaced with argon. This reaction container was subjected to irradiation with microwave (2.45 GHz, 100 W) for 10 minutes to be heated. Note that the irradiation with microwave in this example was performed using a microwave synthesis system (Discover, produced by CEM Corporation).

Next, water was added to this solution, and an organic layer was extracted with dichloromethane. The obtained organic layer was washed with water and dried with magnesium sulfate. After the drying, the solution was filtrated. The solvent of this solution was distilled off, whereby a pyrazine derivative Hdm3,5moppr, which was a target substance, was obtained (dark yellow liquid, yield: 100%). A synthesis scheme of Step 1 is shown in (a-6) below.

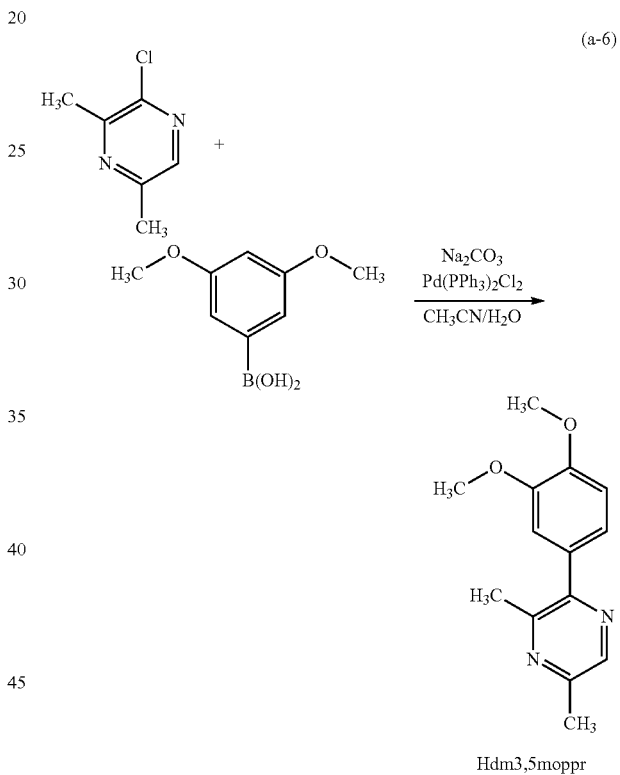

Step 2: Synthesis of di-μ-chloro-bis[bis{2-(3,5-dimethoxyphenyl)-3,5-dimethylpyrazinato}iridium (III)] (Abbreviation: [Ir(dm3,5moppr)$_2$Cl]$_2$)

Next, into a recovery flask equipped with a reflux pipe were put 15 mL of 2-ethoxyethanol, 5 mL of water, 1.39 g of Hdm3,5moppr obtained in above Step 1, and 0.68 g of iridium chloride hydrate (IrCl$_3$.H$_2$O) (produced by Sigma-Aldrich Corp.), and the atmosphere in the flask was replaced with argon. After that, irradiation with microwave (2.45 GHz, 100 W) for 30 minutes was performed to cause a reaction. The solution after the reaction was concentrated and a residue obtained was washed with ethanol, whereby a dinuclear complex [Ir(dm3,5moppr)$_2$Cl]$_2$ was obtained (a dark yellow powder, yield: 33%). Further, a synthesis scheme of Step 2 is shown in (b-6) below.

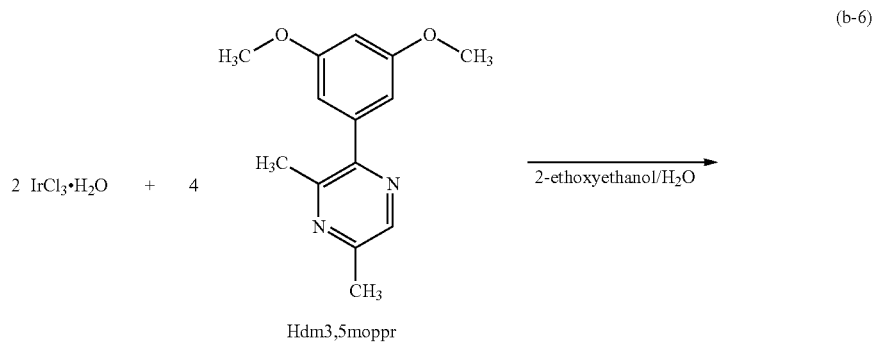

(b-6)

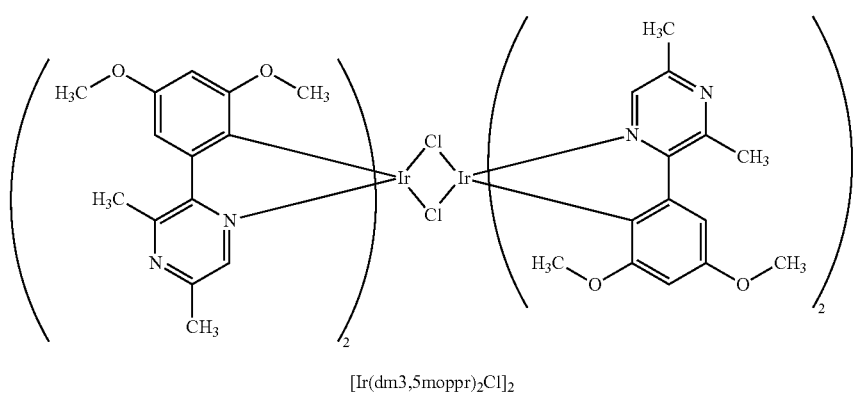

[Ir(dm3,5moppr)₂Cl]₂

Step 3: Synthesis of (acetylacetonato)bis[2-(3,5-dimethoxyphenyl)-3,5-dimethylpyrazinato]iridium(III) (Abbreviation: [Ir(dm3,5moppr)₂(acac)])

Further, into a recover flask equipped with a reflux pipe were put 25 mL of 2-ethoxyethanol, 0.54 g of the dinuclear complex [Ir(dm3,5moppr)₂Cl]₂ obtained in above Step 2, 0.12 mL of acetylacetone, and 0.40 g of sodium carbonate, and the atmosphere in the flask was replaced with argon. After that, irradiation with microwave (2.45 GHz, 100 W) for 30 minutes was performed to cause a reaction. The reaction solution was filtrated. The obtained solid was dissolved in ethanol and the solution was filtrated to remove insoluble matter. Then, the filtrate was recrystallized with ethanol, whereby an organometallic complex [Ir(dm3,5moppr)₂(acac)] which is one embodiment of the present invention was obtained (a red powder, yield: 49%). A synthesis scheme of Step 3 is shown in (c-6) below.

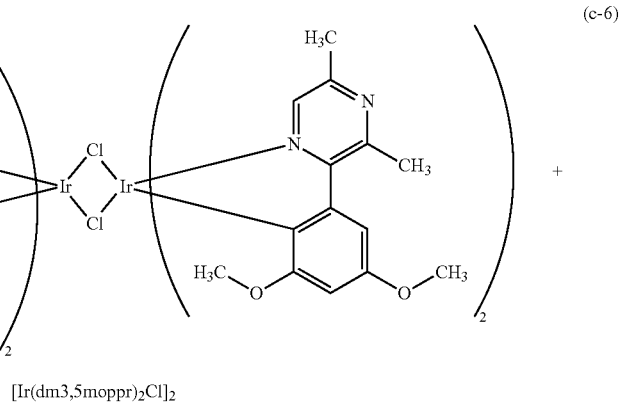

(c-6)

[Ir(dm3,5moppr)₂Cl]₂

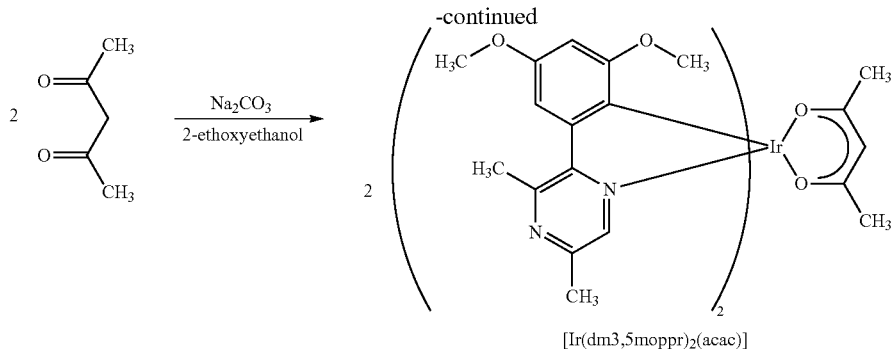

Figure 29:
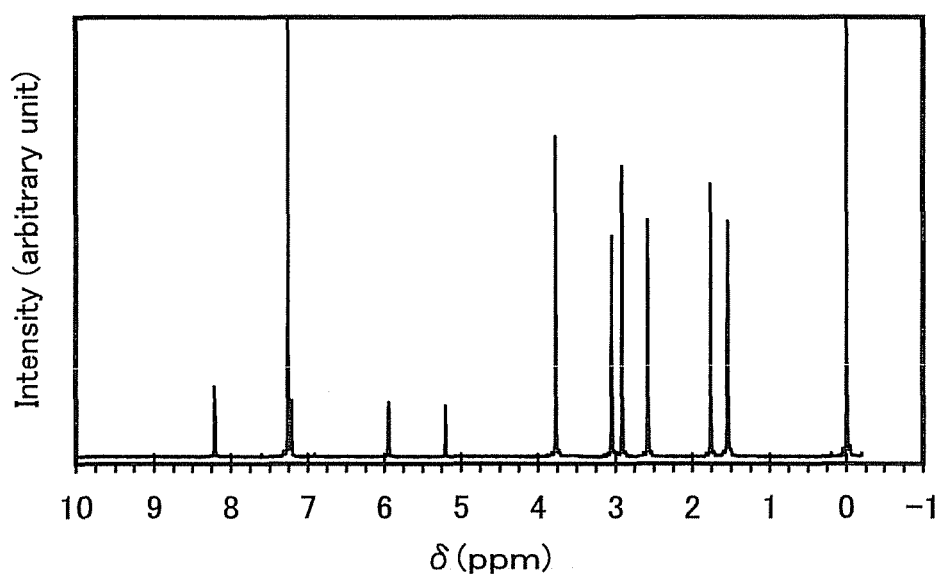
FIG. 29 is a $^1$H-NMR chart of an organometallic complex represented by Structural Formula (124)

Results of analysis of the red powder obtained in above Step 3 by nuclear magnetic resonance spectrometry ($^1$H NMR) are shown below. In addition, FIG. 29 is a $^1$H NMR chart. According to the results, it was found that the organometallic complex [Ir(dm3,5moppr)$_2$(acac)] of one embodiment of the present invention, which is represented by Structural Formula (124) above, was obtained in this example.

$^1$H-NMR. δ (CDCl$_3$): 1.76 (s, 6H), 2.58 (s, 6H), 2.92 (s, 6H), 3.05 (s, 6H), 3.77 (s, 6H), 5.21 (s, 1H), 5.95 (d, 2H), 7.22 (d, 2H), 8.21 (s, 2H).

Figure 30:
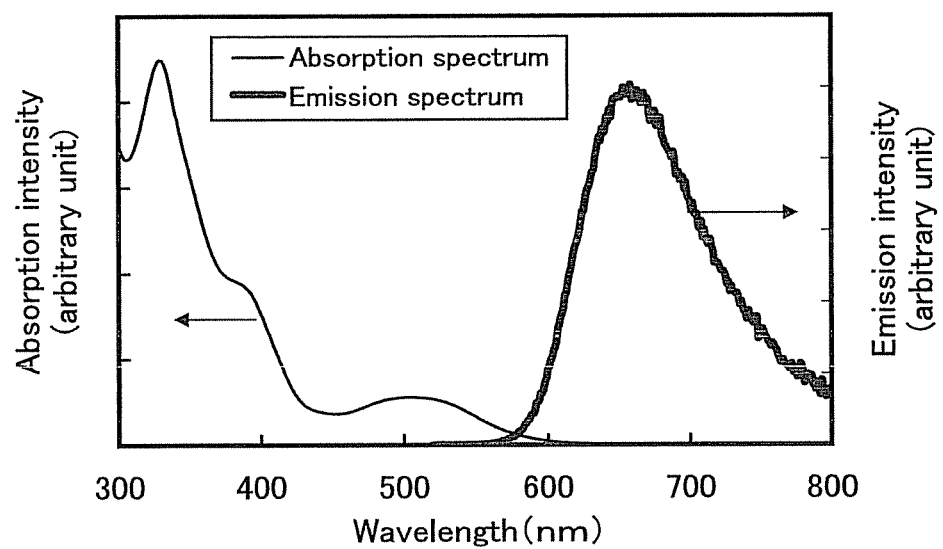
FIG. 30 is a graph showing an ultraviolet-visible absorption spectrum and an emission spectrum of the organometallic complex represented by Structural Formula (124)

Next, [Ir(dm3,5moppr)$_2$(acac)] was analyzed by an ultraviolet-visible (UV) absorption spectroscopy. The UV spectrum was measured using an ultraviolet-visible spectrophotometer (V550, produced by JASCO Corporation) at a room temperature by using a dichloromethane solution (0.067 mmol/L). In addition, an emission spectrum of [Ir(dm3,5moppr)$_2$(acac)] was measured. The emission spectrum was measured by a fluorescence spectrophotometer (FS920, produced by Hamamatsu Photonics Corporation) using a degassed dichloromethane solution (0.40 mmol/L) at a room temperature. FIG. 30 shows the measurement results. The horizontal axis indicates the wavelength (nm), and the vertical axis indicates the absorption intensity (arbitrary unit) and the emission intensity (arbitrary unit).

As shown in FIG. 30, the organometallic complex [Ir(dm3, 5moppr)$_2$(acac)] which is one embodiment of the present invention has a peak of emission at 653 nm, and red light was observed from the dichloromethane solution.

Example 10

In this example, a light-emitting element 6 in which the organometallic complex [Ir(dm5moppr)$_2$(acac)] of one embodiment of the present invention, which is represented by Structural Formula (100) and synthesized in Example 1, is used as a light-emitting substance; a light-emitting element 7 in which the organometallic complex [Ir(dm5moppr)$_2$(pic)] of one embodiment of the present invention, which is represented by Structural Formula (102) and synthesized in Example 3, is used as a light-emitting substance; and a light-emitting element 8 in which the organometallic complex [Ir(dm4,5moppr)$_2$(acac)] of one embodiment of the present invention, which is represented by Structural Formula (112) and synthesized in Example 7, is used as a light-emitting substance will be described. Note that of organic compounds used in this example, the ones described in Example 2 will not be described. In addition, an element structure of each of the light-emitting elements will be described on the basis of FIG. 11.

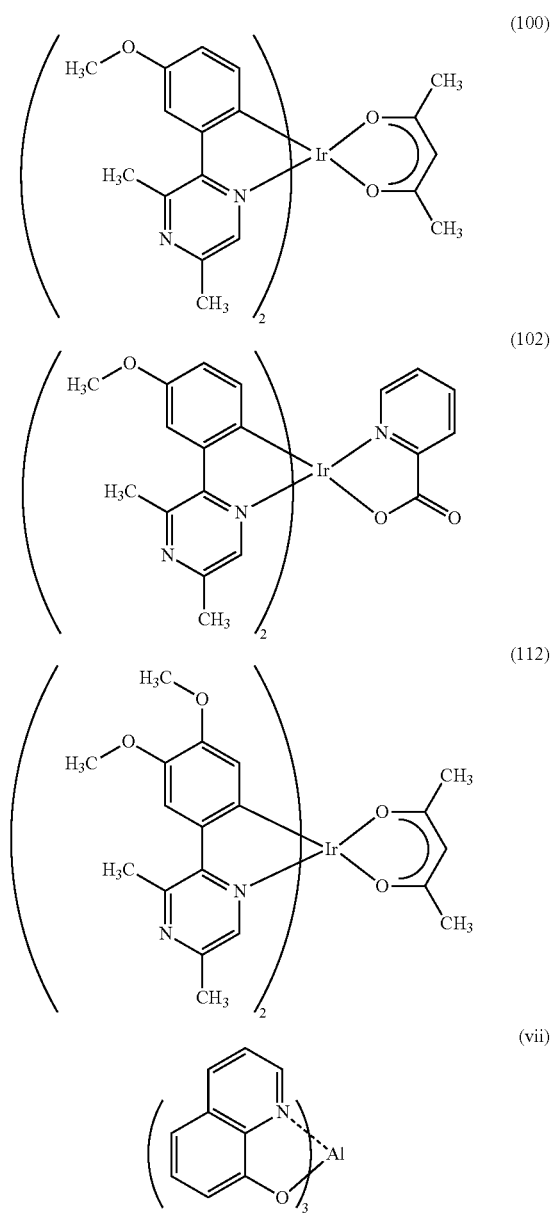

<<Manufacture of Light-Emitting Elements 6 to 8>>

First, as a first electrode 1101, indium tin oxide containing silicon oxide (ITSO) is formed to a thickness of 110 nm over a substrate 1100 made of glass. Note that the periphery of the ITSO is covered with an insulating film so that a surface of the ITSO of 2 mm×2 mm is exposed. Here, the first electrode 1101 is an electrode that functions as an anode of the light-emitting element.

Next, as pretreatment for forming the light-emitting element over the substrate 1100, the surface of the substrate was washed with water using a porous resin brush, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injecting layer 1111, a hole-transporting layer 1112, a light-emitting layer 1113, an electron-transporting layer 1114, and an electron-injecting layer 1115 which are included in an EL layer 1102 are sequentially formed.

After reducing the pressure of the vacuum evaporation apparatus to $10^{-4}$ Pa, 4,4'-bis[N-(1-naphtyl)-N-phenylamino] biphenyl (abbreviation: NPB) and molybdenum(VI) oxide were co-evaporated with a mass ratio of NPB to molybdenum (VI) oxide being 4:1, whereby the hole-injecting layer 1111 was formed. The thickness of the hole-injecting layer 1111 was 50 nm. Note that the co-evaporation is an evaporation method in which some different substances are evaporated from some different evaporation sources at the same time.

Next, NPB was evaporated to a thickness of 10 nm as a hole-transporting layer 1112.

Next, the light-emitting layer 1113 was formed over the hole-transporting layer 1112. In the case of the light-emitting element 6, over the hole-transporting layer 1112, bis(2-methyl-8-quinolinolato)(4-phenylphenolato)aluminum (abbreviation: BAlq), NPB, and [Ir(dm5moppr)$_2$(acac)] represented by above Structural Formula (100) were co-evaporated with a mass ratio of BAlq to NPB and [Ir(dm5moppr)$_2$(acac)] being 1:0.1:0.06, whereby the light-emitting layer 1113 was formed. In the case of the light-emitting element 7, over the hole-transporting layer 1112, BAlq, NPB, and [Ir(dm5moppr)$_2$(pic)] represented by above Structural Formula (102) were co-evaporated with a mass ratio of BAlq to NPB and [Ir(dm4,5moppr)$_2$(pic)] being 1:0.1:0.06, whereby the light-emitting layer 1113 was formed. In the case of the light-emitting element 8, over the hole-transporting layer 1112, BAlq, NPB, and [Ir(dm4,5moppr)$_2$(acac)] represented by above Structural Formula (112) were co-evaporated with a mass ratio of BAlq to NPB and [Ir(dm5moppr)$_2$(acac)] being 1:0.1:0.06, whereby the light-emitting layer 1113 was formed. The thickness of the light-emitting layer 1113 in each case was 30 nm.

Next, after evaporating tris(8-quinolinolato)aluminum(III) (abbreviation: Alq) represented by above Structural Formula (vii) to a thickness of 30 nm, bathophenanthroline (abbreviation: BPhen) was further evaporated to a thickness of 10 nm, whereby the electron-transporting layer 1114 was formed. Furthermore, lithium fluoride was evaporated to a thickness of 2 nm over the electron-transporting layer 1114, whereby the electron-injecting layer 1115 was formed.

Next, aluminum was deposited to a thickness of 200 nm as a second electrode 1103. Thus, the light-emitting elements (the light-emitting elements 6 to 8) each of which is one embodiment of the present invention were obtained. Note that the second electrode 1103 is an electrode that functions as a cathode. In the above evaporation steps, evaporation was all performed by a resistance heating method.

Further, these light-emitting elements were sealed in a glove box under a nitrogen atmosphere to prevent being exposed to the atmosphere.

<<Operation Characteristics of Light-Emitting Elements 6 to 8>>

Operation characteristics of each of the manufactured light-emitting elements (light-emitting elements 6 to 8) were measured. Note that the measurement was carried out at a room temperature (under an atmosphere in which the temperature was kept at 25° C.).

Figure 31:
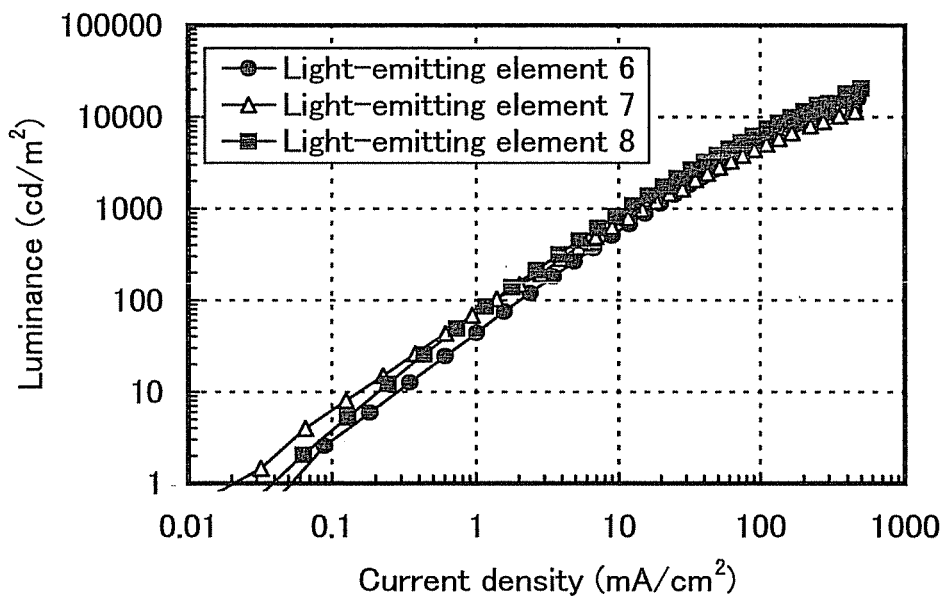
FIG. 31 is a graph showing current density-luminance characteristics of light-emitting elements each of which is one embodiment of the present invention.
Figure 32:
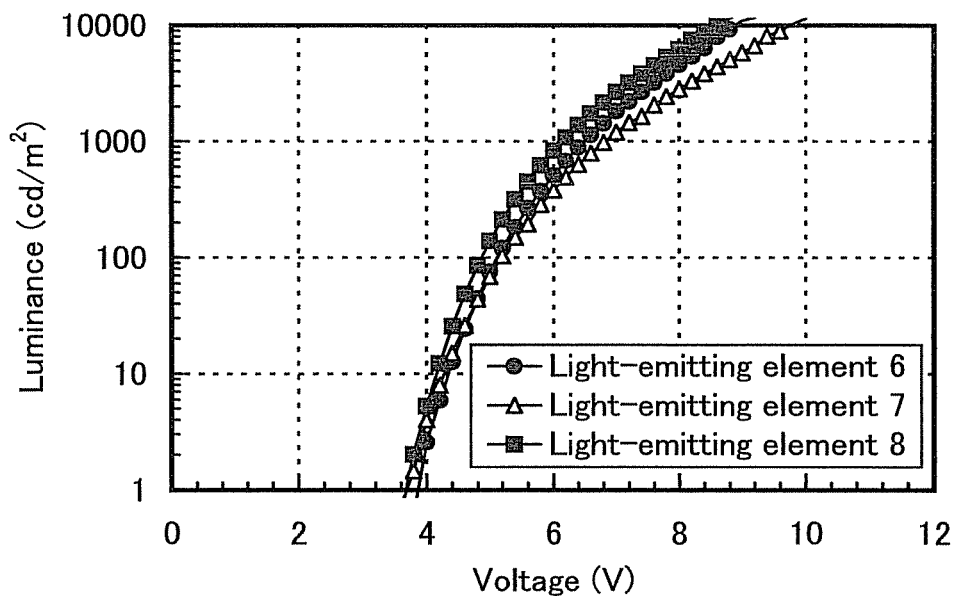
FIG. 32 is a graph showing voltage-luminance characteristics of the light-emitting elements each of which is one embodiment of the present invention.

FIG. 31 shows current density-luminance characteristics of each light-emitting element. In FIG. 31, the vertical axis represents luminance (cd/m$^2$) and the horizontal axis represents current density (mA/cm$^2$). FIG. 32 shows voltage-luminance characteristics of each light-emitting element. In FIG. 32, the vertical axis represents luminance (cd/m$^2$) and the horizontal axis represents voltage (V).

In addition, the chromaticities of light emitted from the light-emitting element 6, the light-emitting element 7, and the light-emitting element 8 are (0.67, 0.33), (0.65, 0.35), and (0.67, 0.33), respectively, which shows that these light-emitting elements exhibit red emission with excellent color purity.

Figure 33:
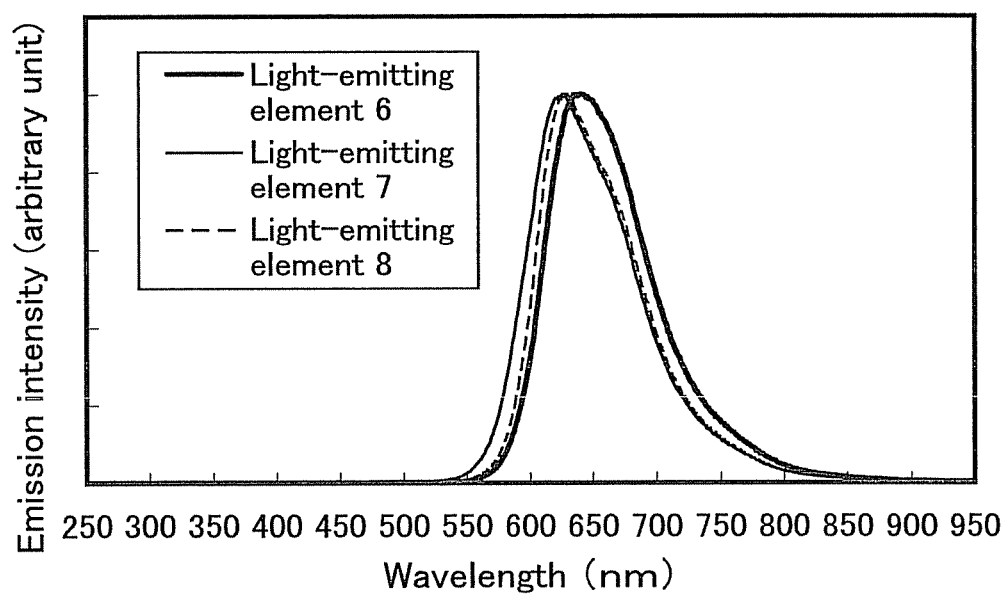
FIG. 33 is a graph showing emission spectra of the light-emitting elements each of which is one embodiment of the present invention.

FIG. 33 shows emission spectra when a current at a current density of 25 mA/cm$^2$ was supplied to each of the light-emitting elements 6 to 8. As shown in FIG. 33, the light-emitting element 6 has a peak of emission spectrum at 640 nm; the light-emitting element 7 has a peak of emission spectrum at 626 nm; and the light-emitting element 8 has a peak of emission spectrum at 628 nm. FIG. 33 indicates that the emission spectrum of the light-emitting element 6 is derived from emission of the organometallic complex [Ir(dm5moppr)$_2$(acac)] which is one embodiment of the present invention; the emission spectrum of the light-emitting element 7 is derived from emission of the organometallic complex [Ir(dm5moppr)$_2$(pic)] which is one embodiment of the present invention; and the emission spectrum of the light-emitting element 8 is derived from emission of the organometallic complex [Ir(dm4,5moppr)$_2$(acac)] which is one embodiment of the present invention.

This application is based on Japanese Patent Application serial no. 2009-010744 filed with Japan Patent Office on Jan. 21, 2009, the entire contents of which are hereby incorporated by reference.

What is claimed is:

1. A light-emitting device comprising:
   a pair of electrodes over a substrate;
   a hole-transporting layer and an electron-transporting layer between the pair of electrodes;
   a light-emitting layer between the hole-transporting layer and the electron-transporting layer,
   wherein the light-emitting layer contains an organometallic complex including an m-alkoxyphenyl pyrazine derivative.

2. The light-emitting device according to claim 1, wherein the m-alkoxyphenyl pyrazine derivative is represented by General Formula (G1),

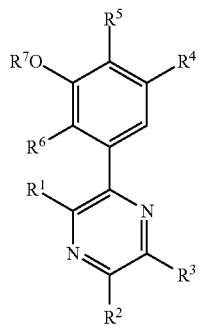

(G1)

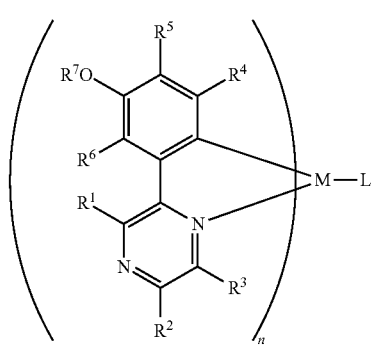

(G4)

wherein:
- $R^1$ represents any of an alkyl group having 1 to 4 carbon atoms, an alkoxy group having 1 to 4 carbon atoms, or an alkoxycarbonyl group having 1 to 5 carbon atoms;
- $R^2$ and $R^3$ each independently represent either hydrogen or an alkyl group having 1 to 4 carbon atoms;
- $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms;
- $R^7$ represents either a straight-chain alkyl group having 1 to 4 carbon atoms or a branched-chain alkyl group having 1 to 4 carbon atoms;
- an alkyl group may be substituted with a phenyl group; and
- M is a central metal and represents either an element belonging to Group 9 or an element belonging to Group 10.

3. The light-emitting device according to claim 1, wherein the organometallic complex exhibits a red phosphorescent emission.

4. The light-emitting device according to claim 1, wherein the central metal is iridium or platinum.

5. The light-emitting device according to claim 1, wherein the light-emitting device is incorporated in one selected from the group consisting of a television device, a computer, a portable game machine, a desk lamp, a cellular phone, an indoor lighting device.

6. A light-emitting device comprising:
- a pair of electrodes over a substrate;
- a hole-transporting layer and an electron-transporting layer between the pair of electrodes;
- a light-emitting layer between the hole-transporting layer and the electron-transporting layer,
- wherein the light-emitting layer contains an organometallic complex formed by an ortho-metalation of an m-alkoxyphenyl pyrazine derivative with respect to an ion of a metal belonging to Group 9 or Group 10.

7. The light-emitting device according to claim 6, wherein the m-alkoxyphenyl pyrazine derivative is represented by General Formula (G4), wherein:
- $R^1$ represents any of an alkyl group having 1 to 4 carbon atoms, an alkoxy group having 1 to 4 carbon atoms, or an alkoxycarbonyl group having 1 to 5 carbon atoms;
- $R^2$ and $R^3$ each independently represent either hydrogen or an alkyl group having 1 to 4 carbon atoms;
- $R^4$, $R^5$, and $R^6$ each independently represent any of hydrogen, an alkyl group having 1 to 4 carbon atoms, an alkoxy group having 1 to 4 carbon atoms, a halogen group, a trifluoromethyl group, or an aryl group having 6 to 12 carbon atoms;
- $R^7$ represents either a straight-chain alkyl group having 1 to 4 carbon atoms or a branched-chain alkyl group having 1 to 4 carbon atoms;
- an alkyl group may be substituted with a phenyl group;
- M is a central metal and represents either an element belonging to Group 9 or an element belonging to Group 10;
- L represents a monoanionic ligand; and
- n=2 in the case where the central metal is an element belonging to Group 9, and n=1 in the case where the central metal is an element belonging to Group 10.

8. The light-emitting device according to claim 6, wherein the monoanionic

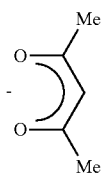

(L1)

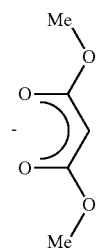

(L2)

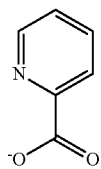

(L3)

(L4) 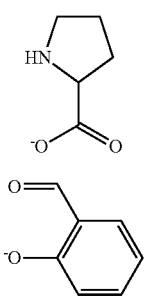

(L5) 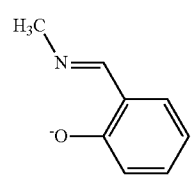

(L6) 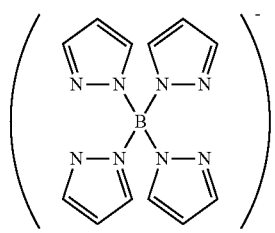

(L7) 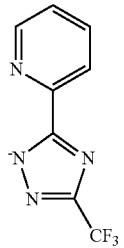

(L8) 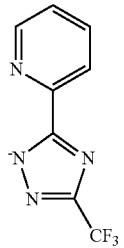

ligand is represented by any of Structural Formulae (L1) to (L8).

9. The light-emitting device according to claim 6, wherein the organometallic complex exhibits a red phosphorescent emission.

10. The light-emitting device according to claim 6, wherein the central metal is iridium or platinum.

11. The light-emitting device according to claim 6, wherein the light-emitting device is incorporated in one selected from the group consisting of a television device, a computer, a portable game machine, a desk lamp, a cellular phone, an indoor lighting device.

* * * * *